United States Patent
Doyle

(10) Patent No.: US 8,492,088 B2
(45) Date of Patent: Jul. 23, 2013

(54) ENGINEERING ENZYMES THROUGH GENETIC SELECTION

(75) Inventor: Donald F. Doyle, Marietta, GA (US)

(73) Assignee: Georgia Tech Research Corporation, Atlanta, GA (US)

(*) Notice: Subject to any disclaimer, the term of this patent is extended or adjusted under 35 U.S.C. 154(b) by 34 days.

(21) Appl. No.: 12/907,066

(22) Filed: Oct. 19, 2010

(65) Prior Publication Data
US 2011/0027820 A1    Feb. 3, 2011

Related U.S. Application Data

(63) Continuation-in-part of application No. 10/579,683, filed on Jan. 9, 2007, now abandoned.

(51) Int. Cl.
*C07H 21/04* (2006.01)
*C12N 15/00* (2006.01)
*A61K 38/04* (2006.01)
*G01N 33/53* (2006.01)
*C12Q 1/68* (2006.01)

(52) U.S. Cl.
USPC ........ 435/6.1; 536/23.5; 530/328; 435/320.1; 435/7.1

(58) Field of Classification Search
None
See application file for complete search history.

(56) References Cited

U.S. PATENT DOCUMENTS

2005/0158776 A1* 7/2005 Yan et al. ............................. 435/6
2008/0263687 A1* 10/2008 Kapitskaya et al. ............ 800/13

OTHER PUBLICATIONS

Duester, Retinoic Acid Synthesis and Signaling during Early Organogenesis, Cell. Sep. 19, 2008; 134(6): 921-931.*
Chen et al., A general strategy for the evolution of bond-forming enzymes using yeast display, PNAS Jul. 12, 2011 vol. 108 No. 28 11399-11404.*
Aranda et al., Nuclear Hormone Receptors and Gene Expression, Physiological Reviews vol. 81, No. 3, Jul. 2001.*
Chen et al., Nuclear receptor coactivator ACTR is a novel histone acetyltransferase and forms a multimeric activation complex with P/CAF and CBP/p300, Cell. Aug. 8, 1997;90(3):569-80.*

(Continued)

*Primary Examiner* — Jim Ketter
*Assistant Examiner* — Reza Ghafoorian
(74) *Attorney, Agent, or Firm* — Thomas|Horstemeyer, LLP

(57) ABSTRACT

The disclosure provide a system for the selection of variant nuclear receptor ligand binding domains, or for the selection of variant enzymes that have an enhanced ability to synthesize a nuclear receptor ligand or a precursor thereof. The disclosure provides yeast cells comprising: a yeast transcription modulating system comprising a nucleic acid expression system encoding a nuclear receptor ligand-binding domain linked to a DNA-binding domain, a nucleic acid expression system encoding a coactivator domain linked to a yeast transcriptional activator, a heterologous enzyme system for generating a nuclear receptor ligand, and a selective genetic locus expressed in the presence of the recombinant nuclear receptor polypeptide and a nuclear receptor ligand specifically bound to the recombinant nuclear receptor polypeptide. The disclosure also provides methods of using the yeast cell system for identifying variant nuclear receptor ligand binding domains or variant enzymes synthesizing a nuclear receptor ligand.

29 Claims, 19 Drawing Sheets

OTHER PUBLICATIONS

Shinkyo et al., Metabolism of vitamin D by human microsomal CYP2R1, Biochemical and Biophysical Research Communications 324 (2004) 451-457.*

Takeyama et al., 25-Hydroxyvitamin D3 1 a-Hydroxylase and Vitamin D Synthesis, Science, Vol. 277, Sep. 19, 1997 p. 1827.*

Zhao et al., Analysis of Vitamin D Analog—Induced Heterodimerization of Vitamin D Receptor with Retinoid X Receptor Using the Yeast Two-Hybrid System, Molecular Endocrinology 11: 366-378, 1997.*

Zhang, et al., "Genomic Analysis of the Nuclear Receptor Family: New Insights Into Structure, Regulation, and Evolution from the Rat Genome", Genome Research, pp. 580-590, Dec. 10, 2003.

* cited by examiner

SEQUENCE LISTING

<160> NUMBER OF SEQ ID NOS: 22

<210> SEQ ID NO 1
<211> LENGTH: 17
<212> TYPE: DNA
<213> ORGANISM: Artificial sequence
<220> FEATURE:
<223> OTHER INFORMATION: Primer

<400> SEQUENCE: 1
cggaatttcc catgggc                                                  17

<210> SEQ ID NO 2
<211> LENGTH: 37
<212> TYPE: DNA
<213> ORGANISM: Artificial sequence
<220> FEATURE:
<223> OTHER INFORMATION: Primer

<400> SEQUENCE: 2
ctcgccgaac gacccggtca ccgcatgcca ctagtgg                            37

<210> SEQ ID NO 3
<211> LENGTH: 36
<212> TYPE: DNA
<213> ORGANISM: Artificial sequence
<220> FEATURE:
<223> OTHER INFORMATION: Primer

<400> SEQUENCE: 3
ccgcttggcc cactccacta gtggcatgcg gtgacc                             36

<210> SEQ ID NO 4
<211> LENGTH: 37
<212> TYPE: DNA
<213> ORGANISM: Artificial sequence
<220> FEATURE:
<223> OTHER INFORMATION: Primer

<400> SEQUENCE: 4
cgggcaggct ggaatgagct cctcgacgga attctcc                            37

<210> SEQ ID NO 5
<211> LENGTH: 36
<212> TYPE: DNA
<213> ORGANISM: Artificial sequence
<220> FEATURE:
<223> OTHER INFORMATION: Primer

<400> SEQUENCE: 5
cagcccggtg gccaggagaa ttccgtcgag gagctc                             36

<210> SEQ ID NO 6
<211> LENGTH: 40
<212> TYPE: DNA
<213> ORGANISM: Artificial sequence
<220> FEATURE:
<223> OTHER INFORMATION: Primer

<400> SEQUENCE: 6
ctctgcgctc catcgggctt aagtgcccac caattgacac                         40

<210> SEQ ID NO 7
<211> LENGTH: 46
<212> TYPE: DNA

-continued

<213> ORGANISM: Artificial sequence
<220> FEATURE:
<223> OTHER INFORMATION: Primer

<400> SEQUENCE: 7
ctccagcatc tccataagga aggtgtcaat tggtgggcac ttaagc        46

<210> SEQ ID NO 8
<211> LENGTH: 17
<212> TYPE: DNA
<213> ORGANISM: Artificial sequence
<220> FEATURE:
<223> OTHER INFORMATION: Primer

<400> SEQUENCE: 8
caaaggatgg gccgcag        17

<210> SEQ ID NO 9
<211> LENGTH: 46
<212> TYPE: DNA
<213> ORGANISM: Artificial sequence
<220> FEATURE:
<223> OTHER INFORMATION: Primer

<400> SEQUENCE: 9
ggcaaacatg gggctgaacc ccagctcgcc gaacgacccg gtcacc        46

<210> SEQ ID NO 10
<211> LENGTH: 66
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (33)..(38)
<223> OTHER INFORMATION: n is a, c, g, or t
<220> FEATURE:
<221> NAME/KEY: misc_feature
<222> LOCATION: (45)..(46)
<223> OTHER INFORMATION: n is a, c, g, or t

<400> SEQUENCE: 10
gcccactcca ctagtgtgaa aagctgtttg tcnnnnnntt ggcanngttg gtgaccgggt        60
cgttcg        66

<210> SEQ ID NO 11
<211> LENGTH: 48
<212> TYPE: DNA
<213> ORGANISM: Artificial sequence
<220> FEATURE:
<223> OTHER INFORMATION: Primer

<400> SEQUENCE: 11
cttttcacac tagtggagtg ggccaagcgg atcccacact tctcagag        48

<210> SEQ ID NO 12
<211> LENGTH: 28
<212> TYPE: DNA
<213> ORGANISM: Artificial sequence
<220> FEATURE:
<223> OTHER INFORMATION: Primer

<400> SEQUENCE: 12
ggggcagctc tgagaagtgt gggatccg        28

<210> SEQ ID NO 13

```
<211> LENGTH: 48
<212> TYPE: DNA
<213> ORGANISM: Artificial sequence
<220> FEATURE:
<223> OTHER INFORMATION: Primer
<220> FEATURE:
<221> NAME/KEY: misc_feature
<222> LOCATION: (22)..(24)
<223> OTHER INFORMATION: n is a, c, g, or t
<220> FEATURE:
<221> NAME/KEY: misc_feature
<222> LOCATION: (31)..(33)
<223> OTHER INFORMATION: n is a, c, g, or t

<400> SEQUENCE: 13
gcaggctgga atgagctcct cnnngcctcc nnntcccacc gctccatc            48

<210> SEQ ID NO 14
<211> LENGTH: 46
<212> TYPE: DNA
<213> ORGANISM: Artificial sequence
<220> FEATURE:
<223> OTHER INFORMATION: Primer

<400> SEQUENCE: 14
ccggtggcca ggagaattcc gtccttcacg gcgatggagc ggtggg              46

<210> SEQ ID NO 15
<211> LENGTH: 63
<212> TYPE: DNA
<213> ORGANISM: Artificial sequence
<220> FEATURE:
<223> OTHER INFORMATION: AM1
<220> FEATURE:
<221> NAME/KEY: misc_feature
<222> LOCATION: (38)..(40)
<223> OTHER INFORMATION: n is a, c, g, or t

<400> SEQUENCE: 15
ggctctgcgc tccatcgggc ttaagtgcct ggaacatnnn ttscttcttc aagctcatcg    60
ggg                                                                 63

<210> SEQ ID NO 16
<211> LENGTH: 51
<212> TYPE: DNA
<213> ORGANISM: Artificial sequence
<220> FEATURE:
<223> OTHER INFORMATION: AM2

<400> SEQUENCE: 16
gcatctcaat aaggaaggtg tcaattgtgt gtccccgatg agcttgaaga a          51

<210> SEQ ID NO 17
<211> LENGTH: 12414
<212> TYPE: DNA
<213> ORGANISM: Artificial sequence
<220> FEATURE:
<223> OTHER INFORMATION: Artificial vector

<400> SEQUENCE: 17
gcttgcatgc aacttctttt cttttttttt cttttctctc tccccgttg ttgtctcacc    60 atatccgcaa tgacaaaaaa aatgatggaa gacactaaag gaaaaaatta acgacaaaga   120
cagcaccaac agatgtcgtt gttccagagc tgatgagggg tatcttcgaa cacacgaaac   180
tttttccttc cttcattcac gcacactact ctctaatgag caacggtata cggccttcct   240
tccagttact tgaatttgaa ataaaaaaag tttgccgctt gctatcaag tataaataga    300
```

```
cctgcaatta ttaatctttt gtttcctcgt cattgttctc gttccctttc ttccttgttt      360 cttttctgc acaatatttc aagctatacc aagcatacaa tcaactccaa gctttgcaaa       420
gatggataaa gcggaattaa ttcccgagcc tccaaaaaag aagagaaagg tcgaattggg      480
taccgccgcc aattttaatc aaagtgggaa tattgctgat agctcattgt ccttcacttt      540
cactaacagt agcaacggtc cgaacctcat aacaactcaa acaaattctc aagcgctttc      600
acaaccaatt gcctcctcta acgttcatga taacttcatg aataatgaaa tcacggctag      660
taaaattgat gatggtaata attcaaaacc actgtcacct ggttggacgg accaaactgc      720
gtataacgcg tttggaatca ctacagggat gtttaatacc actacaatgg atgatgtata      780
taactatcta ttcgatgatg aagataccccc accaaaccca aaaaagaga tctttatgag      840 tggattagga gaaaacttgg atccactggc cagtgattca cgaaaacgca aattgccatg      900
tgatactcca ggacaaggtc ttacctgcag tggtgaaaaa cggagacggg agcaggaaag      960
taaatatatt gaagaattgg ctgagctgat atctgccaat cttagtgata ttgacaattt     1020
caatgtcaaa ccagataaat gtgcgatttt aaaggaaaca gtaagacaga tacgtcaaat     1080
aaaagagcaa ggaaaaacta tttccaatga tgatgatgtt caaaaagccg atgtatcttc     1140
tacagggcag ggagttattg ataaagactc cttaggaccg cttttacttc aggcattgga     1200
tggtttccta tttgtggtga atcgagacgg aaacattgta tttgtatcag aaaatgtcac     1260
acaatacctg caatataagc aagaggacct ggttaacaca agtgtttaca atatcttaca     1320
tgaagaagac agaaaggatt ttcttaagaa tttaccaaaa tctacagtta atggagtttc     1380
ctggacaaat gagacccaaa gacaaaaaag ccatacattt aattgccgta tgttgatgaa     1440
aacaccacat gatattctgg aagacataaa cgccagtcct gaaatgcgcc agagatatga     1500
aacaatgcag tgctttgccc tgtctcagcc acgagctatg atggaggaag gggaagattt     1560
gcaatcttgt atgatctgtg tggcacgccg cattactaca ggagaaagaa catttccatc     1620
aaaccctgag agctttatta ccagacatga tctttcagga aaggttgtca atatagatac     1680
aaattcactg agatcctcca tgaggcctgg cttttgaagat ataatccgaa ggtgtattca     1740 gagattttt agtctaaatg atgggcagtc atggtcccag aaacgtcact atcaagaagt     1800
taccagtgat gggatatttt ccccaacagc ttatcttaat ggccatgcag aaacccagt     1860 atatcgattc tcgttggctg atggaactat agtgactgca cagacaaaaa gcaaactctt     1920
ccgaaatcct gtaacaaatg atcgacatgg cttttgtctca acccacttcc ttcagagaga    1980
acagaatgga tatagaccaa acccaaatcc tgttggacaa gggattagac cacctatggc     2040
tggatgcaac agttcggtag gcggcatgag tatgtcgcca aaccaaggct tacagatgcc     2100
gagcagcagg gcctatggct tggcagaccc tagcaccaca gggcagatga gtggagctag     2160
gtatgggggt tccagtaaca tagcttcatt gacccctggg ccaggcatgc aatcaccatc     2220
ttcctaccag aacaacaact ataggctcaa catgagtagc cccccacatg ggagtcctgg     2280
tcttgcccca aaccagcaga atatcatgat ttctcctcgt aatcgtggga gtccaaagat     2340
agcctcacat cagttttctc ctgttgcagg tgtgcactct cccatggcat cttctggcaa     2400
tactgggaac cacagctttt ccagcagctc tctcagtgcc ctgcaagcca tcagtgaagg     2460 tgtgggact tccctttat ctactctgtc atcaccaggc cccaaattgg ataactctcc       2520
caatatgaat attacccaac caagtaaagt aagcaatcag gattccaaga gtcctctggg    2580
cttttattgc gaccaaaatc cagtggagag ttcaatgtgt cagtcaaata gcagagatca    2640
cctcagtgac aaagaaagta aggagagcag tgttgagggg gcagagaatc aaaggggtcc    2700
```

-continued

```
tttggaaagc aaaggtcata aaaaattact gcagttactt acctgttctt ctgatgaccg    2760
gggtcattcc tccttgacca actccccct agattcaagt tgtaaagaat cttctgttag     2820
tgtcaccagc ccctctggag tctcctcctc tacatctgga ggagtatcct ctacatccaa    2880
tatgcatggg tcactgttac aagagaagca ccggattttg cacaagttgc tgcagaatgg    2940
gaattcacca gctgaggtag ccaagattac tgcagaagcc actgggaaag acaccagcag    3000
tataacttct tgtggggacg gaaatgttgt caagcaggag cagctaagtc ctaagaagaa    3060
ggagaataat gcacttctta gatacctgct ggacagggat gatcctagtg atgcactctc    3120
taaagaacta cagccccaag tggaaggagt ggataataaa atgagtcagt gcaccagctc    3180
caccattcct agctcaagtc aagagaaaga ccctaaaatt aagacagaga caagtgaaga    3240
gggatctgga gacttggata atctagatgc tattcttggt gatctgacta gttctgactt    3300
ttacaataat tccatatcct caaatggtag tcatctgggg actaagcaac aggtgtttca    3360
aggaactaat tctctgggtt tgaaaagttc acagtctgtg cagtctattc gtcctccata    3420
taaccgagca gtgtctctgg atagccctgt ttctgttggc tcaagtcctc cagtaaaaaa    3480
tatcagtgct ttccccatgt taccaaagca acccatgttg ggtgggaatc caagaatgat    3540
ggatagtcag gaaaattatg gctcaagtat gggagactgg ggcttaccaa actcaaaggc    3600
cggcagaatg gaacctatga attcaaactc catgggaaga ccaggaggag attataatac    3660
ttctttaccc agacctgcac tgggtggctc tattcccaca ttgcctcttc ggtctaatag    3720
cataccaggt gcgagaccag tattgcaaca gcagcagcag atgcttcaaa tgaggcctgg    3780
tgaaatcccc atgggaatgg gggctaatcc ctatggccaa gcagcagcat ctaaccaact    3840
gggttcctgg cccgatggca tgttgtccat ggaacaagtt tctcatggca ctcaaaatag    3900
gcctcttctt aggaattccc tggatgatct tgttgggcca ccttccaacc tggaaggcca    3960
gagtgacgaa agagcattat ggaccagct gcacactctt ctcagcaaca cagatgccac    4020
aggcctggaa gaaattgaca gagctttggg cattcctgaa cttgtcaatc agggacaggc    4080
attagagccc aaacaggatg ctttccaagg ccaagaagca gcagtaatga tggatcagaa    4140
ggcaggatta tatggacaga cataccagc acagggggct ccaatgcaag gaggctttca    4200
tcttcaggga caatcaccat cttttaactc tatgatgaat cagatgaacc agcaaggcaa    4260
ttttcctctc caaggaatgc acccacgagc caacatcatg agaccccgga caaacacccc    4320
caagcaactt agaatgcagc ttcagcagag gctgcagggc cagcagtttt tgaatcagag    4380
ccgacaggca cttgaattga aaatggaaaa ccctactgct ggtggtgctg cggtgatgag    4440
gcctatgatg cagcccccagc agggttttct taatgctcaa atggtcgccc aacgcagcag    4500
agagctgcta agtcatcact ccgacaacaa gagggtggct atgatgatgc agcagcagca    4560
acagcagcag cagcagcagc agcagcagca acagcaacag caacagcaac agcagcaaca    4620
gcagcaaacc caggccttca gcccacctcc taatgtgact gcttcccca gcatggatgg    4680 gcttttggca ggacccacaa tgccacaagc tcctccgcaa cagtttccat atcaaccaaa    4740
ttatggaatg gacaacaac cagatccagc ctttggtcga gtgtctagtc ctcccaatgc    4800
aatgatgtcg tcaagaatgg gtccctccca gaatcccatg atgcaacacc cgcaggctgc    4860
atccatctat cagtcctcag aaatgaaggg ctggccatca ggaaatttgg ccaggaacag    4920 ctcctttttcc cagcagcagt tgcccacca ggggaatcct gcagtgtata gtatggtgca    4980
catgaatggc agcagtggtc acatgggaca gatgaacatg aaccccatgc ccatgtctgg    5040
catgcctatg ggtcctgatc agaaatactg ctgacatctc tgcaccagga cctcttaagg    5100
```

```
aaaccactgt acaaatgaca ctgcactagg attattggga aggaatcatt gttccaggca    5160
tccatcttgg aagaaaggac cagctttgag ctccatcaag ggtattttaa gtgatgtcat    5220
ttgagcagga ctggatttta agccgaaggg caatatctac gtgttttcc ccctccttc      5280 tgctgtgtat catggtgttc aaaacagaaa tgttttttgg cattccacct cctagggata    5340
taattctgga gacatggagt gttactgatc ataaaacttt tgtgtcactt ttttctgcct    5400
tgctagccaa atctcttaa atacacgtag gtgggccaga gaacattgga gaatcaaga     5460 gagattagaa tatctggttt ctctagttgc agtattggac aaagagcata gtcccagcct    5520
tcaggtgtag tagttctgtg ttgacccttt gtccagtgga attggtgatt ctgaattgtc    5580
ctttactaat ggtgttgagt tgctctgtcc ctattatttg ccctaggctt tctcctaatg    5640
aaggttttca tttgccattc atgtcctgta atacttcacc tccaggaact gtcatggatg    5700
tccaaatggc tttgcagaaa ggaaatgaga tgacagtatt taatcgcagc agtagcaaac    5760
ttttcacatg ctaatgtgca gctgagtgca ctttatttaa aaagaatgga taaatgcaat    5820
attcttgagg tcttgaggga atagtgaaac acattcctgg ttttgccta cacttacgtg     5880 ttagacaaga actatgattt ttttttttaa agtactggtg tcaccctttg cctatatggt    5940
agagcaataa tgcttttta aaataaactt ctgaaaaccc aaggccaggt actgcattct     6000
gaatcagaat ctcgcagtgt ttctgtgaat agatttttt gtaaatatga cctttaagat     6060
attgtattat gtaaaatatg tataaccttt ttttgtagg tcacaacaac tcattttac      6120 agagtttgtg aagctaaata tttaacattg ttgatttcag taagctgtgt ggtgaggcta    6180
ccagtggaag agacatccct tgacttttgt ggcctggggg agggg tagtg caccacagct    6240 tttccttccc cacccccag ccttagatgc ctcgctcttt tcaatctctt aatctaaatg     6300
ctttttaaag agattatttg tttagatgta ggcattttaa tttttaaaa attcctctac      6360 cagaactaag cactttgtta atttgggggg aaagaataga tatggggaaa taaacttaaa   6420
aaaaaatcag gaatttaaaa aaaacagaca atttgaagag aatctttgg attttaagca     6480 gtccgaaata atagcaattc atgggctgtg tgtgtgtg tatgtgtgtg tgtgtgtgtg      6540 tatgttaat tatgttacct tttcatcccc tttaggagcg ttttcagatt ttggttcgta     6600
agacctgaat cccgcggccg ccccgggcgt agatactgaa aaaccccgca agttcacttc    6660
aactgtgcat cgtgcaccat ctcaatttct ttcatttata catcgttttg ccttctttta    6720
tgtaactata ctcctctaag tttcaatctt ggccatgtaa cctctgatct atagaatttt    6780
ttaaatgact agaattaatg cccatctttt ttttggacct aaattcttca tgaaaatata    6840
ttacgagggc ttattcagaa gctttggact tcttcgccag aggtttggtc aagtctccaa    6900
tcaaggttgt cggcttgtct accttgccag aaatttacga aaagatggaa aagggtcaaa    6960
tcgttggtag atacgttgtt gacacttcta aataagcgaa tttcttatga tttatgattt    7020
ttattattaa ataagttata aaaaaaataa gtgtatacaa attttaaagt gactcttagg    7080
ttttaaaacg aaaattcttg ttcttgagta actctttcct gtaggtcagg ttgctttctc    7140
aggtatagca tgaggtcgct cttattgacc acacctctac cggcatgccc gaaattcccc    7200
taccctatga acatattcca ttttgtaatt tcgtgtcgtt tctattatga atttcattta    7260
taaagtttat gtacaaatat cataaaaaaa gagaatcttt ttaagcaagg attttcttaa    7320
cttcttcggc gacagcatca ccgacttcgg tggtactgtt ggaaccacct aaatcaccag    7380
ttctgatacc tgcatccaaa accttttaa ctgcatcttc aatggcctta ccttcttcag     7440
gcaagttcaa tgacaatttc aacatcattg cagcagacaa gatagtggcg atagggtcaa    7500
```

```
ccttattctt tggcaaatct ggagcagaac cgtggcatgg ttcgtacaaa ccaaatgcgg    7560
tgttcttgtc tggcaaagag gccaaggacg cagatggcaa caaacccaag gaacctggga    7620
taacggaggc ttcatcggag atgatatcac caaacatgtt gctggtgatt ataataccat    7680
ttaggtgggt tgggttctta actaggatca tggcggcaga atcaatcaat tgatgttgaa    7740
ccttcaatgt aggaaattcg ttcttgatgg tttcctccac agttttctc cataatcttg     7800 aagaggccaa acattagct ttatccaagg accaaatagg caatggtggc tcatgttgta     7860
gggccatgaa agcggccatt cttgtgattc tttgcacttc tggaacggtg tattgttcac    7920
tatcccaagc gacaccatca ccatcgtctt cctttctctt accaaagtaa atacctccca    7980
ctaattctct gacaacaacg aagtcagtac ctttagcaaa ttgtggcttg attggagata    8040
agtctaaaag agagtcggat gcaaagttac atggtcttaa gttggcgtac aattgaagtt    8100
ctttacggat ttttagtaaa ccttgttcag gtctaacact acctgtaccc catttaggac    8160
cacccacagc acctaacaaa acggcatcaa ccttcttgga ggcttccagc gcctcatctg    8220
gaagtgggac acctgtagca tcgatagcag caccaccaat taaatgattt tcgaaatcga    8280
acttgacatt ggaacgaaca tcagaaatag cttttaagaac cttaatggct tcggctgtga    8340
tttcttgacc aacgtggtca cctggcaaaa cgacgatctt cttaggggca gacattagaa    8400
tggtatatcc ttgaaatata tatatatatt gctgaaatgt aaaaggtaag aaaagttaga    8460
aagtaagacg attgctaacc acctattgga aaaaacaata ggtccttaaa taatattgtc    8520
aacttcaagt attgtgatgc aagcatttag tcatgaacgc ttctctattc tatatgaaaa    8580
gccggttccg gcctctcacc tttccttttt ctcccaattt ttcagttgaa aaaggtatat    8640
gcgtcaggcg acctctgaaa ttaacaaaaa atttccagtc atcgaatttg attctgtgcg    8700
atagcgcccc tgtgtgttct cgttatgttg aggaaaaaaa taatggttgc taagagattc    8760
gaactcttgc atcttacgat acctgagtat tcccacagtt ggggatctcg actctagcta    8820
gaggatcaat tcgtaatcat ggtcatagct gtttcctgtg tgaaattgtt atccgctcac    8880
aattccacac aacatacgag ccggaagcat aaagtgtaaa gcctggggtg cctaatgagt    8940
gaggtaactc acattaattg cgttgcgctc actgcccgct ttccagtcgg gaaacctgtc    9000
gtgccagctg gattaatgaa tcggccaacg cgcggggaga ggcggtttgc gtattgggcg    9060
ctcttccgct tcctcgctca ctgactcgct gcgctcggtc gttcggctgc ggcgagcggt    9120
atcagctcac tcaaaggcgg taatacggtt atccacagaa tcaggggata acgcaggaaa    9180
gaacatgtga gcaaaaggcc agcaaaaggc caggaaccgt aaaaaggccg cgttgctggc    9240
gtttttccat aggctccgcc cccctgacga gcatcacaaa aatcgacgct caagtcagag    9300
gtggcgaaac ccgacaggac tataaagata ccaggcgttt ccccctggaa gctccctcgt    9360
gcgctctcct gttccgaccc tgccgcttac cggatacctg tccgcctttc tcccttcggg    9420
aagcgtggcg ctttctcata gctcacgctg taggtatctc agttcggtgt aggtcgttcg    9480
ctccaagctg ggctgtgtgc acgaaccccc cgttcagccc gaccgctgcg ccttatccgg    9540
taactatcgt cttgagtcca acccggtaag acacgactta tcgccactgg cagcagccac    9600
tggtaacagg attagcagag cgaggtatgt aggcggtgct acagagttct tgaagtggtg    9660
gcctaactac ggctacacta aaggacagt atttggtatc tgcgctctgc tgaagccagt     9720
taccttcgga aaaagagttg gtagctcttg atccggcaaa caaaccaccg ctggtagcgg    9780
tggttttttt gtttgcaagc agcagattac gcgcagaaaa aaaggatctc aagaagatcc    9840
tttgatcttt tctacggggt ctgacgctca gtggaacgaa aactcacgtt aagggatttt    9900
```

```
ggtcatgaga ttatcaaaaa ggatcttcac ctagatcctt ttaaattaaa aatgaagttt    9960
taaatcaatc taaagtatat atgagtaaac ttggtctgac agttaccaat gcttaatcag   10020
tgaggcacct atctcagcga tctgtctatt tcgttcatcc atagttgcct gactccccgt   10080
cgtgtagata actacgatac gggagggctt accatctggc cccagtgctg caatgatacc   10140
gcgagaccca cgctcaccgg ctccagattt atcagcaata aaccagccag ccggaagggc   10200
cgagcgcaga agtggtcctg caactttatc cgcctccatc cagtctatta attgttgccg   10260
ggaagctaga gtaagtagtt cgccagttaa tagtttgcgc aacgttgttg ccattgctac   10320
aggcatcgtg gtgtcacgct cgtcgtttgg tatggcttca ttcagctccg gttcccaacg   10380
atcaaggcga gttacatgat cccccatgtt gtgcaaaaaa gcggttagct ccttcggtcc   10440
tccgatcgtt gtcagaagta agttggccgc agtgttatca ctcatggtta tggcagcact   10500
gcataattct cttactgtca tgccatccgt aagatgcttt tctgtgactg gtgagtactc   10560
aaccaagtca ttctgagaat agtgtatgcg gcgaccgagt tgctcttgcc cggcgtcaat   10620
acgggataat accgcgccac atagcagaac tttaaaagtg ctcatcattg gaaaacgttc   10680
ttcggggcga aaactctcaa ggatcttacc gctgttgaga tccagttcga tgtaacccac   10740
tcgtgcaccc aactgatctt cagcatcttt tactttcacc agcgtttctg ggtgagcaaa   10800
aacaggaagg caaaatgccg caaaaaaggg aataagggcg acacggaaat gttgaatact   10860
catactcttc cttttcaat attattgaag catttatcag ggttattgtc tcatgagcgg   10920
atacatattt gaatgtattt agaaaaataa acaaataggg gttccgcgca catttccccg   10980
aaaagtgcca cctgacgtct aagaaaccat tattatcatg acattaacct ataaaaatag   11040
gcgtatcacg aggccctttc gtctcgcgcg tttcggtgat gacggtgaaa acctctgaca   11100
catgcagctc ccggagacgg tcacagcttg tctgtaagcg gatgccggga gcagacaagc   11160
ccgtcagggc gcgtcagcgg gtgttggcgg gtgtcggggc tggcttaact atgcggcatc   11220
agagcagatt gtactgagag tgcaccataa cgcatttaag cataaacacg cactatgccg   11280
ttcttctcat gtatatatat atacaggcaa cacgcagata taggtgcgac gtgaacagtg   11340
agctgtatgt gcgcagctcg cgttgcattt tcggaagcgc tcgttttcgg aaacgctttg   11400
aagttcctat tccgaagttc ctattctcta gctagaaagt ataggaactt cagagcgctt   11460
ttgaaaacca aaagcgctct gaagacgcac tttcaaaaaa ccaaaaacgc accggactgt   11520
aacgagctac taaaatattg cgaataccgc ttccacaaac attgctcaaa agtatctctt   11580
tgctatatat ctctgtgcta tatccctata aacctaccc atccacccttt cgctccttga   11640 acttgcatct aaactcgacc tctacatttt ttatgtttat ctctagtatt actctttaga   11700
caaaaaaatt gtagtaagaa ctattcatag agtgaatcga aaacaatacg aaaatgtaaa   11760
catttcctat acgtagtata tagagacaaa atagaagaaa ccgttcataa ttttctgacc   11820
aatgaagaat catcaacgct atcactttct gttcacaaag tatgcgcaat ccacatcggt   11880
atagaatata atcggggatg cctttatctt gaaaaaatgc acccgcagct tcgctagtaa   11940
tcagtaaacg cggaagtgg agtcaggctt tttttatgga agagaaaata gacaccaaag   12000
tagccttctt ctaaccttaa cggacctaca gtgcaaaaag ttatcaagag actgcattat   12060
agagcgcaca aaggagaaaa aaagtaatct aagatgcttt gttagaaaaa tagcgctctc   12120
gggatgcatt tttgtagaac aaaaaagaag tatagattct ttgttggtaa aatagcgctc   12180
tcgcgttgca tttctgttct gtaaaaatgc agctcagatt ctttgtttga aaaattagcg   12240
ctctcgcgtt gcattttgt tttacaaaaa tgaagcacag attcttcgtt ggtaaaatag   12300
```

```
cgctttcgcg ttgcatttct gttctgtaaa aatgcagctc agattctttg tttgaaaaat    12360
tagcgctctc gcgttgcatt tttgttctac aaaatgaagc acagatgctt cgtt          12414

<210> SEQ ID NO 18
<211> LENGTH: 7254
<212> TYPE: DNA
<213> ORGANISM: Artificial sequence
<220> FEATURE:
<223> OTHER INFORMATION: Artificial vector

<400> SEQUENCE: 18
gcttgcatgc aacttctttt cttttttttt cttttctctc tcccccgttg ttgtctcacc      60
atatccgcaa tgacaaaaaa aatgatggaa gacactaaag gaaaaaatta acgacaaaga    120
cagcaccaac agatgtcgtt gttccagagc tgatgagggg tatcttcgaa cacacgaaac    180
ttttttcctt cttcattcac gcacactact ctctaatgag caacggtata cggccttcct    240
tccagttact tgaatttgaa ataaaaaaag tttgccgctt tgctatcaag tataaataga    300
cctgcaatta ttaatctttt gtttcctcgt cattgttctc gttcccttt ttccttgttt     360 cttttttctgc acaatatttc aagctatacc aagcatacaa tcaactccaa gcttgaagca   420
agcctcctga agatgaagc tactgtcttc tatcgaacaa gcatgcgata tttgccgact    480
taaaaagctc aagtgctcca agaaaaaacc gaagtgcgcc aagtgtctga agaacaactg    540
ggagtgtcgc tactctccca aaaccaaaag gtctccgctg actagggcac atctgacaga    600
agtggaatca aggctagaaa gactggaaca gctatttcta ctgattttc ctcgagaaga     660 ccttgacatg atttttgaaaa tggattcttt acaggatata aaagcattgt taacaggatt    720
atttgtacaa gataatgtga ataaagatgc cgtcacagat agattggctt cagtggagac    780
tgatatgcct ctaacattga gacagcatag aataagtgcg acatcatcat cggaagagag    840
tagtaacaaa ggtcaaagac agttgactgt atcgccggaa ttcccgggac agctgcattc    900
tcccatcagc accctgagct cccccatcaa cggcatgggc ccgccttct cggtcatcag     960 ctcccccatg ggccccccact ccatgtcggt gcccaccaca cccaccctgg gcttcagcac   1020
tggcagcccc cagctcagct caccctatgaa ccccgtcagc agcagcgagg acatcaagcc   1080
ccccctgggc ctcaatggcg tcctcaaggt ccccgcccac ccctcaggaa acatggcttc   1140
cttcaccaag cacatctgcg ccatctgcgg ggaccgctcc tcaggcaagc actatggagt   1200
gtacagctgc gaggggtgca agggcttctt caagcggacg gtgcgcaagg acctgaccta   1260
cacctgccgc gacaacaagg actgcctgat tgacaagcgg cagcggaacc ggtgccagta   1320
ctgccgctac cagaagtgcc tggccatggg catgaagcgg gaagccgtgc aggaggagcg   1380
gcagcgtggc aaggaccgga acgagaatga ggtggagtcg accagcagcg ccaacgagga   1440
catgccggtg gagaggatcc tggaggctga gctggccgtg gagcccaaga ccgagaccta   1500
cgtggaggca acatgggcg tgaacccag ctcgccgaac gaccctgtca ccaacatttg     1560
ccaagcagcc gacaaacagc ttttcaccct ggtggagtgg gccaagcgga tcccacactt   1620
ctcagagctg cccctggacg accaggtcat cctgctgcgg gcaggctgga atgagctgct   1680
catcgcctcc ttctcccacc gctccatcgc cgtgaaggac gggatcctcc tggccaccgg   1740
gctgcacgtc caccggaaca gcgcccacag cgcaggggtg ggcgccatct ttgacagggt   1800
gctgacggag cttgtgtcca agatgcggga catgcagatg gacaagacgg agctgggctg   1860
cctgcgcgcc atcgtcctct taacccctga ctccaagggg ctctcgaacc cggccgaggt   1920
ggaggcgctg agggagaagg tctatgcgtc cttggaggcc tactgcaagc acaagtaccc   1980
```

```
agagcagccg ggaaggttcg ctaagctctt gctccgcctg ccggctctgc gctccatcgg    2040
gctcaaatgc ctggaacatc tcttcttctt caagctcatc ggggacacac ccattgacac    2100
cttccttatg gagatgctgg aggcgccgca ccaaatgact taggcctgcg ggcccatcct    2160
ttgtgcccac ccgttctggc caccctgcct ggacgccagc tgttcttctc agcctgagcc    2220
ctgtccctgc ccttctctgc ctggcctgtt tggactttgg ggcacagcct gtcactgctc    2280
tgcctaagag atgtgttgtc accctcctta tttctgttac tacttgtctg tggcccaggg    2340
cagtggcttt cctgagcagc agccttcgtg gcaagaacta gcgtgagccc agccaggcgc    2400
ctccccaccg ggctctcagg acgccctgcc acacccacgg ggcttgggcg actacagggt    2460
cttcggcccc agccctggag ctgcagccaa gctaattccg ggcgaatttc ttatgattta    2520
tgatttttat tattaaataa gttataaaaa aaataagtgt atacaaattt taaagtgact    2580
cttaggtttt aaaacgaaaa ttcttgttct tgagtaactc tttcctgtag gtcaggttgc    2640
tttctcaggt atagcatgag gtcgctctta ttgaccacac ctctaccggc atgccggcaa    2700
gtgcacaaac aatacttaaa taaatactac tcagtaataa cctatttctt agcatttttg    2760
acgaaatttg ctattttgtt agagtctttt acaccatttg tctccacacc tccgcttaca    2820
tcaacaccaa taacgccatt taatctaagc gcatcaccaa cattttctgg cgtcagtcca    2880
ccagctaaca taaatgtaa gctttcgggg ctctcttgcc ttccaaccca gtcagaaatc    2940
gagttccaat ccaaaagttc acctgtccca cctgcttctg aatcaaacaa gggaataaac    3000
gaatgaggtt tctgtgaagc tgcactgagt agtatgttgc agtcttttgg aaatacgagt    3060
cttttaataa ctggccttac tccaaagaca cttcgacgtg actcatcata caacgtcaga    3120
aaacctttat gctcagaaaa ttattgaccg aaaccgagga actcttggta ttcttgccac    3180
gactcatctc catgcagttg gacgatatca atgccgtaat cattgaccag agccaaaaca    3240
tcctccttag gttgattacg aaacacgcca accaagtatt tcggagtgcc tgaactattt    3300
ttatatgctt ttacaagact tgaaattttc cttgcaataa ccgggtcaat tgttctcttt    3360
ctattgggca cacatataat acccagcaag tcagcatcgg aatctagagc acattctgcg    3420
gcctctgtgc tctgcaagcc gcaaactttc accaatggac cagaactacc tgtgaaatta    3480
ataacagaca tactccaagc tgcctttgtg tgcttaatca cgtatactca cgtgctcaat    3540
agtcaccaat gccctcccct cttggccctct ccttttcttt tttcgaccga attaattcgt    3600
aatcatggtc atagctgttt cctgtgtgaa attgttatcc gctcacaatt ccacacaaca    3660
tacgagccgg aagcataaag tgtaaagcct ggggtgccta atgagtgagg taactcacat    3720
taattgcgtt gcgctcactg cccgctttcc agtcgggaaa cctgtcgtgc cagctggatt    3780
aatgaatcgg ccaacgcgcg gggagaggcg gtttgcgtat tgggcgctct tccgcttcct    3840
cgctcactga ctcgctgcgc tcggtcgttc ggctgcggcg agcggtatca gctcactcaa    3900
aggcggtaat acggttatcc acagaatcag gggataacgc aggaaagaac atgtgagcaa    3960
aaggccagca aaaggccagg aaccgtaaaa aggccgcgtt gctggcgttt ttccataggc    4020
tccgcccccc tgacgagcat cacaaaaatc gacgctcaag tcagaggtgg cgaaacccga    4080
caggactata aagataccag gcgtttcccc ctggaagctc cctcgtgcgc tctcctgttc    4140
cgaccctgcc gcttaccgga tacctgtccg cctttctccc ttcgggaagc gtggcgcttt    4200
ctcatagctc acgctgtagg tatctcagtt cggtgtaggt cgttcgctcc aagctgggct    4260
gtgtgcacga accccccgtt cagcccgacc gctgcgcctt atccggtaac tatcgtcttg    4320
agtccaaccc ggtaagacac gacttatcgc cactggcagc agccactggt aacaggatta    4380
```

```
gcagagcgag gtatgtaggc ggtgctacag agttcttgaa gtggtggcct aactacggct   4440
acactagaag gacagtattt ggtatctgcg ctctgctgaa gccagttacc ttcggaaaaa   4500
gagttggtag ctcttgatcc ggcaaacaaa ccaccgctgg tagcggtggt ttttttgttt   4560
gcaagcagca gattacgcgc agaaaaaaag gatctcaaga agatcctttg atctttcta   4620 cggggtctga cgctcagtgg aacgaaaact cacgttaagg gattttggtc atgagattat   4680
caaaaaggat cttcacctag atccttttaa attaaaaatg aagttttaaa tcaatctaaa   4740
gtatatatga gtaaacttgg tctgacagtt accaatgctt aatcagtgag gcacctatct   4800
cagcgatctg tctatttcgt tcatccatag ttgcctgact ccccgtcgtg tagataacta   4860
cgatacggga gggcttacca tctggcccca gtgctgcaat gataccgcga gacccacgct   4920
caccggctcc agatttatca gcaataaacc agccagccgg aagggccgag cgcagaagtg   4980
gtcctgcaac tttatccgcc tccatccagt ctattaattg ttgccgggaa gctagagtaa   5040
gtagttcgcc agttaatagt ttgcgcaacg ttgttgccat tgctacaggc atcgtggtgt   5100
cacgctcgtc gtttggtatg gcttcattca gctccggttc ccaacgatca aggcgagtta   5160
catgatcccc catgttgtgc aaaaaagcgg ttagctcctt cggtcctccg atcgttgtca   5220
gaagtaagtt ggccgcagtg ttatcactca tggttatggc agcactgcat aattctctta   5280
ctgtcatgcc atccgtaaga tgcttttctg tgactggtga gtactcaacc aagtcattct   5340
gagaatagtg tatgcggcga ccgagttgct cttgcccggc gtcaatacgg gataataccg   5400
cgccacatag cagaacttta aaagtgctca tcattggaaa acgttcttcg ggcgaaaac   5460 tctcaaggat cttaccgctg ttgagatcca gttcgatgta acccactcgt gcacccaact   5520
gatcttcagc atcttttact ttcaccagcg tttctgggtg agcaaaaaca ggaaggcaaa   5580
atgccgcaaa aaagggaata agggcgacac ggaaatgttg aatactcata ctcttccttt   5640
ttcaatatta ttgaagcatt tatcagggtt attgtctcat gagcggatac atatttgaat   5700
gtatttagaa aaataaacaa ataggggttc cgcgcacatt tccccgaaaa gtgccacctg   5760
acgtctaaga aaccattatt atcatgacat taacctataa aaataggcgt atcacgaggc   5820
cctttcgtct cgcgcgtttc ggtgatgacg gtgaaaacct ctgacacatg cagctcccgg   5880
agacggtcac agcttgtctg taagcggatg ccgggagcag acaagcccgt cagggcgcgt   5940
cagcgggtgt tggcgggtgt cggggctggc ttaactatgc ggcatcagag cagattgtac   6000
tgagagtgca ccataacgca tttaagcata aacacgcact atgccgttct tctcatgtat   6060
atatatatac aggcaacacg cagatatagg tgcgacgtga acagtgagct gtatgtgcgc   6120
agctcgcgtt gcattttcgg aagcgctcgt tttcggaaac gctttgaagt tcctattccg   6180
aagttcctat tctctagcta aaagtatag aacttcaga gcgcttttga aaaccaaaag   6240
cgctctgaag acgcactttc aaaaaaccaa aaacgcaccg gactgtaacg agctactaaa   6300
aaacttttgg ttttcgcgag acttctgcgt gaaagttttt tggttttgc gtggcctgac   6360 attgctcgat gatttatatt gcgaataccg cttccacaaa cattgctcaa aagtatctct   6420
ttgctatata tctctgtgct atatcccttat ataacctacc catccacctt tcgctccttg   6480
aacttgcatc taaactcgac ctctacattt tttatgttta tctctagtat tactctttag   6540
acaaaaaaat tgtagtaaga actattcata gagtgaatcg aaaacaatac gaaaatgtaa   6600
acatttccta tacgtagtat atagagacaa aatagaagaa accgttcata attttctgac   6660
caatgaagaa tcatcaacgc tatcactttc tgttcacaaa gtatgcgcaa tccacatcgg   6720
tatagaatat aatcggggat gcctttatct tgaaaaaatg cacccgcagc ttcgctagta   6780
```

```
atcagtaaac gcgggaagtg gagtcaggct tttttatgg aagagaaaat agacaccaaa      6840
gtagccttct tctaacctta acggacctac agtgcaaaaa gttatcaaga gactgcatta      6900
tagagcgcac aaaggagaaa aaaagtaatc taagatgctt tgttagaaaa atagcgctct      6960
cgggatgcat ttttgtagaa caaaaaagaa gtatagattc tttgttggta aaatagcgct      7020
ctcgcgttgc atttctgttc tgtaaaaatg cagctcagat tctttgtttg aaaaattagc      7080
gctctcgcgt tgcattttg ttttacaaaa atgaagcaca gattcttcgt tggtaaaata      7140
gcgctttcgc gttgcatttc tgttctgtaa aatgcagct cagattcttt gtttgaaaaa      7200
ttagcgctct cgcgttgcat ttttgttcta caaaatgaag cacagatgct tcgt            7254
```

<210> SEQ ID NO 19
<211> LENGTH: 12315
<212> TYPE: DNA
<213> ORGANISM: Artificial sequence
<220> FEATURE:
<223> OTHER INFORMATION: Plasmid pGAD-BA-ACTR

<400> SEQUENCE: 19

```
gcttgcatgc aacttctttt cttttttttt cttttctctc tcccccgttg ttgtctcacc        60
atatccgcaa tgacaaaaaa aatgatggaa gacactaaag gaaaaaatta acgacaaaga      120
cagcaccaac agatgtcgtt gttccagagc tgatgagggg tatcttcgaa cacacgaaac      180 ttttccttc cttcattcac gcacactact ctctaatgag caacggtata cggccttcct      240
tccagttact tgaatttgaa ataaaaaaag tttgccgctt tgctatcaag tataaaatga      300
cctgcaatta ttaatctttt gtttcctcgt cattgttctc gttccctttc ttccttgttt      360 cttttttctgc acaatatttc aagctatacc aagcatacaa tcaactccaa gctttgcaaa      420
gatggataaa gcggaattaa ttcccgagcc tccaaaaaag aagagaaagg tcgaattggg      480
taccgccgcc aattttaatc aaagtgggaa tattgctgat agctcattgt ccttcacttt      540
cactaacagt agcaacggtc cgaacctcat aacaactcaa acaaattctc aagcgctttc      600
acaaccaatt gctcctcta acgttcatga taacttcatg aataatgaaa tcacggctag      660
taaaattgat gatggtaata attcaaaacc actgtcacct ggttggacgg accaaactgc      720
gtataacgcg tttggaatca ctacagggat gtttaatacc actacaatgg atgatgtata      780
taactatcta ttcgatgatg aagatacccc accaaaccca aaaaagaga tctttatgag      840 tggattagga gaaaacttgg atccactggc cagtgattca cgaaaacgca aattgccatg      900
tgatactcca ggacaaggtc ttacctgcag tggtgaaaaa cggagacggg agcaggaaag      960
taaatatatt gaagaattgg ctgagctgat atctgccaat cttagtgata ttgacaattt     1020
caatgtcaaa ccagataaat gtgcgatttt aaaggaaaca gtaagacaga tacgtcaaat     1080
aaaagagcaa ggaaaaacta tttccaatga tgatgatgtt caaaaagccg atgtatcttc     1140
tacagggcag ggagttattg ataaagactc cttaggaccg cttttacttc aggcattgga     1200
tggtttccta tttgtggtga atcgagacgg aaacattgta tttgtatcag aaaatgtcac     1260
acaatacctg caatataagc aagaggacct ggttaacaca agtgtttaca atatcttaca     1320
tgaagaagac agaaaggatt tccttaagaa tttaccaaaa tctacagtta atggagtttc     1380
ctggacaaat gagacccaaa gacaaaaaag ccatacattt aattgccgta tgttgatgaa     1440
aacaccacat gatattctgg aagacataaa cgccagtcct gaaatgcgcc agatatga       1500 aacaatgcag tgctttgccc tgtctccagcc acgagctatg atggaggaag ggaagatt     1560 gcaatcttgt atgatctgtg tggcacgccg cattactaca ggagaaagaa catttccatc     1620
```

```
aaaccctgag agctttatta ccagacatga tctttcagga aaggttgtca atatagatac   1680
aaattcactg agatcctcca tgaggcctgg cttttgaagat ataatccgaa ggtgtattca   1740
gagatttttt agtctaaatg atgggcagtc atggtcccag aaacgtcact atcaagaagt   1800
taccagtgat gggatatttt ccccaacagc ttatcttaat ggccatgcag aaaccccagt   1860
atatcgattc tcgttggctg atggaactat agtgactgca cagacaaaaa gcaaactctt   1920
ccgaaatcct gtaacaaatg atcgacatgg cttttgtctca acccacttcc ttcagagaga   1980
acagaatgga tatagaccaa acccaaatcc tgttggacaa gggattagac cacctatggc   2040
tggatgcaac agttcggtag gcggcatgag tatgtcgcca aaccaaggct tacagatgcc   2100
gagcagcagg gcctatggct tggcagaccc tagcaccaca gggcagatga gtggagctag   2160
gtatgggggt tccagtaaca tagcttcatt gaccccctggg ccaggcatgc aatcaccatc   2220
ttcctaccag aacaacaact ataggctcaa catgagtagc ccccacatg ggagtcctgg    2280 tcttgcccca aaccagcaga atatcatgat ttctcctcgt aatcgtggga gtccaaagat   2340
agcctcacat cagttttctc ctgttgcagg tgtgcactct cccatggcat cttctggcaa   2400
tactgggaac cacagcttttt ccagcagctc tctcagtgcc ctgcaagcca tcagtgaagg   2460
tgtggggact tcccttttat ctactctgtc atcaccaggc cccaaattgg ataactctcc   2520
caatatgaat attacccaac caagtaaagt aagcaatcag gattccaaga gtcctctggg   2580
cttttattgc gaccaaaatc cagtggagag ttcaatgtgt cagtcaaata gcagagatca   2640
cctcagtgac aaagaaagta aggagagcag tgttgagggg gcagagaatc aaaggggtcc   2700
tttggaaagc aaaggtcata aaaaattact gcagttactt acctgttctt ctgatgaccg   2760
gggtcattcc tccttgacca actccccccct agattcaagt tgtaaagaat cttctgttag   2820
tgtcaccagc ccctctggag tctcctcctc tacatctgga ggagtatcct ctacatccaa   2880
tatgcatggg tcactgttac aagagaagca ccggattttg cacaagttgc tgcagaatgg   2940
gaattcacca gctgaggtag ccaagattac tgcagaagcc actgggaaag acaccagcag   3000
tataacttct tgtgggggacg gaaatgttgt caagcaggag cagctaagtc ctaagaagaa   3060
ggagaataat gcacttctta gatacctgct ggacagggat gatcctagtg atgcactctc   3120
taaagaacta cagcccccaag tggaaggagt ggataataaa atgagtcagt gcaccagctc   3180
caccattcct agctcaagtc aagagaaaga ccctaaaatt aagacagaga caagtgaaga   3240
gggatctgga gacttggata atctagatgc tattcttggt gatctgacta gttctgactt   3300
ttacaataat tccatatcct caaatggtag tcatctgggg actaagcaac aggtgtttca   3360
aggaactaat tctctgggtt tgaaaagttc acagtctgtg cagtctattc gtcctccata   3420
taaccgagca gtgtctctgg atagccctgt ttctgttggc tcaagtcctc agtaaaaaaa   3480
tatcagtgct ttccccatgt taccaaagca acccatgttg ggtgggaatc caagaatgat   3540
ggatagtcag gaaaattatg gctcaagtat gggagactgg ggcttaccaa actcaaaggc   3600
cggcagaatg gaacctatga attcaaactc catgggaaga ccaggaggag attataatac   3660
ttctttaccc agacctgcac tgggtggctc tattcccaca ttgcctcttc ggtctaatag   3720
cataccaggt gcgagaccag tattgcaaca gcagcagcag atgcttcaaa tgaggcctgg   3780
tgaaatcccc atgggaatgg gggctaatcc ctatggccaa gcagcagcat ctaaccaact   3840
gggttcctgg cccgatggca tgttgtccat ggaacaagtt tctcatggca ctcaaaatag   3900
gcctcttctt aggaattccc tggatgatct tgttgggcca ccttccaacc tggaaggcca   3960
gagtgacgaa agagcattat tggaccagct gcacactctt ctcagcaaca cagatgccac   4020
```

```
aggcctggaa gaaattgaca gagctttggg cattcctgaa cttgtcaatc agggacaggc    4080
attagagccc aaacaggatg cttttccaagg ccaagaagca gcagtaatga tggatcagaa    4140
ggcaggatta tatggacaga catacccagc acaggggcct ccaatgcaag gaggcttttca   4200 tcttcaggga caatcaccat cttttaactc tatgatgaat cagatgaacc agcaaggcaa    4260
ttttcctctc caaggaatgc acccacgagc aacatcatg agaccccgga caaacacccc     4320
caagcaactt agaatgcagc ttcagcagag gctgcagggc cagcagtttt tgaatcagag    4380
ccgacaggca cttgaattga aaatggaaaa ccctactgct ggtggtgctg cggtgatgag    4440
gcctatgatg cagccccagc agggttttct taatgctcaa atggtcgccc aacgcagcag    4500
agagctgcta agtcatcact tccgacaaca gagggtggct atgatgatgc agcagcagca    4560
acagcagcag cagcagcagc agcagcagca acagcaacag caacagcaac agcagcaaca    4620
gcagcaaacc caggccttca gcccacctcc taatgtgact gcttccccca gcatggatgg    4680
gcttttggca ggacccacaa tgccacaagc tcctccgcaa cagttccat atcaaccaaa     4740 ttatggaatg ggacaacaac cagatccagc ctttggtcga gtgtctagtc ctcccaatgc    4800
aatgatgtcg tcaagaatgg gtccctccca gaatcccatg atgcaacacc cgcaggctgc    4860
atccatctat cagtcctcag aaatgaaggg ctggccatca ggaaatttgg ccaggaacag    4920
ctccttttcc cagcagcagt ttgcccacca ggggaatcct gcagtgtata gtatggtgca    4980
catgaatggc agcagtggtc acatgggaca gatgaacatg aaccccatgc ccatgtctgg    5040
catgcctatg ggtcctgatc agaaaatactg ctgacatctc tgcaccagga cctcttaagg   5100
aaaccactgt acaaatgaca ctgcactagg attattggga aggaatcatt gttccaggca    5160
tccatcttgg aagaaaggac cagctttgag ctccatcaag ggtattttaa gtgatgtcat    5220
ttgagcagga ctggatttta agccgaaggg caatatctac gtgttttcc ccctccttc      5280 tgctgtgtat catggtgttc aaaacagaaa tgttttttgg cattccacct cctagggata   5340
taattctgga gacatggagt gttactgatc ataaaacttt tgtgtcactt ttttctgcct    5400
tgctagccaa aatctcttaa atacacgtag gtgggccaga gaacattgga agaatcaaga    5460
gagattagaa tatctggttt ctctagttgc agtattggac aaaagagcata gtcccagcct   5520 tcaggtgtag tagttctgtg ttgacccttt gtccagtgga attggtgatt ctgaattgtc    5580
ctttactaat ggtgttgagt tgctctgtcc ctattatttg ccctaggctt tctcctaatg    5640
aaggttttca tttgccattc atgtcctgta atacttcacc tccaggaact gtcatggatg    5700
tccaaatggc tttgcagaaa ggaaatgaga tgacagtatt taatcgcagc agtagcaaac    5760
ttttcacatg ctaatgtgca gctgagtgca ctttatttaa aaagaatgga taaatgcaat    5820
attcttgagg tcttgaggga atagtgaaac acattcctgg tttttgccta cacttacgtg    5880
ttagacaaga actatgattt ttttttttaa agtactggtg tcacccttg cctatatggt      5940 agagcaataa tgcttttaa aaataaactt ctgaaaaccc aaggccaggt actgcattct     6000
gaatcagaat ctcgcagtgt ttctgtgaat agatttttt gtaaatatga cctttaagat     6060
attgtattat gtaaaatatg tatataccctt ttttgtagg tcacaacaac tcattttttac   6120 agagtttgtg aagctaaata tttaacattg ttgatttcag taagctgtgt ggtgaggcta    6180
ccagtggaag agacatccct tgacttttgt ggcctggggg aggggtagtg caccacagct    6240
tttccttccc caccccccag ccttagatgc ctcgctcttt tcaatctctt aatctaaatg    6300 cttttttaaag agattatttg tttagatgta ggcattttaa ttttttaaaa attcctctac    6360
cagaactaag cactttgtta atttgggggg aagaatagat atgggaaa taaacttaaa       6420
```

-continued

```
aaaaaatcag gaatttaaaa aaaacgagca atttgaagag aatcttttgg attttaagca    6480
gtccgaaata atagcaattc atgggctgtg tgtgtgtgtg tatgtgtgtg tgtgtgtgtg    6540
tatgtttaat tatgttacct tttcatcccc tttaggagcg ttttcagatt ttggttcgta    6600
agacctgaat cccgcggccg ccccgggcgt agatactgaa aaaccccgca agttcacttc    6660
aactgtgcat cgtgcaccat ctcaatttct ttcatttata catcgttttg ccttctttta    6720
tgtaactata ctcctctaag tttcaatctt ggccatgtaa cctctgatct atagaatttt    6780
ttaaatgact agaattaatg cccatctttt ttttggacct aaattcttca tgaaaatata    6840
ttacgagggc ttattcagaa gctttggact tcttcgccag aggtttggtc aagtctccaa    6900
tcaaggttgt cggcttgtct accttgccag aaatttacga aagatggaa aagggtcaaa     6960
tcgttggtag atacgttgtt gacacttcta aataagcgaa tttcttatga tttatgattt    7020
ttattattaa ataagttata aaaaaaataa gtgtatacaa attttaaagt gactcttagg    7080
ttttaaaacg aaaattcttg ttcttgagta actctttcct gtaggtcagg ttgctttctc    7140
aggtatagca tgaggtcgct cttattgacc acacctctac cggcatgccc gaaattcccc    7200
taccctatga acatattcca ttttgtaatt tcgtgtcgtt tctattatga atttcattta    7260
taaagtttat gtacaaatat cataaaaaaa gagaatcttt ttaagcaagg attttcttaa    7320
cttcttcggc gacagcatca ccgacttcgg tggtactgtt ggaaccacct aaatcaccag    7380
ttctgatacc tgcatccaaa acctttttaa ctgcatcttc aatggcctta ccttcttcag    7440
gcaagttcaa tgacaatttc aacatcattg cagcagacaa gatagtggcg atagggtcaa    7500
ccttattctt tggcaaatct ggagcagaac cgtggcatgg ttcgtacaaa ccaaatgcgg    7560
tgttcttgtc tggcaaagag gccaaggacg cagatggcaa caaacccaag gaacctggga    7620
taacggaggc ttcatcggag atgatatcac caaacatgtt gctggtgatt ataataccat    7680
ttaggtgggt tgggttctta actaggatca tggcggcaga atcaatcaat tgatgttgaa    7740
ccttcaatgt aggaaattcg ttcttgatgg tttcctccac agttttctc cataatcttg     7800
aagaggccaa aacattagct ttatccaagg accaaatagg caatggtggc tcatgttgta    7860
gggccatgaa agcggccatt cttgtgattc tttgcacttc tggaacggtg tattgttcac    7920
tatcccaagc gacaccatca ccatcgtctt cctttctctt accaaagtaa atacctccca    7980
ctaattctct gacaacaacg aagtcagtac ctttagcaaa ttgtggcttg attggagata    8040
agtctaaaag agagtcggat gcaaagttac atggtcttaa gttggcgtac aattgaagtt    8100
ctttacggat ttttagtaaa ccttgttcag gtctaacact acctgtaccc catttaggac    8160
cacccacagc acctaacaaa acggcatcaa ccttcttgga ggcttccagc gcctcatctg    8220
gaagtgggac acctgtagca tcgatagcag caccaccaat taaatgattt tcgaaatcga    8280
acttgacatt ggaacgaaca tcagaaatag ctttaagaac cttaatggct tcggctgtga    8340
tttcttgacc aacgtggtca cctggcaaaa cgacgatctt cttaggggca gacattagaa    8400
tggtatatcc ttgaaatata tatatatatt gctgaaatgt aaaaggtaag aaaagttaga    8460
aagtaagacg attgctaacc acctattgga aaaaacaata ggtccttaaa taatattgtc    8520
aacttcaagt attgtgatgc aagcatttag tcatgaacgc ttctctattc tatatgaaaa    8580
gccggttccg gcctctcacc tttccttttt ctcccaattt ttcagttgaa aaaggtatat    8640
gcgtcaggcg acctctgaaa ttaacaaaaa atttccagtc atcgaatttg attctgtgcg    8700
atagcgcccc tgtgtgttct cgttatgttg aggaaaaaaa taatggttgc taagagattc    8760
gaactcttgc atcttacgat acctgagtat tcccacagtt ggggatctcg actctagcta    8820
```

```
gaggatcaat tcgtaatcat ggtcatagct gtttcctgtg tgaaattgtt atccgctcac    8880
aattccacac aacatacgag ccggaagcat aaagtgtaaa gcctggggtg cctaatgagt    8940
gaggtaactc acattaattg cgttgcgctc actgccggat taatgaatcg gccaacgcgc    9000
ggggagaggc ggtttgcgta ttgggcgctc ttccgcttcc tcgctcactg actcgctgcg    9060
ctcggtcgtt cggctgcggc gagcggtatc agctcactca aaggcggtaa tacggttatc    9120
cacagaatca ggggataacg caggaaagaa catgtgagca aaaggccagc aaaaggccag    9180
gaaccgtaaa aaggccgcgt tgctggcgtt tttccatagg ctccgccccc ctgacgagca    9240
tcacaaaaat cgacgctcaa gtcagaggtg gcgaaacccg acaggactat aaagatacca    9300
ggcgtttccc cctggaagct ccctcgtgcg ctctcctgtt ccgaccctgc cgcttaccgg    9360
atacctgtcc gcctttctcc cttcgggaag cgtggcgctt tctcatagct cacgctgtag    9420
gtatctcagt tcggtgtagg tcgttcgctc caagctgggc tgtgtgcacg aaccccccgt    9480
tcagcccgac cgctgcgcct tatccggtaa ctatcgtctt gagtccaacc cggtaagaca    9540
cgacttatcg ccactggcag cagccactgg taacaggatt agcagagcga ggtatgtagg    9600
cggtgctaca gagttcttga agtggtggcc taactacggc tacactagaa ggacagtatt    9660
tggtatctgc gctctgctga agccagttac cttcggaaaa agagttggta gctcttgatc    9720
cggcaaacaa accaccgctg gtagcggtgg ttttttttgtt tgcaagcagc agattacgcg    9780
cagaaaaaaa ggatctcaag aagatccttt gatcttttct acggggtctg acgctcagtg    9840
gaacgaaaac tcacgttaag ggattttggt catgagatta tcaaaaagga tcttaccta    9900 gatccttta aattaaaaat gaagttttaa atcaatctaa agtatatatg agtaaacttg    9960
gtctgacagt taccaatgct taatcagtga ggcacctatc tcagcgatct gtctatttcg   10020
ttcatccata gttgcctgac tccccgtcgt gtagataact acgatacggg agggcttacc   10080
atctggcccc agtgctgcaa tgataccgcg agacccacgc tcaccggctc cagatttatc   10140
agcaataaac cagccagccg gaagggccga gcgcagaagt ggtcctgcaa ctttatccgc   10200
ctccatccag tctattaatt gttgccggga agctagagta agtagttcgc cagttaatag   10260
tttgcgcaac gttgttgcca ttgctacagg catcgtggtg tcacgctcgt cgtttggtat   10320
ggcttcattc agctccggtt cccaacgatc aaggcgagtt acatgatccc ccatgttgtg   10380
caaaaaagcg gttagctcct tcggtcctcc gatcgttgtc agaagtaagt tggccgcagt   10440
gttatcactc atggttatgg cagcactgca taattctctt actgtcatgc catccgtaag   10500
atgcttttct gtgactggtg agtactcaac caagtcattc tgagaatagt gtatgcggcg   10560
accgagttgc tcttgcccgg cgtcaatacg ggataatacc gcgccacata gcagaacttt   10620
aaaagtgctc atcattggaa acgttcttc ggggcgaaaa ctctcaagga tcttaccgct   10680
gttgagatcc agttcgatgt aacccactcg tgcacccaac tgatcttcag catcttttac   10740
tttcaccagc gtttctgggt gagcaaaaac aggaaggcaa aatgccgcaa aaagggaat   10800 aagggcgaca cggaaatgtt gaatactcat actcttcctt tttcaatatt attgaagcat   10860
ttatcagggt tattgtctca tgagcggata catatttgaa tgtatttaga aaataaaca   10920 aatagggtt ccgcgcacat ttccccgaaa agtgccacct gacgtctaag aaaccattat   10980
tatcatgaca ttaacctata aaataggcg tatcacgagg ccctttcgtc tcgcgcgttt   11040
cggtgatgac ggtgaaaacc tctgacacat gcagctcccg gagacggtca cagcttgtct   11100
gtaagcggat gccgggagca gacaagcccg tcagggcgcg tcagcgggtg ttggcgggtg   11160
tcggggctgg cttaactatg cggcatcaga gcagattgta ctgagagtgc accataacgc   11220
```

```
atttaagcat aaacacgcac tatgccgttc ttctcatgta tatatatata caggcaacac    11280
gcagatatag gtgcgacgtg aacagtgagc tgtatgtgcg cagctcgcgt tgcattttcg    11340
gaagcgctcg ttttcggaaa cgctttgaag ttcctattcc gaagttccta ttctctagct    11400
agaaagtata ggaacttcag agcgcttttg aaaccaaaaa gcgctctgaa gacgcacttt    11460
caaaaaacca aaaacgcacc ggactgtaac gagctactaa aatattgcga ataccgcttc    11520
cacaaacatt gctcaaaagt atctctttgc tatatatctc tgtgctatat ccctatataa    11580
cctacccatc caccttctcgc tccttgaact tgcatcctag tattactctt tagacaaaaa    11640
aattgtagta agaactattc atagagtgaa tcgaaaacaa tacgaaaatg taaacatttc    11700
ctatacgtag tatatagaga caaaatagaa gaaaccgttc ataattttct gaccaatgaa    11760
gaatcatcaa cgctatcact ttctgttcac aaagtatgcg caatccacat cggtatagaa    11820
tataatcggg gatgccttta tcttgaaaaa atgcacccgc agcttcgcta gtaatcagta    11880
aacgcgggaa gtggagtcag cttttttta tggaagagaa aatagacacc aaagtagcct    11940
tcttctaacc ttaacggacc tacagtgcaa aaagttatca agagactgca ttatagagcg    12000
cacaaaggag aaaaaagta atctaagatg ctttgttaga aaaatagcgc tctcgggatg    12060 cattttgta gaacaaaaaa gaagtataga ttctttgttg gtaaaatagc gctctcgcgt    12120
tgcatttctg ttctgtaaaa atgcagctca gattctttgt ttgaaaaatt agcgctctcg    12180
cgttgcattt ttgttttaca aaatgaagc acagattctt cgttggtaaa atagcgcttt    12240
cgcgttgcat ttctgttctg taaaaatgca gctcaggcat ttttgttcta caaaatgaag    12300
cacagatgct tcgtt                                                     12315
```

<210> SEQ ID NO 20
<211> LENGTH: 7280
<212> TYPE: DNA
<213> ORGANISM: Artificial sequence
<220> FEATURE:
<223> OTHER INFORMATION: pVDR-wt

<400> SEQUENCE: 20

```
gcttgcatgc aacttctttt cttttttttt cttttctctc tcccccgttg ttgtctcacc      60
atatccgcaa tgacaaaaaa aatgatggaa gacactaaag gaaaaaatta acgacaaaga    120
cagcaccaac agatgtcgtt gttccagagc tgatgagggg tatcttcgaa cacacgaaac    180
ttttttcctt cttcattcac gcacactact ctctaatgag caacggtata cggccttcct    240
tccagttact tgaatttgaa ataaaaaaag tttgccgctt tgctatcaag tataaataga    300
cctgcaatta ttaatctttt gtttcctcgt cattgttctc gttcccttc ttccttgttt    360 ctttttctgc acaatatttc aagctatacc aagcatacaa tcaactccaa gcttgaagca    420
agcctcctga agatgaagc tactgtcttc tatcgaacaa gcatgcgata tttgccgact    480
taaaaagctc aagtgctcca agaaaaaacc gaagtgcgcc aagtgtctga gaacaactg    540 ggagtgtcgc tactctccca aaaccaaaag gtctccgctg actagggcac atctgacaga    600
agtggaatca aggctagaaa gactggaaca gctatttcta ctgattttc ctcgagaaga    660 ccttgacatg attttgaaaa tggattcttt acaggatata aaagcattgt taacaggatt    720
atttgtacaa gataatgtga ataaagatgc cgtcacagat agattggctt cagtggagac    780
tgatatgcct ctaacattga gacagcatag aataagtgcg acatcatcat cggaagagag    840
tagtaacaaa ggtcaaagac agttgactgt atcgccggct agcgaattca tggaggcaat    900
ggcggccagc acttccctgc ctgaccctgg agactttgac cggaacgtgc cccggatctg    960
```

```
tggggtgtgt ggagaccgag ccactggctt tcacttcaat gctatgacct gtgaaggctg    1020
caaaggcttc ttcaggcgaa gcatgaagcg gaaggcacta ttcacctgcc ccttcaacgg    1080
ggactgccgc atcaccaagg acaaccgacg ccactgccag gcctgccggc tcaaacgctg    1140
tgtggacatc ggcatgatga aggagttcat tctgacagat gaggaagtgc agaggaagcg    1200
ggagatgatc ctgaagcgga aggaggagga ggccttgaag acagtctgcg gcccaagct     1260 gtctgaggag cagcagcgca tcattgccat actgctggac ccccaccata agacctacga    1320
ccccacctac tccgacttct gccagttccg gcctccagtt cgtgtgaatg atggtggagg    1380
gagccatcct tccaggccca actccagaca cactcccagc ttctctgggg actcctcctc    1440
ctcctgctca gatcactgta tcacctcttc agacatgatg gactcgtcca gcttctccaa    1500
tctggatctg agtgaagaag attcagatga cccttctgtg accctagagc tgtcccagct    1560
ctccatgctg ccccacctgg ctgacctggt cagttacagc atccaaaagg tcattggctt    1620
tgctaagatg ataccaggat tcagagacct cacctctgag gaccagatcg tactgctgaa    1680
gtcaagtgcc attgaggtca tcatgttgcg ctccaatgag tccttcacca tggacgacat    1740
gtcctggacc tgtggcaacc aagactacaa gtaccgcgtc agtgacgtga ccaaagccgg    1800
acacagcctg gagctgattg agcccctcat caagttccag gtgggactga agaagctgaa    1860
cttgcatgag gaggagcatg tcctgctcat ggccatctgc atcgtctccc cagatcgtcc    1920
tggggtgcag gacgccgcgc tgattgaggc catccaggac cgcctgtcca cacactgca     1980 gacgtacatc cgctgccgcc acccgccccc gggcagccac ctgctctatg ccaagatgat    2040
ccagaagcta gccgacctgc gcagcctcaa tgaggagcac tccaagcagt accgctgcct    2100
ctccttccag cctgagtgca gcatgaagct aacgccccct tgtgctcgaag tgtttggcaa    2160 tgagatctcc tgaactagtc catcctttgt gcccacccgt tctggccacc ctgcctggac    2220
gccagctgtt cttctcagcc tgagcccgt ccctgccctt ctctgcctgg cctgtttgga     2280
cttgggtgca cagcctgtca ctgctctgcc taagagatgt gttgtcaccc tccttatttc    2340
tgttactact tgtctgtggc ccagggcagt ggctttcctg agcagcagcc ttcgtggcaa    2400
gaactagcgt gagcccagcc aggcgcctcc ccaccgggct ctcaggacgc cctgccacac    2460
ccacggggct tgggcgacta cagggtcttc ggccccagcc ctggagctgc agccaagcta    2520
attccgggcg aatttcttat gatttatgat tttattatt  aataagtta  taaaaaaaat    2580 aagtgtatac aaattttaaa gtgactctta ggttttaaaa cgaaaattct tgttcttgag    2640
taactctttc ctgtaggtca ggttgctttc tcaggtatag catgaggtcg ctcttattga    2700
ccacacctct accggcatgc cggcaagtgc acaaacaata cttaaataaa tactactcag    2760
taataaccta tttcttagca tttttgacga aatttgctat tttgttagag tcttttacac    2820
catttgtctc cacacctccg cttacatcaa caccaataac gccatttaat ctaagcgcat    2880
caccaacatt ttctggcgtc agtccaccag ctaacataaa atgtaagctt tcggggctct    2940
cttgccttcc aacccagtca gaaatcgagt tccaatccaa aagttcacct gtcccacctg    3000
cttctgaatc aaacaaggga ataaacgaat gaggtttctg tgaagctgca ctgagtagta    3060
tgttgcagtc ttttggaaat acgagtcttt taataactgg ccttactcca aagacacttc    3120
gacgtgactc atcatacaac gtcagaaaac ctttatgctc agaaaattat tgaccgaaac    3180
cgaggaactc ttggtattct tgccacgact catctccatg cagttggacg atatcaatgc    3240
cgtaatcatt gaccagagcc aaaacatcct cctaggttg attacgaaac acgccaacca     3300
agtatttcgg agtgcctgaa ctatttttat atgctttac aagacttgaa attttccttg     3360
```

```
caataaccgg gtcaattgtt ctctttctat tgggcacaca tataataccc agcaagtcag    3420
catcggaatc tagagcacat tctgcggcct ctgtgctctg caagccgcaa actttcacca    3480
atggaccaga actacctgtg aaattaataa cagacatact ccaagctgcc tttgtgtgct    3540
taatcacgta tactcacgtg ctcaatagtc accaatgccc tccctcttgg ccctctcctt    3600
ttcttttttc gaccgaatta attcgtaatc atggtcatag ctgtttcctg tgtgaaattg    3660
ttatccgctc acaattccac acaacatacg agccggaagc ataaagtgta aagcctgggg    3720
tgcctaatga gtgaggtaac tcacattaat tgcgttgcgc tcactgcccg ctttccagtc    3780
gggaaacctg tcgtgccagc tggattaatg aatcggccaa cgcgcgggga gaggcggttt    3840
gcgtattggg cgctcttccg cttcctcgct cactgactcg ctgcgctcgg tcgttcggct    3900
gcggcgagcg gtatcagctc actcaaaggc ggtaatacgg ttatccacag aatcagggga    3960
taacgcagga agaacatgt gagcaaaagg ccagcaaaag gccaggaacc gtaaaaaggc    4020
cgcgttgctg gcgtttttcc ataggctccg ccccctgac gagcatcaca aaaatcgacg    4080
ctcaagtcag aggtggcgaa acccgacagg actataaaga taccaggcgt ttccccctgg    4140
aagctccctc gtgcgctctc ctgttccgac cctgccgctt accggatacc tgtccgcctt    4200
tctcccttcg ggaagcgtgg cgctttctca tagctcacgc tgtaggtatc tcagttcggt    4260
gtaggtcgtt cgctccaagc tgggctgtgt gcacgaaccc cccgttcagc ccgaccgctg    4320
cgccttatcc ggtaactatc gtcttgagtc caacccggta agacacgact tatcgccact    4380
ggcagcagcc actggtaaca ggattagcag agcgaggtat gtaggcggtg ctacagagtt    4440
cttgaagtgg tggcctaact acggctacac tagaaggaca gtatttggta tctgcgctct    4500
gctgaagcca gttaccttcg gaaaaagagt tggtagctct tgatccggca acaaaccac    4560 cgctggtagc ggtggttttt tgtttgcaa gcagcagatt acgcgcagaa aaaaaggatc    4620
tcaagaagat cctttgatct tttctacggg gtctgacgct cagtggaacg aaaactcacg    4680
ttaagggatt ttggtcatga gattatcaaa aaggatcttc acctagatcc ttttaaatta    4740
aaaatgaagt tttaaatcaa tctaaagtat atatgagtaa acttggtctg acagttacca    4800
atgcttaatc agtgaggcac ctatctcagc gatctgtcta tttcgttcat ccatagttgc    4860
ctgactcccc gtcgtgtaga taactacgat acgggagggc ttaccatctg gccccagtgc    4920
tgcaatgata ccgcgagacc cacgctcacc ggctccagat ttatcagcaa taaaccagcc    4980
agccggaagg gccgagcgca gaagtggtcc tgcaacttta tccgcctcca tccagtctat    5040
taattgttgc cgggaagcta gagtaagtag ttcgccagtt aatagtttgc gcaacgttgt    5100
tgccattgct acaggcatcg tggtgtcacg ctcgtcgttt ggtatggctt cattcagctc    5160
cggttcccaa cgatcaaggc gagttacatg atcccccatg ttgtgcaaaa aagcggttag    5220
ctccttcggt cctccgatcg ttgtcagaag taagttggcc gcagtgttat cactcatggt    5280
tatggcagca ctgcataatt ctcttactgt catgccatcc gtaagatgct tttctgtgac    5340
tggtgagtac tcaaccaagt cattctgaga atagtgtatg cggcgaccga gttgctcttg    5400
cccggcgtca atacgggata ataccgcgcc acatagcaga actttaaaag tgctcatcat    5460
tggaaaacgt tcttcgggc gaaaactctc aaggatctta ccgctgttga tccagttc    5520 gatgtaaccc actcgtgcac ccaactgatc ttcagcatct tttactttca ccagcgtttc    5580
tgggtgagca aaaacaggaa ggcaaaatgc cgcaaaaaag gaataagggc gacacggaa    5640 atgttgaata ctcatactct tccttttca atattattga agcatttatc agggttattg    5700
tctcatgagc ggatacatat ttgaatgtat ttagaaaaat aaacaaatag gggttccgcg    5760
```

```
cacatttccc cgaaaagtgc cacctgacgt ctaagaaacc attattatca tgacattaac    5820
ctataaaaat aggcgtatca cgaggccctt tcgtctcgcg cgtttcggtg atgacggtga    5880
aaacctctga cacatgcagc tcccggagac ggtcacagct tgtctgtaag cggatgccgg    5940
gagcagacaa gcccgtcagg gcgcgtcagc gggtgttggc gggtgtcggg gctggcttaa    6000
ctatgcggca tcagagcaga ttgtactgag agtgcaccat aacgcattta agcataaaca    6060
cgcactatgc cgttcttctc atgtatatat atatacaggc aacacgcaga tataggtgcg    6120
acgtgaacag tgagctgtat gtgcgcagct cgcgttgcat tttcggaagc gctcgttttc    6180
ggaaacgctt tgaagttcct attccgaagt tcctattctc tagctagaaa gtataggaac    6240
ttcagagcgc ttttgaaaac caaaagcgct ctgaagacgc actttcaaaa aaccaaaaac    6300
gcaccggact gtaacgagct actaaaaaac ttttggtttt cgcgagactt ctgcgtgaaa    6360
gttttttggt ttttgcgtgg cctgacattg ctcgatgatt tatattgcga ataccgcttc    6420
cacaaacatt gctcaaaagt atctctttgc tatatatctc tgtgctatat ccctatataa    6480
cctacccatc cacctttcgc tccttgaact tgcatctaaa ctcgacctct acattttta    6540 tgtttatctc tagtattact ctttagacaa aaaaattgta gtaagaacta ttcatagagt    6600
gaatcgaaaa caatacgaaa atgtaaacat ttcctatacg tagtatatag agacaaaata    6660
gaagaaaccg ttcataattt tctgaccaat gaagaatcat caacgctatc actttctgtt    6720
cacaaagtat gcgcaatcca catcggtata gaatataatc ggggatgcct ttatcttgaa    6780
aaaatgcacc cgcagcttcg ctagtaatca gtaaacgcgg gaagtggagt caggcttttt    6840
ttatggaaga gaaaatagac accaaagtag ccttcttcta accttaacgg acctacagtg    6900 caaaagtta tcaagagact gcattataga gcgcacaaag gagaaaaaaa gtaatctaag    6960
atgctttgtt agaaaaatag cgctctcggg atgcattttt gtagaacaaa aagaagtat    7020 agattctttg ttggtaaaat agcgctctcg cgttgcattt ctgttctgta aaatgcagc    7080 tcagattctt tgtttgaaaa attagcgctc tcgcgttgca tttttgtttt acaaaaatga    7140
agcacagatt cttcgttggt aaaatagcgc tttcgcgttg catttctgtt ctgtaaaaat    7200
gcagctcaga ttctttgttt gaaaaattag cgctctcgcg ttgcattttt gttctacaaa    7260
atgaagcaca gatgcttcgt                                               7280
```

<210> SEQ ID NO 21
<211> LENGTH: 7460
<212> TYPE: DNA
<213> ORGANISM: Artificial sequence
<220> FEATURE:
<223> OTHER INFORMATION: Plasmid pS0016

<400> SEQUENCE: 21

```
tacggtcatt ctagagggcc cttcgaaggt aagcctatcc ctaaccctct cctcggtctc      60
gattctacgc gtaccggtca tcatcaccat caccattgag tttaaacccg ctgatcctag     120
agggccgcat catgtaatta gttatgtcac gcttacattc acgccctccc cccacatccg     180
ctctaaccga aaaggaagga gttagacaac ctgaagtcta ggtccctatt tatttttta     240 tagttatgtt agtattaaga acgttattta tatttcaaat ttttcttttt tttctgtaca     300
gacgcgtgta cgcatgtaac attatactga aaaccttgct tgagaaggtt ttgggacgct     360
cgaaggcttt aatttgcaag ctgcggccct gcattaatga atcggccaac gcgcggggag     420
aggcggtttg cgtattgggc gctcttccgc ttcctcgctc actgactcgc tgcgctcggt     480
cgttcggctg cggcgagcgg tatcagctca ctcaaaggcg gtaatacggt tatccacaga     540
```

```
atcagggat  aacgcaggaa  agaacatgtg  agcaaaaggc  cagcaaaagc  ccaggaaccg   600
taaaaaggcc  gcgttgctgg  cgttttttcca  taggctccgc  cccctgacg  agcatcacaa   660 aaatcgatgc  tcaagtcaga  ggtggcgaaa  cccgacagga  ctataaagat  accaggcgtt   720
tccccctgga  agctccctcg  tgcgctctcc  tgttccgacc  ctgccgctta  ccggataacct   780 gtccgccttt  ctcccttcgg  gaagcgtggc  gctttctcat  agctcacgct  gtaggtatct   840
cagttcggtg  taggtcgttc  gctccaagct  gggctgtgtg  cacgaaccc  ccgttcagcc   900 cgaccgctgc  gccttatccg  gtaactatcg  tcttgagtcc  aacccggtaa  gacacgactt   960
atcgccactg  gcagcagcca  ctggtaacag  gattagcaga  gcgaggtatg  taggcggtgc   1020
tacagagttc  ttgaagtggt  ggcctaacta  cggctacact  agaaggacag  tatttggtat   1080
ctgcgctctg  ctgaagccag  ttaccttcgg  aaaagagtt  ggtagctctt  gatccggcaa   1140
acaaaccacc  gctggtagcg  gtggttttt  tgtttgcaag  cagcagatta  cgcgcagaaa   1200
aaaaggatct  caagaagatc  ctttgatctt  ttctacgggg  tctgacgctc  agtggaacga   1260
aaactcacgt  taagggattt  tggtcatgag  attatcaaaa  aggatcttca  cctagatcct   1320
tttaaattaa  aaatgaagtt  ttaaatcaat  ctaaagtata  tatgagtaaa  cttggtctga   1380
cagttaccaa  tgcttaatca  gtgaggcacc  tatctcagcg  atctgtctat  ttcgttcatc   1440
catagttgcc  tgactccccg  tcgtgtagat  aactacgata  cgggagcgct  taccatctgg   1500
ccccagtgct  gcaatgatac  cgcgagaccc  acgctcaccg  gctccagatt  tatcagcaat   1560
aaaccagcca  gccggaaggg  ccgagcgcag  aagtggtcct  gcaactttat  ccgcctccat   1620
ccagtctatt  aattgttgcc  gggaagctag  agtaagtagt  tcgccagtta  atagtttgcg   1680
caacgttgtt  ggcattgcta  caggcatcgt  ggtgtcactc  tcgtcgtttg  gtatggcttc   1740
attcagctcc  ggttcccaac  gatcaaggcg  agttacatga  tccccatgt  tgtgcaaaaa   1800 agcggttagc  tccttcggtc  ctccgatcgt  tgtcagaagt  aagttggccg  cagtgttatc   1860
actcatggtt  atggcagcac  tgcataattc  tcttactgtc  atgccatccg  taagatgctt   1920
ttctgtgact  ggtgagtact  caaccaagtc  attctgagaa  tagtgtatgc  ggcgaccgag   1980
ttgctcttgc  ccggcgtcaa  tacgggataa  tagtgtatca  catagcagaa  ctttaaaagt   2040
gctcatcatt  ggaaaacgtt  cttcggggcg  aaaactctca  aggatcttac  cgctgttgag   2100
atccagttcg  atgtaaccca  ctcgtgcacc  caactgatct  tcagcatctt  ttactttcac   2160
cagcgtttct  gggtgagcaa  aaacaggaag  gcaaaatgcc  gcaaaaaagg  gaataagggc   2220
gacacggaaa  tgttgaatac  tcatactctt  cctttttcaa  tgggtaataa  ctgatataat   2280
taaattgaag  ctctaatttg  tgagtttagt  atacatgcat  ttacttataa  tacagttttt   2340
tagttttgct  ggccgcatct  tctcaaatat  gcttcccagc  ctgcttttct  gtaacgttca   2400
ccctctacct  tagcatccct  tccctttgca  atagtcctc  ttccaacaat  aataatgtca   2460
gatcctgtag  agaccacatc  atccacggtt  ctatactgtt  gacccaatgc  gtctcccttg   2520
tcatctaaac  ccacaccggg  tgtcataatc  aaccaatcgt  aaccttcatc  tcttccaccc   2580
atgtctcttt  gagcaataaa  gccgataaca  aaatctttgt  cgctcttcgc  aatgtcaaca   2640
gtacccttag  tatattctcc  agtagatagg  gagcccttgc  atgacaattc  tgctaacatc   2700
aaaaggcctc  taggttcctt  tgttacttct  tctgccgcct  gcttcaaacc  gctaacaata   2760
cctgggccca  ccacaccgtg  tgcattcgta  atgtctgccc  attctgctat  tctgtataca   2820
cccgcagagt  actgcaattt  gactgtatta  ccaatgtcag  caaattttct  gtcttcgaag   2880
agtaaaaaat  tgtacttggc  ggataatgcc  tttagcggct  taactgtgcc  ctccatggaa   2940
```

```
aaatcagtca agatatccac atgtgttttt agtaaacaaa ttttgggacc taatgcttca    3000
actaactcca gtaattcctt ggtggtacga acatccaatg aagcacacaa gtttgtttgc    3060
ttttcgtgca tgatattaaa tagcttggca gcaacaggac taggatgagt agcagcacgt    3120
tccttatatg tagctttcga catgattttat cttcgtttcc tgcaggtttt tgttctgtgc    3180
agttgggtta agaatactgg gcaatttcat gtttcttcaa cactacatat gcgtatatat    3240
accaatctaa gtctgtgctc cttccttcgt tcttccttct gttcggagat taccgaatca    3300
aaaaaatttc aaagaaaccg aaatcaaaaa aagaataaa aaaaaaatga tgaattgaat    3360
tgaaaagcta gcttatcgat gataagctgt caaagatgag aattaattcc acggactata    3420
gactatacta gatactccgt ctactgtacg atacacttcc gctcaggtcc ttgtcccttta   3480
acgaggcctt accactcttt tgttactcta ttgatccagc tcagcaaagg cagtgtgatc    3540
taagattcta tcttcgcgat gtagtaaaac tagctagacc gagaaagaga ctagaaatgc    3600
aaaaggcact tctacaatgg ctgccatcat tattatccga tgtgacgctg cagcttctca    3660
atgatattcg aatacgcttt gaggagatac agcctaatat ccgacaaact gttttacaga    3720
tttacgatcg tacttgttac ccatcattga attttgaaca tccgaacctg ggagttttcc    3780
ctgaaacaga tagtatattt gaacctgtat aataatatat agtctagcgc tttacggaag    3840
acaatgtatg tatttcggtt cctggagaaa ctattgcatc tattgcatag gtaatcttgc    3900
acgtcgcatc cccggttcat tttctgcgtt tccatcttgc acttcaatag catatctttg    3960
ttaacgaagc atctgtgctt catttttgtag aacaaaaatg caacgcgaga gcgctaattt    4020
ttcaaacaaa gaatctgagc tgcattttta cagaacagaa atgcaacgcg aaagcgctat    4080
tttaccaacg aagaatctgt gcttcatttt tgtaaaacaa aaatgcaacg cgacgagagc    4140
gctaattttt caaacaaaga atctgagctg cattttttaca gaacagaaat gcaacgcgag    4200
agcgctatttt taccaacaaa gaatctatac ttcttttttg ttctacaaaa atgcatcccg    4260
agagcgctat ttttctaaca aagcatctta gattacttttt tttctccttt gtgcgctcta    4320
taatgcagtc tcttgataac tttttgcact gtaggtccgt taaggttaga agaaggctac    4380
tttggtgtct atttctctt ccataaaaaa agcctgactc cacttcccgc gtttactgat    4440
tactagcgaa gctgcgggtg catttttttca agataaaggc atccccgatt atattctata    4500
ccgatgtgga ttgcgcatac tttgtgaaca gaaagtgata gcgttgatga ttcttcattg    4560
gtcagaaaat tatgaacggt ttcttctatt ttgtctctat atactacgta taggaaatgt    4620
ttacattttc gtattgtttt cgattcactc tatgaatagt tcttactaca attttttgt    4680
ctaaagagta atactagaga taaacataaa aaatgtagag gtcgagttta gatgcaagtt    4740
caaggagcga aaggtggatg ggtaggttat atagggatat agcacagaga tatatagcaa    4800
agagatactt ttgagcaatg tttgtggaag cggtattcgc aatgggaagc tccaccccgg    4860
ttgataatca gaaaagcccc aaaaacagga agattgtata agcaaatatt taaattgtaa    4920
acgttaatat tttgttaaaa ttcgcgttaa attttgtta aatcagctca ttttttaacg    4980
aatagcccga atcggcaaa atcccttata aatcaaaaga atagaccgag atagggttga    5040
gtgttgttcc agtttccaac aagagtccac tattaaagaa cgtggactcc aacctcaaag    5100
ggcgaaaaag ggtctatcag ggcgatggcc cactacgtga accatcaccc taatcaagtt    5160
ttttggggtc gaggtgccgt aaagcagtaa atcggaaggg taaacggatg ccccatttta    5220
gagcttgacg gggaaagccg gcgaacgtgg cgagaaagga agggaagaaa gcgaaaggag    5280
cgggggctag ggcggtggga agtgtagggg tcacgctggg cgtaaccacc acacccgccg    5340
```

```
cgcttaatgg ggcgctacag ggcgcgtggg gatgatccac tagtacggat tagaagccgc   5400
cgagcgggtg acagccctcc gaaggaagac tctcctccgt gcgtcctcgt cttcaccggt   5460
cgcgttcctg aaacgcagat gtgcctcgcg ccgcactgct ccgaacaata aagattctac   5520
aatactagct tttatggtta tgaagaggaa aaattggcag taacctggcc ccacaaacct   5580
tcaaatgaac gaatcaaatt aacaaccata ggatgataat gcgattagtt ttttagcctt   5640
atttctgggg taattaatca gcgaagcgat gattttgat ctattaacag atatataaat   5700
gcaaaaactg cataaccact ttaactaata ctttcaacat tttcggtttg tattacttct   5760
tattcaaatg taataaaagt atcaacaaaa aattgttaat atacctctat actttaacgt   5820
caaggagaaa aaccccgga tcggactact agcagctgta atacgactca ctatagggaa   5880
tattaagcta tcaaacaagt ttgtacaaaa aagcaggctt ggaaggagtt cgaaccatga   5940
cccagaccct caagtacgcc tccagagtgt tccatcgcgt ccgctgggcg cccgagttgg   6000
gcgcctccct aggctaccga gagtaccact cagcacgccg gagcttggca gacatcccag   6060
gcccctctac gcccagcttt ctggccgaac ttttctgcaa ggggggctg tcgaggctac   6120 acgagctgca ggtgcagggc gccgcgcact cgggccggt gtggctagcc agcttgggga   6180
cagtgcgcac cgtgtacgtg gctgcccctg cactcgtcga ggagctgctg cgacaggagg   6240
gaccccggcc cgagcgctgc agcttctcgc cctggacgga gcaccgccgc tgccgccagc   6300
gggcttgcgg actgctcact gcggaaggcg aagaatggca aaggctccgc agtctcctgg   6360
ccccgctcct cctccggcct caagcggccg cccgctacgc cggaaccctg aacaacgtag   6420
tctgcgacct tgtgcggcgt ctgaggcgcc agcggggacg tggcacgggg ccgcccgccc   6480
tggttcggga cgtggcgggg gaatttttaca agttcggact ggaaggcatc gccgcggttc   6540
tgctcggctc gcgcttgggc tgcctggagg ctcaagtgcc acccgacacg gagaccttca   6600
tccgcgctgt gggctcggtg tttgtgtcca cgctgttgac catggcgatg ccccactggc   6660
tgcgccacct tgtgcctggg ccctggggcc gcctctgccg agactggac cagatgtttg   6720 catttgctca gaggcacgtg gagcggcgag aggcagaggc agccatgagg aacggaggac   6780
agcccgagaa ggacctggag tctggggcgc acctgaccca cttcctgttc cgggaagagt   6840
tgcctgccca gtccatcctg ggaaatgtga cagagttgct attggcggga gtggacacgg   6900
tgtccaacac gctctcttgg gctctgtatg agctctcccg gcaccccgaa gtccagacag   6960
cactccactc agagatcaca gctgccctga gccctggctc cagtgcctac ccctcagcca   7020
ctgttctgtc ccagctgccc ctgctgaagg cggtggtcaa ggaagtgcta agactgtacc   7080
ctgtggtacc tggaaattct cgtgtcccag acaaagacat tcatgtgggt gactatatta   7140
tccccaaaaa tacgctggtc actctgtgtc actatgccac ttcaagggac cctgcccagt   7200
tcccagagcc aaattctttt cgtccagctc gctggctggg ggagggtccc accccccacc   7260
catttgcatc tcttccctt ggctttggca agcgcagctg tatggggaga cgcctggcag   7320
agcttgaatt gcaaatggct ttggcccaga tcctaacaca ttttgaggtg cagcctgagc   7380
caggtgcggc cccagttaga cccaagaccc ggactgtcct ggtacctgaa aggagcatca   7440
acctacagtt tttggacaga                                              7460
```

<210> SEQ ID NO 22
<211> LENGTH: 7458
<212> TYPE: DNA
<213> ORGANISM: Artificial sequence
<220> FEATURE:
<223> OTHER INFORMATION: Plasmid pY2653

<400> SEQUENCE: 22

```
cccagctttc ttgtacaaag tggttcgatc tagagggccc ttcgaaggta agcctatccc      60
taaccctctc ctcggtctcg attctacgcg taccggtcat catcaccatc accattgagt     120
ttaaacccgc tgatcctaga gggccgcatc atgtaattag ttatgtcacg cttacattca     180
cgccctcccc ccacatccgc tctaaccgaa aaggaaggag ttagacaacc tgaagtctag     240
gtccctattt attttttttat agttatgtta gtattaagaa cgttatttat atttcaaatt    300
tttcttttttt ttctgtacag acgcgtgtac gcatgtaaca ttatactgaa aaccttgctt   360
gagaaggttt tgggacgctc gaaggcttta atttgcaagc tgcggccctg cattaatgaa     420
tcggccaacg cgcggggaga ggcggtttgc gtattgggcg ctcttccgct tcctcgctca     480
ctgactcgct gcgctcggtc gttcggctgc ggcgagcggt atcagctcac tcaaaggcgg     540
taatacggtt atccacagaa tcaggggata acgcaggaaa gaacatgtga gcaaaaggcc     600
agcaaaagcc caggaaccgt aaaaaggccg cgttgctggc gttttttccat aggctccgcc    660
ccccctgacga gcatcacaaa aatcgacgct caagtcagag gtggcgaaac ccgacaggac    720
tataaagata ccaggcgttt ccccctggaa gctccctcgt gcgctctcct gttccgaccc     780
tgccgcttac cggatacctg tccgcctttc tcccttcggg aagcgtggcg ctttctcata     840
gctcacgctg taggtatctc agttcggtgt aggtcgttcg ctccaagctg ggctgtgtgc     900
acgaaccccc cgttcagccc gaccgctgcg ccttatccgg taactatcgt cttgagtcca     960
acccggtaag acacgactta tcgccactgg cagcagccac tggtaacagg attagcagag    1020
cgaggtatgt aggcggtgct acagagttct tgaagtggtg gcctaactac ggctacacta    1080
gaaggacagt atttggtatc tgcgctctgc tgaagccagt taccttcgga aaaagagttg    1140
gtagctcttg atccggcaaa caaccaccg ctggtagcgg tggtttttttt gtttgcaagc    1200
agcagattac gcgcagaaaa aaggatctc aagaagatcc tttgatcttt tctacggggt    1260
ctgacgctca gtggaacgaa aactcacgtt aagggatttt ggtcatgaga ttatcaaaaa    1320
ggatcttcac ctagatcctt ttaaattaaa aatgaagttt taaatcaatc taaagtatat    1380
atgagtaaac ttggtctgac agttaccaat gcttaatcag tgaggcacct atctcagcga    1440
tctgtctatt tcgttcatcc atagttgcct gactccccgt cgtgtagata actacgatac    1500
gggagcgctt accatctggc cccagtgctg caatgatacc gcgagaccca cgctcaccgg    1560
ctccagattt atcagcaata aaccagccag ccggaagggc cgagcgcaga agtggtcctg    1620
caactttatc cgcctccatc cagtctatta attgttgccg gaagctaga gtaagtagtt    1680
cgccagttaa tagtttgcgc aacgttgttg gcattgctac aggcatcgtg gtgtcactct    1740
cgtcgtttgg tatggcttca ttcagctccg gttcccaacg atcaaggcga gttacatgat    1800
cccccatgtt gtgcaaaaaa gcggttagct ccttcggtcc tccgatcgtt gtcagaagta    1860
agttggccgc agtgttatca ctcatggtta tggcagcact gcataattct cttactgtca    1920
tgccatccgt aagatgcttt tctgtgactg gtgagtactc aaccaagtca ttctgagaat    1980
agtgtatgcg gcgaccgagt tgctcttgcc cggcgtcaat acgggataat agtgtatcac    2040
atagcagaac tttaaaagtg ctcatcattg gaaaacgttc ttcggggcga aaactctcaa    2100
ggatcttacc gctgttgaga tccagttcga tgtaacccac tcgtgcaccc aactgatctt    2160
cagcatcttt tactttcacc agcgtttctg ggtgagcaaa aacaggaagg caaaatgccg    2220
caaaaaaggg aataagggcg acacggaaat gttgaatact catactcttc cttttttcaat   2280
gggtaataac tgatataatt aaattgaagc tctaatttgt gagtttagta tacatgcatt    2340
```

```
tacttataat acagttttt  agttttgctg gccgcatctt ctcaaatatg cttcccagcc    2400
tgcttttctg taacgttcac cctctacctt agcatccctt ccctttgcaa atagtcctct    2460
tccaacaata ataatgtcag atcctgtaga gaccacatca tccacggttc tatactgttg    2520
acccaatgcg tctcccttgt catctaaacc cacaccgggt gtcataatca accaatcgta    2580
accttcatct cttccaccca tgtctctttg agcaataaag ccgataacaa atctttgtc     2640 gctcttcgca atgtcaacag tacccttagt atattctcca gtagataggg agcccttgca    2700
tgacaattct gctaacatca aaaggcctct aggttccttt gttacttctt ctgccgcctg    2760
cttcaaaccg ctaacaatac ctgggcccac cacaccgtgt gcattcgtaa tgtctgccca    2820
ttctgctatt ctgtatacac ccgcagagta ctgcaatttg actgtattac caatgtcagc    2880 aaatttctg  tcttcgaaga gtaaaaaatt gtacttggcg ataatgcct  ttagcggctt    2940 aactgtgccc tccatggaaa atcagtcaa  gatatccaca tgtgttttta gtaaacaaat    3000
tttgggacct aatgcttcaa ctaactccag taattccttg gtggtacgaa catccaatga    3060
agcacacaag tttgtttgct tttcgtgcat gatattaaat agcttggcag caacaggact    3120
aggatgagta gcagcacgtt ccttatatgt agctttcgac atgatttatc ttcgtttcct    3180
gcaggttttt gttctgtgca gttgggttaa gaatactggg caatttcatg tttcttcaac    3240
actacatatg cgtatatata ccaatctaag tctgtgctcc ttccttcgtt cttccttctg    3300
ttcggagatt accgaatcaa aaaaatttca agaaaccga  aatcaaaaaa aagaataaaa    3360
aaaaaatgat gaattgaatt gaaaagctag cttatcgatg ataagctgtc aaagatgaga    3420
attaattcca cggactatag actatactag atactccgtc tactgtacga tacacttccg    3480
ctcaggtcct tgtcctttaa cgaggcctta ccactctttt gttactctat tgatccagct    3540
cagcaaaggc agtgtgatct aagattctat cttcgcgatg tagtaaaact agctagaccg    3600
agaaagagac tagaaatgca aaaggcactt ctacaatggc tgccatcatt attatccgat    3660
gtgacgctgc agcttctcaa tgatattcga atacgctttg aggagataca gcctaatatc    3720
cgacaaactg ttttacagat ttacgatcgt acttgttacc catcattgaa ttttgaacat    3780
ccgaacctgg gagttttccc tgaaacagat agtatatttg aacctgtata ataatatata    3840
gtctagcgct ttacggaaga caatgtatgt atttcggttc ctggagaaac tattgcatct    3900
attgcatagg taatcttgca cgtcgcatcc ccggttcatt ttctgcgttt ccatcttgca    3960
cttcaatagc atatctttgt taacgaagca tctgtgcttc attttgtaga acaaaaatgc    4020
aacgcgagag cgctaatttt tcaaacaaag aatctgagct gcatttttac agaacagaaa    4080
tgcaacgcga agcgctatt  ttaccaacga agaatctgtg cttcattttt gtaaaacaaa    4140
aatgcaacgc gacgagagcg ctaattttc  aaacaaagaa tctgagctgc attttttacag   4200 aacagaaatg caacgcgaga gcgctatttt accaacaaag aatctatact tctttttgt    4260 tctacaaaaa tgcatcccga gagcgctatt tttctaacaa agcatcttag attacttttt    4320
ttctcctttg tgcgctctat aatgcagtct cttgataact ttttgcactg taggtccgtt    4380
aaggttagaa gaaggctact tggtgtctta ttttctcttc cataaaaaaa gcctgactcc    4440
acttcccgcg tttactgatt actagcgaag ctgcgggtgc attttttcaa gataaaggca    4500
tccccgatta tattctatac cgatgtggat tgcgcatact tgtgaacag  aaagtgatag    4560 cgttgatgat tcttcattgg tcagaaaatt atgaacggtt tcttctattt tgtctctata    4620
tactacgtat aggaaatgtt tacattttcg tattgtttc  gattcactct atgaatagtt    4680
cttactacaa tttttttgtc taaagagtaa tactagagat aaacataaaa aatgtagagg    4740
```

```
tcgagtttag atgcaagttc aaggagcgaa aggtggatgg gtaggttata tagggatata   4800
gcacagagat atatagcaaa gagatacttt tgagcaatgt tgtggaagc ggtattcgca    4860 atgggaagct ccaccccggt tgataatcag aaaagcccca aaaacaggaa gattgtataa   4920
gcaaatattt aaattgtaaa cgttaatatt ttgttaaaat tcgcgttaaa tttttgttaa   4980
atcagctcat tttttaacga atagcccgaa atcggcaaaa tcccttataa atcaaaagaa   5040
tagaccgaga tagggttgag tgttgttcca gtttccaaca agagtccact attaaagaac   5100
gtggactcca acgtcaaagg gcgaaaaagg gtctatcagg gcgatggccc actacgtgaa   5160
ccatcaccct aatcaagttt tttggggtcg aggtgccgta aagcagtaaa tcggaagggt   5220
aaacggatgc ccccatttag agcttgacgg ggaaagccgg cgaacgtggc gagaaaggaa   5280
gggaagaaag cgaaaggagc gggggctagg gcggtgggaa gtgtaggggt cacgctgggc   5340
gtaaccacca cacccgccgc gcttaatggg gcgctacagg gcgcgtgggg atgatccact   5400
agtacggatt agaagccgcc gagcgggtga cagccctccg aaggaagact ctcctccgtg   5460
cgtcctcgtc ttcaccggtc gcgttcctga aacgcagatg tgcctcgcgc cgcactgctc   5520
cgaacaataa agattctaca atactagctt ttatggttat gaagaggaaa aattggcagt   5580
aacctggccc cacaaacctt caaatgaacg aatcaaatta acaaccatag gatgataatg   5640
cgattagttt tttagcctta tttctggggt aattaatcag cgaagcgatg attttttgatc   5700 tattaacaga tatataaatg caaaaactgc ataaccactt taactaatac tttcaacatt   5760 ttcggttttgt attacttctt attcaaatgt aataaaagta tcaacaaaaa attgttaata   5820
tacctctata ctttaacgtc aaggagaaaa accccggat cggactacta gcagctgtaa    5880
tacgactcac tatagggaat attaagctat caattcgaag gaattcggta ccatgtggaa   5940
gctttggaga gctgaagagg gcgcggcggc gctcggcggc gcgctcttcc tgctgctctt   6000
cgcgctaggg gtccgccagc tgctgaagca gaggcggccg atgggcttcc ccccggggcc   6060 gccgggctg ccatttatcg gcaacatcta ttccctggca gcctcatccg agcttccccca    6120 tgtctacatg agaaagcaga gccaggtgta cggagagatc ttcagtttag atcttggagg   6180
catatcaact gtggttctaa atggctatga tgtagtaaag gaatgccttg ttcatcaaag   6240
cgaaattttt gcagacagac catgccttcc tttattcatg aagatgacaa aaatgggagg   6300
cttactcaat tccagatatg gccgaggatg ggttgatcac agacgattag ctgtaaacag   6360
ttttcgatat tttggatatg gccaaaagtc ttttgaatct aaaatcttgg aagaaaccaa   6420 attttttcaat gatgctattg aaacatacaa aggtagacct tttgacttta aacagttaat   6480
aacgaatgct gtttcaaaca taaccaatct gatcattttt ggagaacgat tcacttatga   6540
agacaccgat tttcagcaca tgattgagtt atttagtgaa aatgtggaac tagctgccag   6600
tgcctcagtc ttcttgtata atgccttttcc atggattggc atcctgcctt ttggaaaaca   6660
tcaacagctg tttagaaatg cagctgtagt ctatgatttt ctctccagac tcattgaaaa   6720
agcttcagtc aacagaaagc ctcagctacc tcagcatttt gttgatgctt atttagatga   6780
gatggatcaa ggtaaaaatg acccatcatc tacttctcc aaagaaaacc taattttctc     6840
agtgggtgaa ctcatcattg ctggaactga aactacaacc aatgtgctac ggtgggcgat   6900
tcttttcatg gcccttttatc ctaatattca aggacaagtt cagaaagaga ttgatttaat   6960
tatgggccct aatgggaagc cttcttggga cgacaaatgc aaaatgcctt atactgaggc   7020
agttttgcat gaagttttaa gattctgtaa tatagttcca ttagggatttt tccatgcaac   7080 ctctgaagat gcagttgtac gtggttattc cattcctaaa ggcacaacag taattacaaa   7140
```

-continued

```
tctttattct gtacactttg atgaaaagta ctggagagac ccagaagtgt tccatcctga    7200
gcgatttctg gacagcagtg gatattttgc caagaaggaa gctttggttc cttttccct    7260 aggaagaaga cattgtcttg gagaacactt ggctcggatg gaaatgttct tgttttttac    7320
agcattgctt cagaggtttc atttgcattt tccacatgaa ctagttccag atctgaagcc    7380
caggttaggc atgacattgc agccccaacc ctacctcatc tgtgctgaaa gacgctacag    7440
acgcccgggc gatcgcga                                                  7458
```

ENGINEERING ENZYMES THROUGH GENETIC SELECTION

CROSS-REFERENCED TO RELATED APPLICATIONS

This application is a continuation-in-part of and claims benefit of and priority to pending U.S. patent application Ser. No. 10/579,683 filed on May 17, 2006. This application also claims benefit of and priority to U.S. Provisional Patent Application No. 60/520,754 filed on Nov. 17, 2003, U.S. Provisional Patent Application No. 60/520,813, also filed on Nov. 17, 2003, and U.S. Provisional Patent Application No. 60/619,671 filed on Oct. 18, 2004, and where permissible, each of which is incorporated by reference in their entirety.

STATEMENT REGARDING FEDERALLY SPONSORED RESEARCH OR DEVELOPMENT

This invention was made in part with government support under grant nos. NIH AI064817 and NIH GM075832 award by the National Institutes of Health. The government has certain rights in this invention.

SEQUENCE LISTING

The present disclosure includes a sequence listing incorporated herein by reference in its entirety.

FIELD OF THE DISCLOSURE

Aspects of the present disclosure are generally directed to systems and methods for generating ligand-receptor pairs for transcriptional control by small molecules.

BACKGROUND

Directed molecular evolution of enzymes is a developing field in the biotechnology industry and occurs through the single or repeated application of two steps: diversity/library generation followed by screening or selecting for function. The last several years have produced much progress in each of these areas. Techniques of diversity generation in the creation of libraries range from methods with no structure/function prejudice (error-prone PCR; mutator strains) to highly focused randomization based on structural information (site-directed mutagenesis; cassette mutagenesis). DNA recombination (DNA-shuffling, StEP, SCRATCHY, RACHITT, RDA-PCR) requires no structural information but works on the premise that Nature has already solved the problem of creating functional proteins from amino acids. By randomly recombining the genes for related proteins, new combinations of the different solutions are created which may be better than any of the original individual proteins. Structure-based approaches can be combined with other methods to generate greater diversity.

Advances have also been made in screening the generated libraries for proteins with desired properties. In a screen each protein in the library is analyzed for function, which limits library size. In contrast, genetic selection evaluates entire libraries at once, in a highly parallel fashion, because only functional members of the library survive the selective pressure. In selection, nonfunctional members of the library are not individually evaluated. For screens, each variant must be individually assayed and the data evaluated, requiring more time and materials. In vivo genetic selection strategies enable the exhaustive analysis of protein libraries with up to about $10^{10}$ different members. The quoted throughputs are maximal values for industrial, robot driven laboratories. Realistically, experience indicates that an academic, individual investigator laboratory can achieve up to $10^4$ samples/day for screening in yeast and $10^7$ samples/day for genetic selection in yeast. In summary, genetic selection is generally preferable to screening not only because it is higher throughput, but also because it requires less time and materials.

With regard to selection, there are several common conventional selection strategies, such as (i) antibiotic resistance, (ii) substrate selected growth, where degradation of substrates provides elements essential for growth (such as C, N, P, and S), iii) auxotrophic complementation to restore metabolic function, and iv) phage display, which displays peptides or proteins on a virus surface and segregates them on the basis of binding affinity. Although powerful, these selection strategies are not general enough to apply to engineering enzymes for many interesting reactions. Conventional systems rely on screening techniques rather than selection techniques because selections are more difficult.

The generation of libraries has spawned many companies, in fact, spawned an industry. What has so far failed to be addressed is a general method of evaluating libraries (no matter how they are generated) through genetic selection. Accordingly, there is a need for new compositions and methods for engineering polypeptides and rapidly identifying engineered polypeptides having desirable characteristics.

SUMMARY

The embodiments of the present disclosure provide a versatile system, and methods of using, that allow for the selection of variant nuclear receptor ligand binding domains, or for the selection of variant enzymes, or combinations thereof, that may have an enhanced ability to synthesize a nuclear receptor ligand or a precursor thereof.

One aspect of the present disclosure, therefore, encompasses embodiments of a yeast cell comprising: (i) a yeast transcription modulating system comprising a first heterologous nucleic acid expression system encoding a recombinant nuclear receptor polypeptide comprising a ligand-binding domain operably linked to a DNA-binding domain and optionally to a flexible hinge domain, where the recombinant nuclear receptor polypeptide, when it is expressed in the yeast cell in the presence of a nuclear receptor ligand, specifically binds to the recombinant nuclear receptor polypeptide, thereby activating expression of a selective genetic locus; and a second heterologous nucleic acid expression system encoding an adapter polypeptide comprising a coactivator domain operably linked to a yeast transcriptional activator, and where the first heterologous nucleic acid expression system and the first heterologous nucleic acid expression system are each independently encoded by individual heterologous polynucleotides or are encoded by the same heterologous polynucleotide; (ii) a nuclear receptor ligand generating system comprising a third heterologous nucleic acid expression system encoding a heterologous enzyme system for the generation of a nuclear receptor ligand from a substrate, where the nuclear receptor ligand is characterized as specifically binding to the recombinant nuclear receptor polypeptide; and (iii) a selective genetic locus expressed in the presence of the recombinant nuclear receptor polypeptide and a nuclear receptor ligand specifically bound to the recombinant nuclear receptor polypeptide.

In embodiments of this aspect of the disclosure, the coregulator domain can be SRC-1 or ACTR.

In embodiments of this aspect of the disclosure, the third heterologous nucleic acid expression system may comprise a heterologous polynucleotide encoding a heterologous polypeptide, said heterologous polypeptide having an enzymic activity characterized as generating a candidate nuclear receptor ligand from a substrate.

In other embodiments of this aspect of the disclosure, the third heterologous nucleic acid expression system may comprise a heterologous polynucleotide encoding a plurality of heterologous polypeptides, where said heterologous polypeptides cooperate to generate a candidate nuclear receptor ligand from a substrate.

In yet other embodiments of this aspect of the disclosure, the third heterologous nucleic acid expression system may comprise a plurality of heterologous polynucleotides encoding a plurality of heterologous polypeptides, where said heterologous polypeptides cooperate to generate a candidate nuclear receptor ligand from a substrate.

In embodiments of this aspect of the disclosure, the ligand-binding domain of the recombinant nuclear receptor polypeptide can be derived from a ligand-binding domain of a human nuclear receptor polypeptide, or a variant thereof.

In embodiments of this aspect of the disclosure, the coactivator domain of the adapter polypeptide can be derived from a coactivator domain of a human coactivator, or a variant thereof, where the coactivator binds to the ligand-binding domain of the recombinant nuclear receptor polypeptide in the presence of a ligand to activate expression of a genetic locus.

In embodiments of this aspect of the disclosure, expression of the genetic locus can allows proliferation of the yeast cell on a selective medium.

In embodiments of this aspect of the disclosure, expression of the genetic locus can inhibit proliferation of the yeast cell on a selective medium.

In embodiments of this aspect of the disclosure, the heterologous enzyme system for the generation of a nuclear receptor ligand from a substrate can comprise a modified enzyme, where the modified enzyme catalyzes the formation of a receptor ligand characterized as binding to the recombinant receptor polypeptide.

In some embodiments of this aspect of the disclosure, the heterologous enzyme system for the generation of a nuclear receptor ligand from a substrate comprises vitamin $D_3$ 25-hydroxylase and 25-hydroxyvitamin $D_3$ 1α-hydroxylase, wherein said heterologous enzyme system catalyzes the formation of 1α,25-dihydroxyvitamin $D_3$, and wherein the 1α,25-dihydroxyvitamin $D_3$ binds to the recombinant nuclear receptor polypeptide comprising the ligand-binding domain of a vitamin D receptor, thereby inducing expression of a genetic locus allowing the yeast cell to proliferate on a culture medium not having histidine therein.

Another aspect of the present disclosure provides methods of modulating the transcription of a gene of a yeast cell, the methods comprising (1) providing a yeast cell or population of yeast cells, wherein said yeast cell or population of yeast cells comprises: (i) a yeast transcription modulating system comprising a first heterologous nucleic acid expression system encoding a recombinant nuclear receptor polypeptide comprising a ligand-binding domain operably linked to a DNA-binding domain and optionally to a flexible hinge domain, where the recombinant nuclear receptor polypeptide, when expressed in the yeast cell in the presence of a nuclear receptor ligand specifically binding to the recombinant nuclear receptor polypeptide, activates expression of a genetic locus; and a second heterologous nucleic acid expression system encoding an adapter polypeptide, comprising a coactivator domain operably linked to a yeast transcriptional activator, and wherein the first heterologous nucleic acid expression system and the second heterologous nucleic acid expression system are each independently encoded by individual heterologous polynucleotides or are encoded by the same heterologous polynucleotide; (ii) a nuclear receptor ligand generating system comprising a third heterologous nucleic acid expression system encoding a heterologous enzyme system for the generation of a nuclear receptor ligand from a substrate, wherein the nuclear receptor ligand is characterized as specifically binding to the recombinant nuclear receptor polypeptide; and (iii) a selective yeast genetic locus expressed in the presence of the recombinant nuclear receptor polypeptide and a nuclear receptor ligand specifically bound to the recombinant nuclear receptor polypeptide; and (2) culturing the yeast cell under conditions allowing the yeast cell to synthesize a nuclear receptor ligand from a substrate, whereupon the nuclear receptor ligand specifically binds to the recombinant nuclear receptor polypeptide, thereby inducing transcription of the selective yeast genetic locus.

In some embodiments of this aspect of the disclosure, the step of providing a yeast cell or population of yeast cells may comprise delivering to a yeast cell or population of yeast cells a plurality of third heterologous nucleic acid expression systems encoding a plurality of enzyme systems suspected of generating from a substrate a nuclear receptor ligand specifically binding the recombinant nuclear receptor polypeptide, and where the step of culturing the yeast cell under conditions allowing the yeast cell to synthesize a nuclear receptor ligand from a substrate identifies a third heterologous nucleic acid expression system encoding an enzyme system generating the nuclear receptor ligand.

In embodiments of this aspect of the disclosure, the substrate can be endogenous to the yeast cell.

In other embodiments of this aspect of the disclosure, the substrate can be exogenous to the yeast cell.

In embodiments of this aspect of the disclosure, the method may further comprise the step of modifying the first heterologous nucleic acid expression system encoding the recombinant nuclear receptor polypeptide, thereby providing a variant recombinant nuclear receptor polypeptide specifically binding to the nuclear receptor ligand.

In embodiments of this aspect of the disclosure, the method may further comprise the step of modifying the third heterologous nucleic acid expression system encoding the heterologous enzyme system, thereby allowing the heterologous enzyme system to generate the nuclear receptor ligand from the substrate.

In other embodiments of this aspect of the disclosure, the third heterologous nucleic acid expression system may comprise a heterologous polynucleotide encoding a heterologous polypeptide, the heterologous polypeptide having an enzymic activity characterized as generating a candidate nuclear receptor ligand from a substrate.

In embodiments of this aspect of the disclosure, the third heterologous nucleic acid expression system may comprise a heterologous polynucleotide encoding a plurality of heterologous polypeptides, where said heterologous polypeptides cooperate to generate a candidate nuclear receptor ligand from a substrate.

In embodiments of this aspect of the disclosure, the third heterologous nucleic acid expression system may comprise a plurality of heterologous polynucleotides encoding a plurality of heterologous polypeptides, where said heterologous polypeptides cooperate to generate a candidate nuclear receptor ligand from a substrate.

In embodiments of this aspect of the disclosure, the ligand-binding domain of the recombinant nuclear receptor polypeptide can be derived from a ligand-binding domain of a human nuclear receptor polypeptide, or a variant thereof.

In embodiments of this aspect of the disclosure, the coactivator domain of the adapter polypeptide may be derived from a coactivator domain of a human coactivator, or a variant thereof, and the coactivator binds to the ligand-binding domain of the recombinant nuclear receptor polypeptide in the presence of a ligand to activate expression of a genetic locus.

In embodiments of this aspect of the disclosure, transcription of the yeast gene allows the yeast cell to proliferate on a selective culture medium.

In other embodiments of this aspect of the disclosure, transcription of the yeast gene inhibits yeast cell proliferation on a selective culture medium.

In embodiments of this aspect of the disclosure, the method may further comprise contacting the yeast cell with at least one compound suspected of modulating the activity of at least one enzyme of the heterologous enzyme system, thereby allowing the identification of the at least one compound as an activator or inhibitor of the at least one enzyme.

In some embodiments of this aspect of the disclosure, the at least one compound can be suspected of enhancing the activity of at least one enzyme of the heterologous enzyme system.

In embodiments of this aspect of the disclosure, the at least one compound can be suspected of inhibiting the activity of at least one enzyme of the heterologous enzyme system.

In other embodiments of this aspect of the disclosure, the method may further comprise contacting the yeast cell with at least one compound suspected of modulating the transcriptional activity of the third heterologous nucleic acid expression system encoding a heterologous enzyme system, thereby allowing the identification of the at least one compound as an activator or inhibitor of the transcriptional activity of the third heterologous nucleic acid expression system.

DETAILED DESCRIPTION

Figure 1:
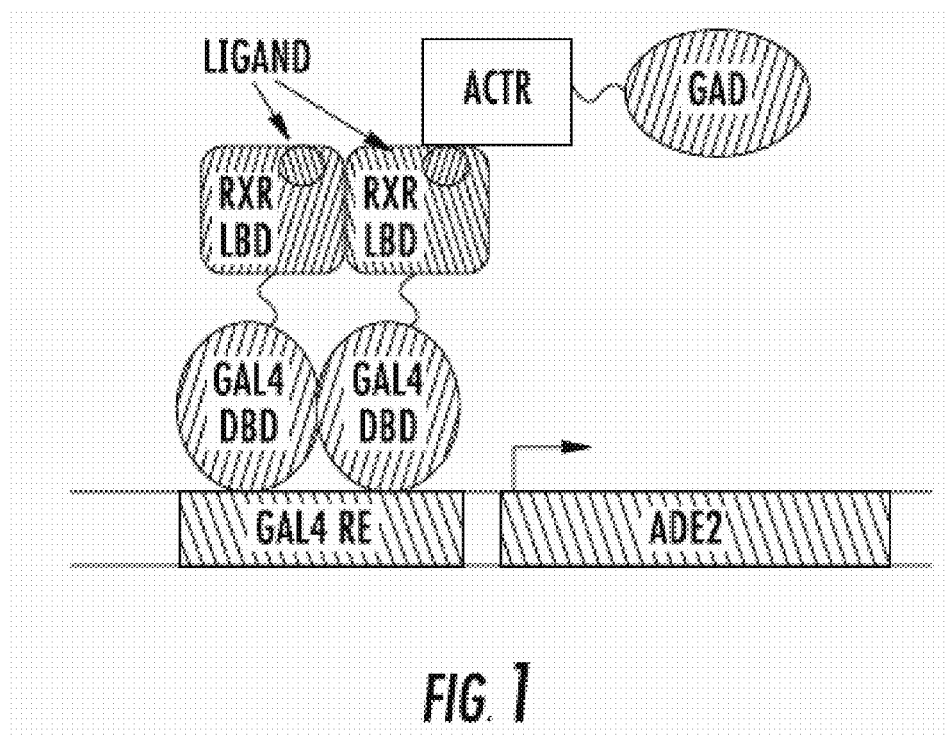
FIG. 1 shows a schematic depicting an exemplary chemical complementation scheme. For selection, yeast strain PJ69-4A has the ADE2 gene under the control of a Gal4 response element (Gal4RE). This strain is transformed with a plasmid expressing ACTR:GAD. Plasmids created through homologous recombination in PJ69-4A express a variant GBD:RXR. In media lacking adenine, yeast will grow only in the presence of a ligand that causes the RXR-LBD to associate with ACTR and activate transcription of ADE2. For clarity, only one ACTR:GAD is depicted.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

As used herein, the following terms have the meanings ascribed to them unless specified otherwise. In this disclosure, "comprises," "comprising," "containing" and "having" and the like can have the meaning ascribed to them in U.S. patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. patent law and the term is open-ended, allowing for the presence of more than that which is recited so long as basic or novel characteristics of that which is recited is not changed by the presence of more than that which is recited, but excludes prior art embodiments.

Prior to describing the various embodiments, the following definitions are provided and should be used unless otherwise indicated.

Definitions

The term "nucleic acid" as used herein refers to any natural and synthetic linear and sequential arrays of nucleotides and nucleosides, for example cDNA, genomic DNA, mRNA, tRNA, oligonucleotides, oligonucleosides and derivatives thereof. For ease of discussion, such nucleic acids may be collectively referred to herein as "constructs," "plasmids," or "vectors." Representative examples of the nucleic acids of the present invention include bacterial plasmid vectors including expression, cloning, cosmid and transformation vectors such as, but not limited to, pBR322, animal viral vectors such as, but not limited to, modified adenovirus, influenza virus, polio virus, pox virus, retrovirus, and the like, vectors derived from bacteriophage nucleic acid, and synthetic oligonucleotides like chemically synthesized DNA or RNA. The term "nucleic acid" further includes modified or derivatized nucleotides and nucleosides such as, but not limited to, halogenated nucleotides such as, but not only, 5-bromouracil, and derivatized nucleotides such as biotin-labeled nucleotides.

The terms "polynucleotide," "oligonucleotide," and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin is suggested by the terms described herein.

As used herein the terms "polypeptide" and "protein" refer to a polymer of amino acids of three or more amino acids in a serial array, linked through peptide bonds. The term "polypeptide" includes proteins, protein fragments, protein analogues, oligopeptides and the like. The term "polypeptides" contemplates polypeptides as defined above that are encoded by nucleic acids, produced through recombinant technology (isolated from an appropriate source such as a bird), or synthesized. The term "polypeptides" further contemplates polypeptides as defined above that include chemically modified amino acids or amino acids covalently or non-covalently linked to labeling ligands.

The term "gene" or "genes" as used herein refers to nucleic acid sequences (including both RNA or DNA) that encode genetic information for the synthesis of a whole RNA, a whole protein, or any portion of such whole RNA or whole protein. Genes that are not naturally part of a particular organism's genome are referred to as "foreign genes," "heterologous genes" or "exogenous genes" and genes that are naturally a part of a particular organism's genome are referred to as "endogenous genes". The term "gene product" refers to RNAs or proteins that are encoded by the gene. "Foreign gene products" are RNA or proteins encoded by "foreign genes" and "endogenous gene products" are RNA or proteins encoded by endogenous genes. "Heterologous gene products" are RNAs or proteins encoded by "foreign, heterologous or exogenous genes" and are, therefore, not naturally expressed in the cell.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from said RNA nucleic acid molecule to give a protein, a polypeptide, or a portion or fragment thereof.

The term "operably linked" refers to an arrangement of elements wherein the components so described are configured so as to perform their usual function. Control sequences operably linked to a coding sequence are capable of effecting the expression of the coding sequence. The control sequences need not be contiguous with the coding sequence, so long as they function to direct the expression thereof. Thus, for example, intervening untranslated yet transcribed sequences can be present between a promoter sequence and the coding sequence and the promoter sequence can still be considered "operably linked" to the coding sequence.

The term "transcription modulating system" as used herein refers to nucleotide sequences that are associated with a gene nucleic acid sequence and which regulate the transcriptional expression of the gene. Exemplary transcription regulatory sequences include enhancer elements, hormone response elements, steroid response elements, negative regulatory elements, and the like. The "transcription modulating system" may be isolated and incorporated into a vector nucleic acid to enable regulated transcription in appropriate cells of portions of the vector DNA. The "transcription modulating system" may precede, but is not limited to, the region of a nucleic acid sequence that is in the region 5' of the end of a protein coding sequence that may be transcribed into mRNA. Transcriptional regulatory sequences may also be located within a protein coding region, in regions of a gene that are identified as "intron" regions, or may be in regions of nucleic acid sequence that are in the region of nucleic acid.

The term "promoter" as used herein refers to the DNA sequence that determines the site of transcription initiation from an RNA polymerase. A "promoter-proximal element" may be a regulatory sequence within about 200 base pairs of the transcription start site.

The term "coding region" as used herein refers to a continuous linear arrangement of nucleotides that may be translated into a protein. A full length coding region is translated into a full length protein; that is, a complete protein as would be translated in its natural state absent any post-translational modifications. A full length coding region may also include any leader protein sequence or any other region of the protein that may be excised naturally from the translated protein.

The term "expression vector" as used herein refers to a nucleic acid vector that comprises a gene expression control region operably linked to a nucleotide sequence coding at least one polypeptide. As used herein, the term "regulatory sequences" includes promoters, enhancers, and other elements that may control gene expression. Standard molecular biology textbooks (for example, Sambrook et al., eds., 1989, "Molecular Cloning: A Laboratory Manual," 2nd ed., Cold Spring Harbor Press) may be consulted to design suitable expression vectors that may further include an origin of replication and selectable gene markers. It should be recognized, however, that the choice of a suitable expression vector and the combination of functional elements therein depends upon multiple factors including the choice of the host cell to be transformed and/or the type of protein to be expressed.

The terms "transformation" and "transfection" as used herein refer to the process of inserting a nucleic acid into a host. Many techniques are well known to those skilled in the art to facilitate transformation or transfection of a nucleic acid into a prokaryotic or eukaryotic organism. These methods involve a variety of techniques, such as treating the cells with high concentrations of salt such as, but not only, a calcium or magnesium salt, an electric field, detergent, or liposome mediated transfection, to render the host cell competent for the uptake of the nucleic acid molecules, and by such methods as sperm-mediated and restriction-mediated integration.

The term "recombinant cell" refers to a cell that has a new combination of nucleic acid segments that are not covalently linked to each other in nature. A new combination of nucleic acid segments can be introduced into an organism using a wide array of nucleic acid manipulation techniques available to those skilled in the art. A recombinant cell can be a single eukaryotic cell, or a single prokaryotic cell, or a mammalian cell. The recombinant cell may harbor a vector that is extragenomic. An extragenomic nucleic acid vector does not insert into the cell's genome. A recombinant cell may further harbor a vector or a portion thereof that is intragenomic. The term intragenomic defines a nucleic acid construct incorporated within the recombinant cell's genome.

The terms "recombinant nucleic acid" and "recombinant DNA" as used herein refer to combinations of at least two nucleic acid sequences that are not naturally found in a eukaryotic or prokaryotic cell. The nucleic acid sequences include, but are not limited to, nucleic acid vectors, gene expression regulatory elements, origins of replication, suitable gene sequences that when expressed confer antibiotic resistance, protein-encoding sequences, and the like. The term "recombinant polypeptide" is meant to include a polypeptide produced by recombinant DNA techniques such that it is distinct from a naturally occurring polypeptide either in its location, purity or structure. Generally, such a recombinant polypeptide will be present in a cell in an amount different from that normally observed in nature.

The term "non-natural" means not typically found in nature including those items modified by man. Non-natural includes chemically modified subunits such as nucleotides as well as biopolymers having non-natural linkages, backbones, or substitutions.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g., 9-(2-aminoethoxy)-H-pyrimido[5,4-b][1,4]benzoxazin-2 (3H)-one), carbazole cytidine (2H-pyrimido[4,5-b]indol-2-one), pyridoindole cytidine (H-pyrido[3',':4,5]pyrrolo[2,3-d] pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in The Concise Encyclopedia of Polymer Science and Engineering, pages 858-859, Kroschwitz, J. I., ed. John Wiley & Sons, 1990, those disclosed by Englisch et al., Angewandte Chemie, International Edition, 1991, 30, 613, and those disclosed by Sanghvi, Y. S., Chapter 15, Antisense Research and Applications, pages 289-302, Crooke, S. T. and Lebleu, B., ed., CRC Press, 1993. Certain of these nucleobases may be particularly useful for increasing the binding affinity of the oligomeric compounds of the disclosure. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278) and are presently preferred base substitutions, even more particularly when combined with 2'-O-methoxyethyl sugar modifications.

The terms "including", "such as", "for example" and the like are intended to refer to exemplary embodiments and not to limit the scope of the present disclosure.

The term "polypeptides" includes proteins and fragments thereof. Polypeptides are disclosed herein as amino acid residue sequences. Those sequences are written left to right in the direction from the amino to the carboxy terminus. In accordance with standard nomenclature, amino acid residue sequences are denominated by either a three letter or a single letter code as indicated as follows: Alanine (Ala, A), Arginine (Arg, R), Asparagine (Asn, N), Aspartic Acid (Asp, D), Cysteine (Cys, C), Glutamine (Gln, Q), Glutamic Acid (Glu, E), Glycine (Gly, G), Histidine (His, H), Isoleucine (Ile, I), Leucine (Leu, L), Lysine (Lys, K), Methionine (Met, M), Phenylalanine (Phe, F), Proline (Pro, P), Serine (Ser, S), Threonine (Thr, T), Tryptophan (Trp, W), Tyrosine (Tyr, Y), and Valine (Val, V).

"Variant" refers to a polypeptide or polynucleotide that differs from a reference polypeptide or polynucleotide, but retains essential properties. A typical variant of a polypeptide differs in amino acid sequence from another, reference polypeptide. Generally, differences are limited so that the sequences of the reference polypeptide and the variant are closely similar overall and, in many regions, identical. A variant and reference polypeptide may differ in amino acid sequence by one or more modifications (e.g., substitutions, additions, and/or deletions). A substituted or inserted amino acid residue may or may not be one encoded by the genetic code. A variant of a polypeptide may be naturally occurring such as an allelic variant, or it may be a variant that is not known to occur naturally.

Modifications and changes can be made in the structure of the polypeptides of in disclosure and still obtain a molecule having similar characteristics as the polypeptide (e.g., a conservative amino acid substitution). For example, certain amino acids can be substituted for other amino acids in a sequence without appreciable loss of activity. Because it is the interactive capacity and nature of a polypeptide that defines that polypeptide's biological functional activity, certain amino acid sequence substitutions can be made in a polypeptide sequence and nevertheless obtain a polypeptide with like properties.

In making such changes, the hydropathic index of amino acids can be considered. The importance of the hydropathic amino acid index in conferring interactive biologic function on a polypeptide is generally understood in the art. It is known that certain amino acids can be substituted for other amino acids having a similar hydropathic index or score and still result in a polypeptide with similar biological activity. Each amino acid has been assigned a hydropathic index on the basis of its hydrophobicity and charge characteristics. Those indices are: isoleucine (+4.5); valine (+4.2); leucine (+3.8); phenylalanine (+2.8); cysteine/cysteine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is believed that the relative hydropathic character of the amino acid determines the secondary structure of the resultant polypeptide, which in turn defines the interaction of the polypeptide with other molecules, such as enzymes, substrates, receptors, antibodies, antigens, and the like. It is known in the art that an amino acid can be substituted by another amino acid having a similar hydropathic index and still obtain a functionally equivalent polypeptide. In such changes, the substitution of amino acids whose hydropathic indices are within ±2 is preferred, those within ±1 are particularly preferred, and those within ±0.5 are even more particularly preferred.

Substitution of like amino acids can also be made on the basis of hydrophilicity, particularly, where the biological functional equivalent polypeptide or peptide thereby created is intended for use in immunological embodiments. The following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); proline (−0.5±1); threonine (−0.4); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4). It is understood that an amino acid can be substituted for another having a similar hydrophilicity value and still obtain a biologically equivalent, and in particular, an immunologically equivalent polypeptide. In such changes, the substitution of amino acids whose hydrophilicity values are within ±2 is preferred, those within ±1 are particularly preferred, and those within ±0.5 are even more particularly preferred.

As outlined above, amino acid substitutions are generally based on the relative similarity of the amino acid side-chain substituents, for example, their hydrophobicity, hydrophilicity, charge, size, and the like. Exemplary substitutions that take various of the foregoing characteristics into consideration are well known to those of skill in the art and include (original residue: exemplary substitution): (Ala: Gly, Ser), (Arg: Lys), (Asn: Gln, His), (Asp: Glu, Cys, Ser), (Gln: Asn), (Glu: Asp), (Gly: Ala), (His: Asn, Gln), (Ile: Leu, Val), (Leu: Ile, Val), (Lys: Arg), (Met: Leu, Tyr), (Ser: Thr), (Thr: Ser), (Tip: Tyr), (Tyr: Trp, Phe), and (Val: Ile, Leu). Embodiments of this disclosure thus contemplate functional or biological equivalents of a polypeptide as set forth above. In particular, embodiments of the polypeptides can include variants having about 50%, 60%, 70%, 80%, 90%, and 95% sequence identity to the polypeptide of interest.

"Identity," as known in the art, is a relationship between two or more polypeptide sequences, as determined by comparing the sequences. In the art, "identity" also means the degree of sequence relatedness between polypeptide as determined by the match between strings of such sequences. "Identity" and "similarity" can be readily calculated by known methods, including, but not limited to, those described in (Computational Molecular Biology, Lesk, A. M., Ed., Oxford University Press, New York, 1988; Biocomputing: Informatics and Genome Projects, Smith, D. W., Ed., Academic Press, New York, 1993; Computer Analysis of Sequence Data, Part I, Griffin, A. M., and Griffin, H. G., Eds., Humana Press, New Jersey, 1994; Sequence Analysis in Molecular Biology, von Heinje, G., Academic Press, 1987; and Sequence Analysis Primer, Gribskov, M. and Devereux, J., Eds., M Stockton Press, New York, 1991; and Carillo, H., and Lipman, D., SIAM J Applied Math., 48: 1073 (1988).

Preferred methods to determine identity are designed to give the largest match between the sequences tested. Methods to determine identity and similarity are codified in publicly available computer programs. The percent identity between two sequences can be determined by using analysis software (i.e., Sequence Analysis Software Package of the Genetics Computer Group, Madison Wis.) that incorporates the Needelman and Wunsch, (J. Mol. Biol., 48: 443-453, 1970) algorithm (e.g., NBLAST, and XBLAST). The default parameters are used to determine the identity for the polypeptides of the present invention.

By way of example, a polypeptide sequence may be identical to the reference sequence, that is be 100% identical, or it may include up to a certain integer number of amino acid alterations as compared to the reference sequence such that the % identity is less than 100%. Such alterations are selected from: at least one amino acid deletion, substitution, including conservative and non-conservative substitution, or insertion, and wherein said alterations may occur at the amino- or carboxy-terminal positions of the reference polypeptide sequence or anywhere between those terminal positions, interspersed either individually among the amino acids in the reference sequence or in one or more contiguous groups within the reference sequence. The number of amino acid alterations for a given % identity is determined by multiplying the total number of amino acids in the reference polypeptide by the numerical percent of the respective percent identity (divided by 100) and then subtracting that product from said total number of amino acids in the reference polypeptide.

As used herein, the term "transfection" refers to the introduction of a nucleic acid sequence into the interior of a membrane enclosed space of a living cell, including introduction of the nucleic acid sequence into the cytosol of a cell as well as the interior space of a mitochondria, nucleus or chloroplast. The nucleic acid may be in the form of naked DNA or RNA, associated with various proteins or the nucleic acid may be incorporated into a vector.

The term "selective agent" refers to a substance that is required for growth or for preventing growth of a cell or microorganism, for example cells or microorganisms that have been engineered to require a specific substance for growth or inhibit or reduce growth in the absence of a complementing factor. Exemplary complementing factors include enzymes that degrade the selective agent, or enzymes that produce a selective agent. Generally, selective agents include, but are not limited to amino acids, antibiotics, nucleic acids, minerals, nutrients, etc. Selective media generally refers to culture media deficient in at least one substance, for example a selective agent, required for growth. The addition of a selective agent to selective media results in media sufficient for growth.

As used herein, the term "coregulator" refers to a transcription modulator.

"Polymerase chain reaction" or "PCR" refers to a thermocyclic, polymerase-mediated, DNA amplification reaction. A PCR typically includes template molecules, oligonucleotide primers complementary to each strand of the template molecules, a thermostable DNA polymerase, and deoxyribonucleotides, and involves three distinct processes that are multiply repeated to effect the amplification of the original nucleic acid. The three processes (denaturation, hybridization, and primer extension) are often performed at distinct temperatures, and in distinct temporal steps. In many embodiments, however, the hybridization and primer extension processes can be performed concurrently. The nucleotide sample to be analyzed may be PCR amplification products provided using the rapid cycling techniques described in U.S. Pat. Nos. 6,569,672; 6,569,627; 6,562,298; 6,556,940; 6,569, 672; 6,569,627; 6,562,298; 6,556,940; 6,489,112; 6,482,615; 6,472,156; 6,413,766; 6,387,621; 6,300,124; 6,270,723; 6,245,514; 6,232,079; 6,228,634; 6,218,193; 6,210,882; 6,197,520; 6,174,670; 6,132,996; 6,126,899; 6,124,138; 6,074,868; 6,036,923; 5,985,651; 5,958,763; 5,942,432; 5,935,522; 5,897,842; 5,882,918; 5,840,573; 5,795,784; 5,795,547; 5,785,926; 5,783,439; 5,736,106; 5,720,923; 5,720,406; 5,675,700; 5,616,301; 5,576,218 and 5,455,175, the disclosures of which are incorporated by reference in their entireties. Other methods of amplification include, without limitation, NASBR, SDA, 3SR, TSA and rolling circle replication. It is understood that, in any method for producing a polynucleotide containing given modified nucleotides, one or several polymerases or amplification methods may be used. The selection of optimal polymerization conditions depends on the application.

A "polymerase" is an enzyme that catalyzes the sequential addition of monomeric units to a polymeric chain, or links two or more monomeric units to initiate a polymeric chain. In advantageous embodiments of this invention, the "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers.

A "restriction enzyme" refers to an endonuclease (an enzyme that cleaves phosphodiester bonds within a polynucleotide chain) that cleaves DNA in response to a recognition site on the DNA. The recognition site (restriction site) consists of a specific sequence of nucleotides typically about 4-8 nucleotides long.

As used herein, a "template" refers to a target polynucleotide strand, for example, without limitation, an unmodified naturally-occurring DNA strand, which a polymerase uses as a means of recognizing which nucleotide it should next incorporate into a growing strand to polymerize the complement of the naturally-occurring strand. Such DNA strand may be single-stranded or it may be part of a double-stranded DNA template. In applications of the present invention requiring repeated cycles of polymerization, e.g., the polymerase chain reaction (PCR), the template strand itself may become modified by incorporation of modified nucleotides, yet still serve as a template for a polymerase to synthesize additional polynucleotides.

A "thermocyclic reaction" is a multi-step reaction wherein at least two steps are accomplished by changing the temperature of the reaction.

A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

The term "exogenous" as used herein refers to a compound that is introduced to the interior of a cell such as a yeast cell from the surrounding environment such as a culture medium and is not the product of a metabolic or enzymic reaction within the cell.

The term "endogenous" as used herein refers to a compound that is the product of a metabolic or enzymic reaction within the cell.

Further definitions are provided in context below. Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein.

It should be emphasized that the embodiments of the present disclosure, particularly, any "preferred" embodiments, are merely possible examples of implementations, merely set forth for a clear understanding of the principles of the disclosed subject matter. Many variations and modifications may be made to the above-described embodiment(s) without departing substantially from the spirit and principles of the disclosure. All such modifications and variations are intended to be included herein within the scope of this disclosure and protected by the following claims.

Description

Methods and compositions for engineering proteins are provided, in particular, methods for engineering proteins that interact with a target compound. Embodiments of the disclosure combine chemical complementation with genetic selection to engineer proteins, polypeptides, enzymes, cellular nuclear receptors, and the like. Typically, any protein or polypeptide that interacts with a small molecule can be engineered or modified using the disclosed methods and systems. Exemplary proteins include, but are not limited to enzymes, antibodies, cell surface receptors, polypeptides involved in signal transduction pathways, intracellular polypeptides, secreted polypeptides, and transmembrane polypeptides. In some embodiments, the polypeptides interact with a small molecule that is produced naturally, such as an endogenously synthesized compound that may be converted to a ligand molecule that specifically interacts with a nuclear receptor ligand binding domain. Representative naturally produced small molecules include but are not limited to, neurotransmitters, cAMP, cGMP, steroids, purines, pyrimidines, heterocyclic compounds, ATP, DAG, IP3, inositol, calcium ions, magnesium ions, vitamins, minerals, and combinations thereof. Some embodiments provide methods and systems for engineering proteins, and in particular enzymes, that distinguish between optical isomers of a target compound.

Other embodiments provide a more efficient mammalian model system in yeast for evaluating protein/ligand interactions, and can be utilized in an array of applications including but not limited to, drug discovery. Nuclear receptors are implicated in diseases such as diabetes and various cancers. Agonists and antagonists for these nuclear receptors serve as drugs. With chemical complementation, libraries of compounds can be screened as potential agonists, as described herein. In some embodiments, antagonists can be identified with negative chemical complementation. Chemical complementation can also be extended to identify isotype-selective agonists and antagonists and used for the discovery of selective receptor modulators (e.g., SERMs).

In addition to drug discovery, the increase in sensitivity of disclosed systems and methods also provides a method for engineering receptors to recognize small molecules. For example, libraries of engineered receptors can be transformed into yeast and plated onto media containing an exogenous target ligand. These engineered receptors can be used for controlling transcription in mammalian cells, and potentially applied towards gene therapy. Furthermore, some embodiments of the disclosed system can give insight into the general mechanism for understanding the fundamentals of protein structure and function.

The addition of an adapter protein consisting of a human coactivator fused to a yeast transcriptional activator has now been shown to increase the sensitivity of chemical complementation with RXR 1000-fold, enhancing the system so that it is indistinguishable from activation by Gal4. Negative chemical complementation was performed in a different yeast strain, showing the versatility of the system, useful for performing chemical complementation with various selectable markers. This system may be extended to other human or mammalian nuclear receptor proteins, plus nuclear receptors from other organisms, and the coactivators and corepressors with which they interact.

Embodiments of the present disclosure comprise chemical complementation systems focusing on a target ligand and utilize the power of genetic selection to reveal proteins within the library that bind and activate transcription in response to that small molecule. It is contemplated, for example, that functional receptors from a large pool of non-functional variants can be isolated, even from a non-optimized library.

Chemical complementation is a method which links the proliferation of a yeast to the presence of a small molecule. This process allows high-throughput testing of large libraries. Hundreds of thousands to billions of variants can be assayed in one experiment without the spatial resolution necessary for traditional screening methods (e.g., no need for one colony per well). Cells expressing active variants will grow into colonies. Survivors can then be spatially resolved i.e. cloned (e.g. transferred to a microplate, one colony per well) for further characterization, decreasing the time and effort required to find new ligand-receptor pairs.

A chemical complementation can identify a plurality of nuclear receptors with a variety of responses to a specific ligand. Nuclear receptors that activate transcription in response to a specific ligand and not to endogenous compounds have several additional potential applications. The ability to switch a gene on and off in response to a desired compound can be used to build complex metabolic pathways, gene networks, and to create conditional knockouts and phenotypes in cell lines and animals. This ability can also be useful in gene therapy and in agriculture to control expression of therapeutic, pesticidal, or other genes. A variety of responses would be useful in engineering biosensor arrays: an array of receptors with differing activation profiles for a specific ligand could provide concentration measurements and increased accuracy of detection.

The ability to engineer proteins that activate transcription in response to a desired compound with a variety of activation profiles provides a method of identifying enzymes. Receptors that bind the product of a desired enzymatic reaction can be used to select or screen for enzymes or modified enzymes that perform this reaction. The enzymes may be natural or engineered. The stringency of the assay can be adjusted by using ligand-receptor pairs with lower or higher $EC_{50}$.

The human retinoid X receptor (RXR) is a ligand-activated transcription factor of the nuclear receptor superfamily. RXR plays an important role in mammalian morphogenesis and differentiation and serves as a dimerization partner for other nuclear receptors. Like most nuclear receptors, RXR has two structural domains: the DNA binding domain (DBD) and the ligand binding domain (LBD), which are connected by a flexible hinge region.

The DBD contains two zinc modules, which bind a sequence of six bases. The LBD has affinity for a small molecule ligand, including phytanic acid, docasahexaenoic acid and 9-cis retinoic acid (9cRA) with which it may bind, thereby activating transcription.

RXR is a modular protein; with the DBD and LBD functioning independently. Therefore, the RXR LBD can be fused to a DBD from another source and retain functionality. A conformational change is induced in the LBD upon ligand binding, which initiates recruitment of coactivators and the basal transcription machinery resulting in transcription of the target gene.

Nuclear receptors have evolved to bind and activate transcription in response to a variety of small molecule ligands. The known ligands for nuclear receptors are chemically diverse, including, but not limited to, steroid and thyroid hormones, vitamin D, prostaglandins, fatty acids, leukotrienes, retinoids, antibiotics, and other xenobiotics. Evolutionarily closely related receptors (e.g., thyroid hormone receptor and retinoic acid receptor) bind different ligands, whereas some members of distant subfamilies (e.g., RXR and retinoic acid receptor) have affinity for the same ligand. This diversity of ligand-receptor interactions suggests that it should be possible to engineer LBDs with a large range of novel specificities.

The crystal structure of RXR bound to 9cRA elucidates important hydrophobic and polar interactions in the LBD binding pocket. A subset of 20 hydrophobic and polar amino acids within 4.4 Å of the bound 9cRA can be varied to make a library. These residues in RXR are good candidates for creating variants that can bind different ligands through site directed mutagenesis, because side chain atoms, not main chain atoms, contribute the majority of the ligand contacts. It is contemplated that a library of RXR LBDs with all 20 amino acids at each of the 20 positions in the ligand-binding pocket, when screened against multiple compounds, could produce many new ligand-receptor pairs. It is further contemplated that other LBDs from other nuclear receptors can likewise be varied and screened against a target ligand.

Codon randomization creates protein libraries with mutations at specific sites. In one embodiment, a modified version of the Sauer codon randomization method to create a library of binding pocket variants of RXR is provided. This library allowed exploration of a vast quantity of sequence space in a minimal amount of time.

Chemical complementation allows testing for the activation of protein variants by specific ligands using genetic selection. In one embodiment LG335, a synthetic retinoid-like compound, was used as a model for the discovery of ligand-receptor pairs from large libraries using chemical complementation. LG335 was previously shown to selectively activate an RXR variant and not activate wild-type RXR. Combining chemical complementation with a large library of protein variants decreases the time, effort, and resources necessary to find new ligand-receptor pairs.

Enzyme Engineering

The present disclosure encompasses methods and compositions for engineering a polypeptide or system of polypeptides, for example an enzyme(s), to produce or interact with a desired molecule. Generally, a desired molecule of interest (or the reaction product) is selected, together with a suitable corresponding nuclear receptor. Modifications to the target nuclear receptor can be designed. For example, the X-ray structure of the target nuclear receptor can be loaded into a modeling program including, but not limited to, INSIGHT® or FLEXX®, along with the structure of the desired target molecule. Specific in silico interactions of the target receptor with the target molecule/ligand can be analyzed and those amino acids that may contribute to the ligand binding can be noted for modification. Generally, a nuclear receptor is selected that has at least a detectable amount of interaction with the target molecule or ligand or a binding pocket of a similar size and shape. The interaction can then be modulated as desired by creating a library of modified receptors.

To create the library, site-specific codon randomization can be used. It will be appreciated that any process for generating a library of modified receptors can be used. Site-specific codon randomization involves modifying the amino acids identified through modeling as having or believed to have direct or indirect interactions with the ligand. When producing or designing the oligonucleotide, in place of those amino acids, there will be a degenerate code based on the combination of nucleotides that are desired. For example, if the modification can be a change from alanine to a cysteine, leucine, phenylalanine, isoleucine, threonine, serine, valine and methionine. The nucleotide sequence for the alanine is GCC and to possibly incorporate all of the desired amino acids mentioned above, the following changes in each position must be made:

| G 1 | C 2 | C 3 |
|---|---|---|
| T | T | |
| A | | |
| G | | G |
| | C | C |

The oligonucleotide can be designed to have either a T, A, or G in the first position, a T or C in the second position, and a G or C in the third position. For example, if a TTG (one of the combinations above) is in place of the GCC, a leucine would be incorporated instead of the alanine. Therefore, when the oligos are synthesized, there would be the possibility of a T, A, or G in the first position, a T or C in the second position, and a G or C in the third position. The oligonucleotides may be designed to include insertions or deletions. The oligonucleotides have ends that are homologous to the vector in which the gene will be introduced to.

To create a receptor library, the vector into which the gene will be incorporated will be cut with restriction enzymes, deleting a fragment of the wild-type gene. Oligonucleotides will be designed with homologous ends to the vector as mentioned above, but these oligonucleotides will also be designed such that they overlap each other. The overlapping ends will hybridize to each other, and using for example the enzyme Klenow, the ends are filed in. Then, using the polymerase chain reaction (PCR) the full gene or a fragment thereof will be amplified. The vector and gene can be introduced into yeast using transformation protocols, such as those of Gietz et al. ((2002) *Meth. Enzymol.* 350: 87-96). During transformation, the vector and gene or gene fragment will homologously recombine, and the various nuclear receptor mutants will be expressed.

To select for variants that bind a desired small molecule, chemical complementation is be used. Chemical complementation is a general method of linking any small molecule to genetic selection. Chemical complementation is a derivative of the yeast two-hybrid system, where in a three-component system that in one embodiment comprises a human nuclear receptor protein, its coactivator protein, and a small molecule ligand, where the nuclear receptor and coactivator associate and activate transcription only in the presence of the ligand. An exemplary yeast strain contains a Gal4 response element fused to the ADE2 gene. It is contemplated, however, that a suitable transcription control element such as, but not limited to, Gal4 may be operably linked to any gene or gene cluster that can be expressed under the regulatory control of the transcription element. For example only, in place of ADE2, HIS3 may be used, allowing growth of the yeast host histidine auxotroph in the absence of an exogenous histidine supply.

If adenine is not provided in the medium, the yeast will not be able to proliferate unless they are able to make their own, and to do that, expression of ADE2 needs to be activated. The following exemplary plasmids can be utilized: $1^{st}$ plasmid encodes a fusion protein of the Gal4 DNA binding domain (Gal4 DBD) fused to the variant receptor ligand-binding domain (LBD); the other fusion protein comprises a human coactivator protein fused to the Gal4 activation domain. In the presence of ligand, the ligand will bind to the variant receptor ligand-binding domain and the Gal4 DNA binding domain will bind to the Gal4 response element. This will cause the protein to undergo a conformational change, and will recruit the coactivator fused to the Gal4 activation domain. This, in turn, will result in RNA polymerase being recruited and activation of transcription of the downstream gene.

The transformed yeast from above can be plated onto a culture medium containing the desired small molecule. Through chemical complementation, the variant receptor that is able to bind the desired molecule and activate the ADE2 gene allows that yeast clone to grow. The plasmid from that colony will be rescued and sequenced and an engineered receptor will be identified and can be carried on to the next step. It will be appreciated that there may be many variant receptors that allow the yeast to grow without binding the targeted ligand. For example, they may be constitutively active or bind an endogenous small molecule ligand. These receptors may be identified through screening without the targeted ligand being present. Alternatively, they may be removed from the library by negative genetic selection on media without the targeted ligand, either before or after chemical complementation. Once an engineered receptor has been created, this gene can be integrated into the yeast genome, for example via homologous recombination. This will create a new strain useful in the following process.

Once the receptor that can bind the small molecule has been identified, individual enzymes or a library of enzymes can be evaluated to generate a product of interest. Libraries of naturally occurring enzymes, for example expression cDNA libraries, may be evaluated. Also, libraries of enzymes can be created using a number of mutagenic protocols, such as DNA shuffling, RACHITT, Error-Prone PCR, to name a few. For example, an enzyme that is suspected of interacting with the target molecule can be selected and mutagenized with conventional techniques. Alternatively, yeast or microorganisms can be randomly mutated.

In one embodiment, chemical complementation is used to identify the engineered enzyme. In this embodiment the library of engineered enzymes will be introduced into the yeast strain transformed with a heterologous nucleic acid sequence encoding a modified nuclear receptor, as described above. This yeast strain will have a variant receptor integrated into its genome, and the variant receptor is able to bind the product molecule. Once the engineered enzymes have been transformed into the yeast strain, the yeast will be spread onto selective plates (for example, plates lacking adenine or histidine) containing the reactants involved in the enzymatic reaction that can be used to synthesize the missing product. The yeast will be able to take the reactants and if the yeast express an engineered enzyme that can convert the reactants to the reaction product, then the yeast will survive. In the alternative, the yeast cell engineered with a desired nuclear receptor LBD-DBD construct may be able to use an endogenous substrate, i.e. a chemical compound not present in the culture medium, as the starting point for the conversion by the enzyme or enzyme system to a ligand molecule that has affinity for the target LBD. The yeast will survive because the reaction product will be able to bind to the variant receptor, and activate transcription of the ADE2 gene or other selection gene. The DNA from the yeast colony that grew will be rescued and sequenced.

Target compounds that serve as ligands can be selected from any variety of natural or synthetic compounds. In one embodiment, natural products with agricultural or medicinal applications can be selected as target compounds. The search for natural products as potential agrochemical agents has increased due to the demand for crop protection chemicals. In 1990, the world market value of pesticides totaled nearly $23 billion. Synthetic chemical pesticides are used to protect crops but several developments have triggered the search for alternative compounds. First, resistance has developed against synthetic chemical pesticides. Second, concern has arisen regarding potential human health risks. Third, there is a growing awareness of environmental damage, such as contamination of soil, water, and air. New environmentally friendly methods are being pursued to rectify these problems. The disclosed methods can be used to identify new prototype pesticides in natural products produced by microorganisms, for example, which are perceived as more environmentally friendly and acceptable. The natural products would be applied as the synthetic chemical pesticides have been or the biosynthetic genes would be expressed in transgenic plants. This strategy has been widely applied using the *Bacillus thuringiensis* toxin. In another embodiment, genes for toxins are delivered to target pest species using insect-specific viruses that leave beneficial insects unharmed. These "greener" technologies require not only identification of active natural products but also the genes for their biosynthesis. With these applications in mind, and because of their availability, three compounds have been chosen as target ligands. Barbamide and jaspamide are relevant to the agricultural industry. Resveratrol has antiviral, antimicrobial, and anticancer effects.

Barbamide is a natural product from the marine cyanobacterium, *Lyngbya majuscula*. From 295 g of algae, 258 mg of pure barbamide can be isolated. This chlorinated lipopeptide has potent mollucuscidal activity. The gene cluster for barbamide biosynthesis from *L. majuscula* has been cloned and analyzed. An approximately 26 kb region of DNA from this organism specifies the biosynthesis of barbamide. The gene cluster revealed 12 open reading frames and it is believed that barbamide is synthesized from acetate, L-phenylalanine, L-cysteine, and L-leucine. Polyketide synthase and non-ribosomal peptide synthetase modules accomplish biosynthesis. A trichloroleucine intermediate is involved, but an unresolved issue is its transfer between modules. The total synthesis of barbamide has been reported.

Jaspamide was isolated from various marine sponges and exhibits insecticidal (against *Heliothis virescens*) and fungicidal activity (against *Candida albicans*). It is completely inactive against a series of Gram negative and Gram-positive bacteria. From 700 g of sponge tissue, 80 mg of pure jaspamide was isolated. The biosynthetic pathway has not been elucidated, but its structure suggests polyketide synthase and non-ribosomal peptide synthetase modules. Since it is a fungicide, a bacterial chemical complementation system for engineering nuclear receptors and discovering the genes involved in the biosynthesis of this compound would be used.

Resveratrol is a stilbene phytoalexin that is produced in at least 72 plant species. Phytoalexins are low molecular weight antimicrobial metabolites that are produced by plants for protection against a wide range of pathogens. Some nuclear receptors are known to bind resveratrol, making the DNA shuffling approach to engineer a receptor highly relevant. This compound is commercially available on the gram scale.

Development of an Amine Dehydrogenase (AmDH)

Another embodiment provides methods and systems for engineering an enzyme, for example $NAD^+$-dependent amine dehydrogenase (AmDH) from an (S)-amino acid dehydrogenase (AADH) by changing its small pocket specificity. The enzyme can preferentially produce single optical isomer products, or use single optical isomer products as a substrate. Thus, the disclosure provides methods and compositions for generating polypeptides that can distinguish between optical isomers of a compound. Genetic selection of functional AmDH variants can be achieved through the action of a nuclear receptor activating transcription of an essential gene in response to the desired (R)-amine product. Whereas the first target is a model methyl arylalkyl ketone, the target in the second phase is an acetophenone derivative closer to desired applications.

Conceptually, a concise and economical route to enantiomerically pure products, for example amines, starts from the corresponding reactants, in this case ketones and uses ammonium formate to generate the amine in up to 100% yield and selectivity with concomitant recycling of $NAD(P)^+$ to NAD(P)H using enzymes such as formate dehydrogenase (FDH).

The starting enzyme is typically examined for, albeit small, levels of activity against a substrate, for example the ketone substrate in a high ammonia environment, either (i) in water/liquid ammonia-mixtures, or (ii) in saturating concentrations of ammonium formate or ammonium carbonate. A sensitive assay can be employed to check for NADH consumption such as formation of formazan ($\lambda_{max}$=450 nm). In this embodiment, an (S)-amino acid dehydrogenase, either PheDH from *Rhodococcus rhodocrous* or LeuDH from *Bacillus stearothermophilus*, an (R)-AmDH can be developed through change of substrate specificity. Diversity is generated within the respective gene through both random mutagenesis and recombination. Selection via binding of the product to a nuclear receptor with subsequent transcriptional control is chosen as the strategy to assay for successful variants.

Nuclear receptors PXR, BXR, and RAR can be used for engineering (R)-amine activated transcription with the disclosed methods and compositions. For example, these nuclear receptors can be engineered to activate the transcription of the essential metabolic gene ADE2 in response to the (R)-amines in the modified *Saccharomyces cerevisiae* strain PJ69. PXR is chosen because of its broad substrate specificity. BXR is chosen because it is already known to activate transcription in response to amines. Random and structure-based approaches of creating libraries to engineer the nuclear receptors for (R)-amine activated growth through genetic selection can be used. Receptors for multiple (R)-amines will be engineered in parallel by selecting each library on multiple selective plates with the appropriate (R)-amine. Optionally, negative selection to genetically select libraries against enzymes that make an S-enantiomer product then select for the production of the R-enantiomer (or vice-versa) can be used. A nuclear receptor library for the (R)-amine ligand can be synthesized. Additionally, the (R)-amine ligand can be synthesized in vivo by an expressed AmDH from the ketone precursor supplemented within the growth medium. A mutant PheDH library can then be screened for in vivo synthesis of (R)-amines. In this overall scheme, the power of genetic selection is used to detect biocatalytic synthesis of amines. Utilizing genetic selection means that each member of the library does not need to be screened, only functional AmDH appear because they allow the microbe to grow and form a colony. Furthermore, catalysis is directly selected, as opposed to some related but indirect property (like transition state binding). Genetic selection coupled with the broad ligand specificity of nuclear receptors creates a process to rapidly improve biocatalysts for more efficient synthesis of enantiomerically pure compounds.

Selected transformants can be optimized through successive rounds of directed evolution. Further mutant libraries of PheDH/LeuDH enzymes can be screened for in vivo synthesis of (R)-amine. Mutant AmDH enzymes can be expressed and further studied for shifts in substrate specificity and changes in kinetic reaction rates.

Figure 10:
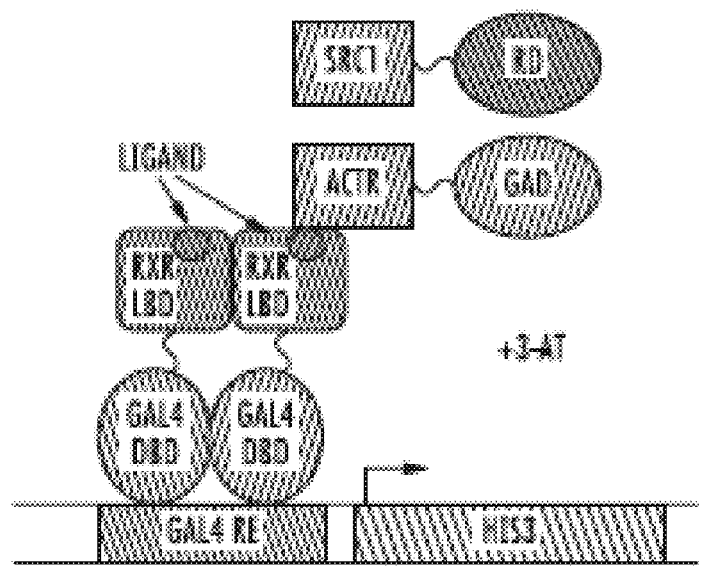
FIG. 10 is a schematic of an exemplary embodiment for the selection of selective receptor modulators in transformants incorporating a human nuclear receptor coactivator fused to a repression domain.

FIG. 10 depicts another embodiment for the identification of selective receptor modulators (analogous to selective estrogen modulators). In this embodiment, the human nuclear receptor coactivator ACTR is fused to the Gal4 activation domain (ACTR:GAD). Additionally, the human nuclear receptor coactivator SRC1 is fused to a yeast repression domain (SRC1:RD). In the presence of an agonist, these coactivator fusion proteins compete for expression of the HIS3 gene. The HIS3 gene encodes imidazoleglycerolphosphate dehydratase. In the presence of an agonist that recruits both coactivators equally, the yeast probably will produce enough histidine to survive. Adding the inhibitor 3-AT to the plates raises the threshold of enzyme that must be produced to permit growth. Compounds that selectively favor the RXR-ACTR interaction over the RXR-SRC-1 interaction will allow yeast to grow.

Figure 11:
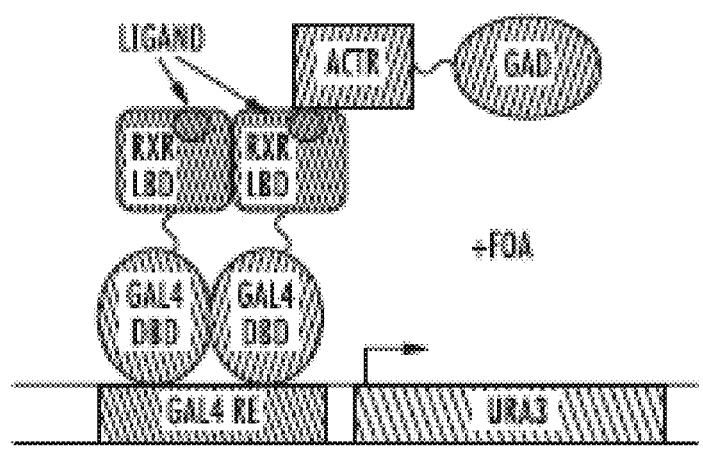
FIG. 11 is a schematic of an exemplary embodiment for the selection of receptor antagonists.

FIG. 11 is a diagram of another embodiment incorporating negative chemical selection. Human nuclear receptor coactivator, ACTR is fused to the Gal4 activation domain (ACTR:GAD). The Gal4 DBD is fused to the nuclear receptor LBS (GBD:RXR). The Gal4 DBD binds to the Gal4 response element, regulating transcription to the URA3 gene. The URA3 gene codes for orotidine-5'-phosphate decarboxylase, an enzyme in the uracil biosynthetic pathway. This gene can be used for both positive and negative selection. For positive selection, yeast expressing this gene will survive in the absence of uracil in the media. For negative selection, 5-fluoroorotic acid (FOA) is added to the media. Expression of orotidine-5'-phosphate decarboxylase coverts FOA to the toxin 5'-fluorouracil, which kills the yeast. Libraries of small molecules can be screened in a high-throughput assay in wells containing an agonist and FOA. Antagonists will allow yeast to grow.

Figure 12:
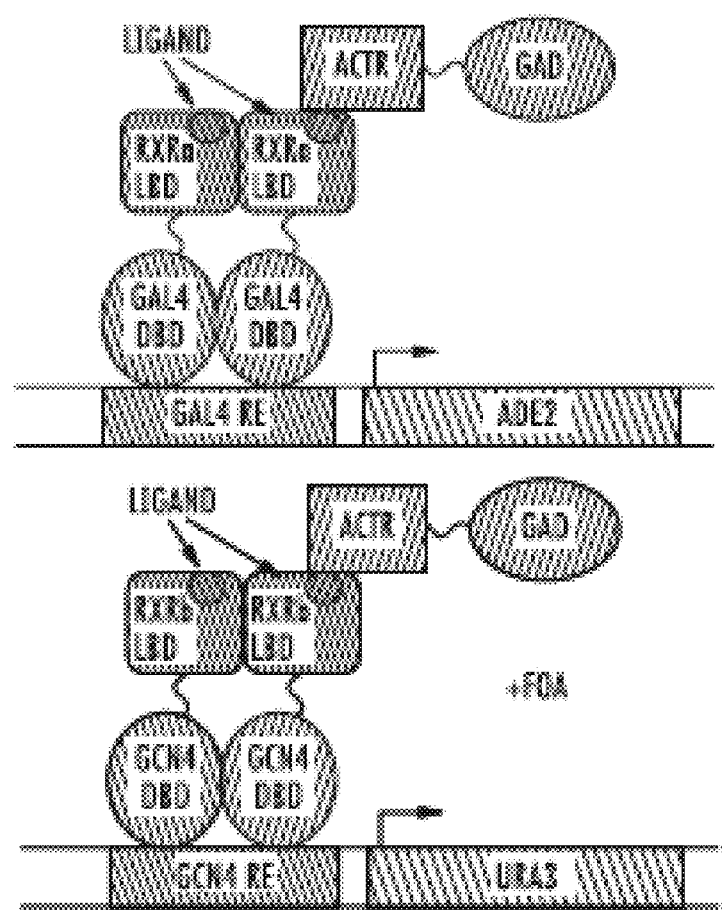
FIG. 12 is a schematic of an exemplary embodiment for chemical complementation selection of transformants to obtain isotype or isoform selective receptor agonists.

FIG. 12 is a diagram illustrating still another embodiment comprising isotype specific nuclear receptor agonists are. Each isotype can be fused to a different DBD controlling expression of different genes. The isotype for which an agonist is sought is fused to the Gal4 DBD to control expression of ADE2 (for positive chemical complementation). The isotype against which selectivity is desired, is fused to the GCN4 DBD to control expression of the URA3 gene (for negative chemical complementation). Libraries of small molecules are screened in individual wells of a 384-well plate. Compounds that do no activate the receptor will no allow the yeast to grow. Compounds that agonize both isotypes will kill the yeast. Only compounds that agonize RXRα, and either do not bind or antagonize RXRβ will allow yeast to grow.

Figure 13:
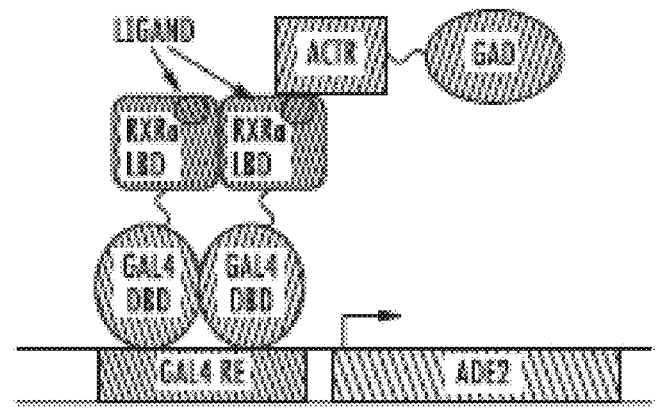
FIG. 13 is a schematic of an exemplary embodiment for chemical complementation selection of transformants incorporating a nuclear receptor coactivator fused to an activation domain for the selection of receptor agonists.

FIG. 13 shows another embodiment in which a human nuclear receptor coactivator, ACTR, is fused to the Gal4 activation domain (ACTR:GAD). The Gal4 DBD is fused to the nuclear receptor LBD (GBD:RXR). The Gal4 DBD binds to the Gal4 response element, regulating transcription of the ADE2 gene. Upon binding of the ligand, the LBD of the nuclear receptor undergoes a conformational change, which recruits the ACTR:GAD fusion protein. This brings the Gal4 AD and Gal4 DBD into close proximity activating transcription of the ADE2 gene. For clarity only one ACTR:GAD protein is shown binding one GBD:RXR. Libraries of small molecules are screened in individual wells of a 384-well plate. Agonists will allow yeast to grow.

Figure 22:
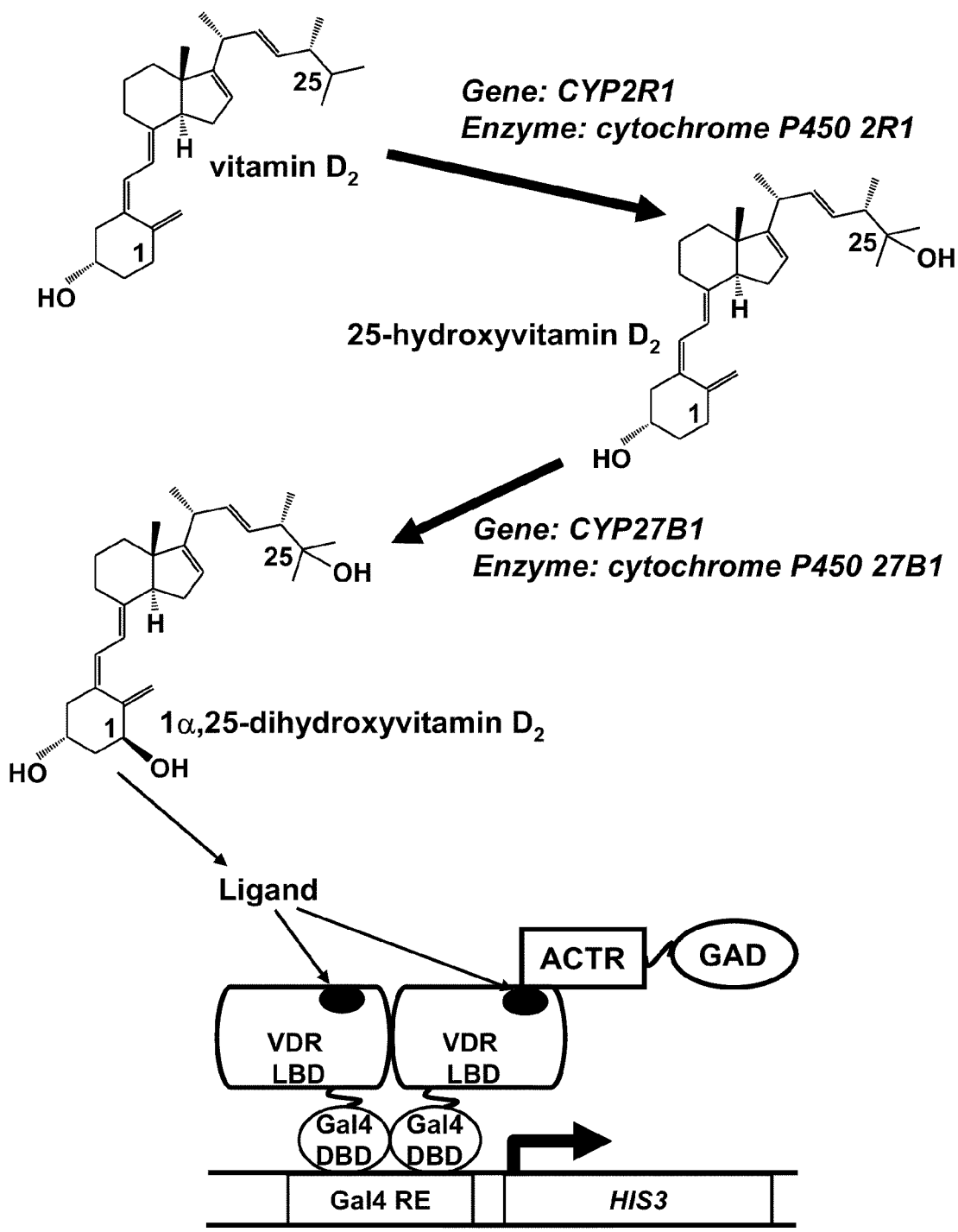
FIG. 22 schematically shows the pathway of the conversion of an endogenous precursor molecule to an active vitamin D that is able to interact with the human VDR.
Figure 23:
FIG. 23 is a series of digital images showing yeast growth on CM-His plates after 2 days at 30° C. All yeast on the plates were expressing the GBD:VDR and ACTR:GAD fusion proteins. Yeast in the four quadrants of the plates were also expressing: neither P450 enzyme, one of the P450 enzymes, or both P450 enzymes, according to the map shown on the left. The positive control plate in the center image contained 1 nM calcitriol, a known VDR ligand, and did not require P450 enzyme activity for the yeast to express HIS3 and grow on the media lacking histidine. The plate on the right contained no exogenous VDR ligand. In this case, only the quadrant with both P450 enzymes present in the yeast could synthesize the ligand for VDR which then expressed HIS3 and grew on the media lacking histidine.
Figure 23:
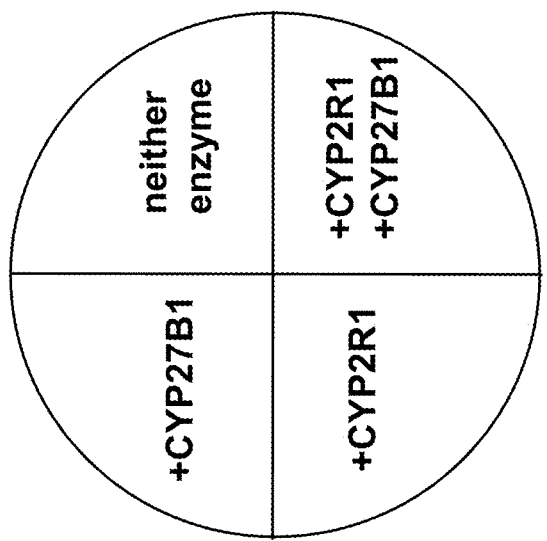

FIG. 22 schematically illustrates another embodiment of the present disclosure, and as shown experimentally in FIG. 23. In this embodiment, the nuclear receptor ligand binding domain is derived from the human vitamin D receptor.

Figure 24:
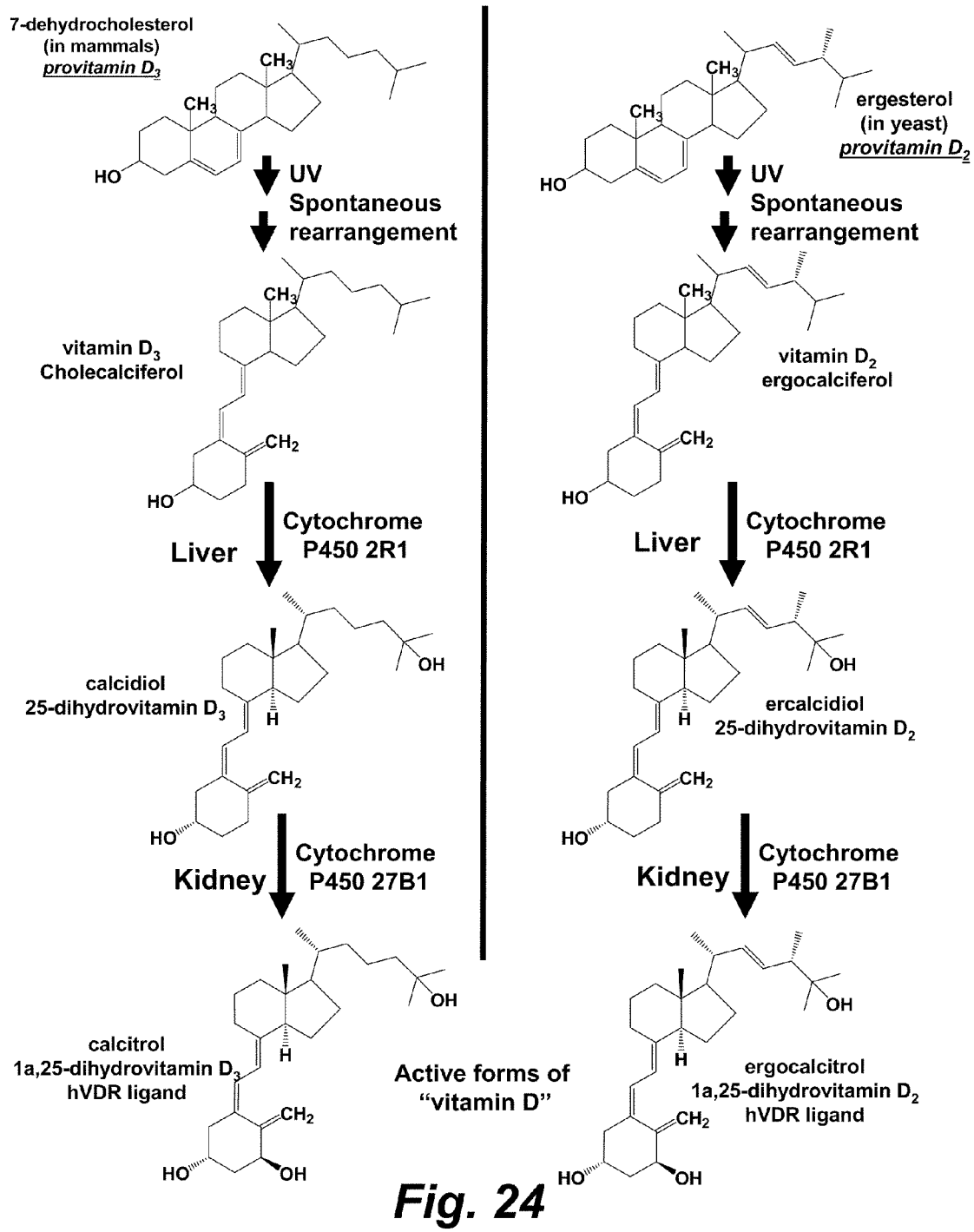
FIG. 24 schematically shows the relationships between the precursors of the ligand able to specifically bind to the VDR ligand binding domain, and the enzymes for the conversion of substrates to the final ligand molecules.

Although the vertebrate metabolic pathway results in the formation of $1\alpha,25$-dihydroxyvitamin $D_3$, in yeast metabolism of ergesterol results in the formation of $1\alpha,25$-dihydroxyvitamin $D_2$ as shown in FIG. 24. However, both compounds have affinity for, and can bind to the human vitamin D receptor (VDR) ligand binding domain. Accordingly, in this experimental example, use was made of the yeast endogenous precursor ergesterol which was then converted to $1\alpha,25$-dihydroxyvitamin $D_2$ by the heterologous cytochrome P450 2R1 (vitamin $D_3$ 25-hydroxylase) and cytochrome P450 27B1 (25-hydroxyvitamin D3 $1\alpha$-hydroxylase) enzyme system In this embodiment, a recipient yeast cell such as, but not limited to strain PJ69-4A, can be transformed with a first heterologous nucleic acid expression system pGAD-BA-ACTR, having the sequence SEQ ID NO.: 19 and encoding an ACTR:GAD fusion polypeptide, and a second heterologous nucleic acid system pVDR-wt (SEQ ID NO.: 20) encoding the GBD:VDR fusion polypeptide. Both of these fusion polypeptides may be expressed from their respective plasmids. The GBD:VDR polypeptide includes the ligand binding domain of the human vitamin $D_3$ receptor and therefore is capable of selectively binding to the ligand molecules $1\alpha,25$-dihydroxyvitamin $D_3$ and $1\alpha,25$-dihydroxyvitamin $D_2$. The yeast strain PJ69-4A further incorporates the HIS3 genetic locus operably fused to the Gal4 promoter to which the GBD domains of the ACTR:GAD and GBD:VDR fusion polypeptides may bind, thereby leading to expression of HIS3.

The yeast strain PJ69-4A having the HIS3 genetic locus operably fused to the Gal4 promoter and further having the expressed ACTR:GAD and GBD:VDR fusion polypeptides, however, is unable to grow on a selective medium lacking the amino acid histidine due to non-expression of the HIS3 gene. Expression of this gene requires activation of the operably linked to the Gal4 promoter. To achieve this expression, the embodiments of the system herein disclosed require that the GBD:VDR fusion polypeptide specifically bind its respective ligand, $1\alpha,25$-dihydroxyvitamin $D_3$, whereupon the fusion polypeptide can bind to the Gal4 promoter.

In the system, as disclosed for example in FIG. 22, the nuclear receptor ligand $1\alpha,25$-dihydroxyvitamin $D_3$ is not found or generated in wild-type yeast cells. Accordingly, to provide this ligand, the yeast strain now carrying the heterologous nucleic acids encoding the ACTR:GAD and GBD:VDR fusion polypeptides can be further transformed with a third heterologous nucleic acid expression system that encodes enzymes necessary for the synthesis of the nuclear receptor ligand. In the example as shown in shown in FIG. 22, the third heterologous nucleic acid expression system comprised two plasmids transformed into the yeast. The first plasmid, pY2653 (having the sequence according to SEQ ID NO.: 22) encodes for the expression product of the gene CYP2R1, i.e. cytochrome P450 2R1 (vitamin $D_3$ 25-hydroxylase) that can convert the endogenous substrate cholecalciferol to 25-hydroxyvitamin $D_3$. The second component of the third heterologous nucleic acid expression system is the plasmid pS0016 (having the nucleic acid sequence according to SEQ ID NO.: 21) that encodes for the expression product of the gene CYP27B1, i.e. cytochrome P450 27B1 (25-hydroxyvitamin $D_3$ $1\alpha$-hydroxylase) that can convert 25-hydroxyvitamin $D_3$ to the nuclear receptor ligand $1\alpha,25$-dihydroxyvitamin D3.

When the recipient yeast strain includes all four of the transformed plasmids and expresses the heterologous products, the ACTR:GAD and GBD:VDR fusion polypeptides, the CYP2R1 gene product cytochrome P450 2R1 (vitamin $D_3$ 25-hydroxylase), and the CYP27B1 gene product cytochrome P450 27B1 (25-hydroxyvitamin $D_3$ $1\alpha$-hydroxylase)), the yeast is able to grow on a selective medium lacking histidine, as shown in FIG. 23. It is also contemplated that the systems of the disclosure are suitable for substituting the VDR region of the recombinant nuclear receptor fusion polypeptide with any receptor ligand binding region selected to respond to a selected ligand end-product of an enzyme synthesis pathway encoded by the third heterologous nucleic acid expression system. For example, but not intended to be limiting, suitable receptor ligand binding domains may be derived from such receptors as Thyroid hormone receptor-α, Thyroid hormone receptor-β, Retinoic acid receptor-α, Retinoic acid receptor-β, Retinoic acid receptor-γ, Peroxisome proliferator-activated receptor-α, Peroxisome proliferator-activated receptor-β/δ, Peroxisome proliferator-activated receptor-γ, Rev-ErbAα, Rev-ErbAα, RAR-related orphan receptor-α, RAR-related orphan receptor-β, RAR-related orphan receptor-γ, Liver X receptor-α, Liver X receptor-β, Farnesoid X receptor, Vitamin D receptor, Pregnane X receptor, Constitutive androstane receptor, Hepatocyte nuclear factor-4-α, Hepatocyte nuclear factor-4-γ, Retinoid X receptor-α, Retinoid X receptor-β, Retinoid X receptor-γ, Testicular receptor 2, Testicular receptor 4, Homologue of the *Drosophila* tailless gene, Photoreceptor cell-specific nuclear receptor, Chicken ovalbumin upstream promoter-transcription factor I, Chicken ovalbumin upstream promoter-transcription factor II, V-erbA-related, Estrogen receptor-α, Estrogen receptor-β, Estrogen-related receptor-α, Estrogen-related receptor-βEstrogen-related receptor-γ, Glucocorticoid receptor, Mineralocorticoid receptor, Progesterone receptor, Androgen receptor, Nerve Growth factor IB, Nuclear receptor related 1, Neuron-derived orphan receptor 1, Steroidogenic factor 1, Liver receptor hornolog-1, Germ cell nuclear factor, Dosage-sensitive sex reversal, adrenal hypoplasia critical region, on chromosome X, gene 1, Small heterodimer partner, and the like.

The third heterologous nucleic acid expression system may encode for any plurality of enzymes that operably cooperate to synthesize a nuclear receptor ligand molecule that may specifically bind to the selected nuclear receptor ligand binding domain. It is further contemplated, in the alternative, that the third heterologous nucleic acid expression system may encode for any plurality of enzymes that cooperate to synthesize a potential nuclear receptor ligand wherein the synthetic end-product may have a low affinity for the selected nuclear receptor expressed in the yeast cells (compared to the affinity of the natural ligand of the nuclear receptor). In this instance, it is contemplated that the third heterologous nucleic acid expression system may be mutated to provide a library of variant nuclear receptor ligand binding domains. The variant that has highest affinity for the synthesized ligand may then be selected by an elevated growth rate when compared to other yeast cells having a variant receptor ligand binding domain of lower affinity. It is also further contemplated that the third nucleic acid expression system may itself be mutated to provide variant enzymes that may more efficiently produce a receptor ligand having affinity for the targeted nuclear receptor LBD.

The examples of the present disclosure further include systems where the enzymes synthesizing the nuclear receptor ligand molecule may use an endogenous or an exogenous substrate for the biosynthetic pathway. In the case of an exogenous substrate, the substrate should be transported into the cell via a transporter system or by passive diffusion.

The systems of the disclosure may use any suitable selective method that will allow for identification and selection of a yeast cell responding to the interaction of the synthesized nuclear receptor ligand with its target nuclear receptor ligand binding domain leading to the expression of a target gene. Suitable selective methods include supplying a required nutrient such as, but not limited to, an amino acid (histidine for example).

It is further contemplated that the systems and the methods of the present disclosure may be readily adapted to identify either an agonist or an antagonist of the heterologous enzyme system. In the case of an agonist or suspected agonist, an enzyme system that produces little or no nuclear receptor ligand that would allow the yeast strain to grow on a selective medium, may be enhanced to provide an effective amount of the nuclear receptor ligand. An antagonist will have the opposite effect and result in the inhibition of the heterologous enzyme system by interacting with one or more of the enzymes thereof, thereby reducing the amount of the nuclear receptor ligand and reducing proliferation of the yeast.

Additionally, the agonist or antagonist does not necessarily have to directly interact with at least one enzyme of the heterologous enzyme system. it is contemplated that a suspect agonist or antagonist may modulate the transcription of the one or more of the nucleic acid regions encoding an enzyme, leading to an increase or decrease in transcription and a corresponding change in the amount of an enzyme and in the overall activity of the heterologous enzyme system.

Accordingly, the embodiments of the present disclosure provide a versatile system, and methods of using, that allow for the selection of variant nuclear receptor ligand binding domains, or for the selection of variant enzymes, or combinations thereof, that may have an enhanced ability to synthesize a nuclear receptor ligand or a precursor thereof.

One aspect of the present disclosure, therefore, encompasses embodiments of a yeast cell comprising: (i) a yeast transcription modulating system comprising a first heterologous nucleic acid expression system encoding a recombinant nuclear receptor polypeptide comprising a ligand-binding domain operably linked to a DNA-binding domain and optionally to a flexible hinge domain, where the recombinant nuclear receptor polypeptide, when it is expressed in the yeast cell in the presence of a nuclear receptor ligand, specifically binds to the recombinant nuclear receptor polypeptide, thereby activating expression of a selective genetic locus; and a second heterologous nucleic acid expression system encoding an adapter polypeptide comprising a coactivator domain operably linked to a yeast transcriptional activator, and where the first heterologous nucleic acid expression system and the first heterologous nucleic acid expression system are each independently encoded by individual heterologous polynucleotides or are encoded by the same heterologous polynucleotide; (ii) a nuclear receptor ligand generating system comprising a third heterologous nucleic acid expression system encoding a heterologous enzyme system for the generation of a nuclear receptor ligand from a substrate, where the nuclear receptor ligand is characterized as specifically binding to the recombinant nuclear receptor polypeptide; and (iii) a selective genetic locus expressed in the presence of the recombinant nuclear receptor polypeptide and a nuclear receptor ligand specifically bound to the recombinant nuclear receptor polypeptide.

In embodiments of this aspect of the disclosure, the coregulator domain can be SRC-1 or ACTR.

In embodiments of this aspect of the disclosure, the third heterologous nucleic acid expression system may comprise a heterologous polynucleotide encoding a heterologous polypeptide, said heterologous polypeptide having an enzymic activity characterized as generating a candidate nuclear receptor ligand from a substrate.

In other embodiments of this aspect of the disclosure, the third heterologous nucleic acid expression system may comprise a heterologous polynucleotide encoding a plurality of heterologous polypeptides, where said heterologous polypeptides cooperate to generate a candidate nuclear receptor ligand from a substrate.

In yet other embodiments of this aspect of the disclosure, the third heterologous nucleic acid expression system may comprise a plurality of heterologous polynucleotides encoding a plurality of heterologous polypeptides, where said heterologous polypeptides cooperate to generate a candidate nuclear receptor ligand from a substrate.

In embodiments of this aspect of the disclosure, the ligand-binding domain of the recombinant nuclear receptor polypeptide can be derived from a ligand-binding domain of a human nuclear receptor polypeptide, or a variant thereof.

In embodiments of this aspect of the disclosure, the coactivator domain of the adapter polypeptide can be derived from a coactivator domain of a human coactivator, or a variant thereof, where the coactivator binds to the ligand-binding domain of the recombinant nuclear receptor polypeptide in the presence of a ligand to activate expression of a genetic locus.

In embodiments of this aspect of the disclosure, expression of the genetic locus can allows proliferation of the yeast cell on a selective medium.

In embodiments of this aspect of the disclosure, expression of the genetic locus can inhibit proliferation of the yeast cell on a selective medium.

In embodiments of this aspect of the disclosure, the heterologous enzyme system for the generation of a nuclear receptor ligand from a substrate can comprise a modified enzyme, where the modified enzyme catalyzes the formation of a receptor ligand characterized as binding to the recombinant receptor polypeptide.

In some embodiments of this aspect of the disclosure, the heterologous enzyme system for the generation of a nuclear receptor ligand from a substrate comprises vitamin $D_3$ 25-hydroxylase and 25-hydroxyvitamin $D_3$ 1α-hydroxylase, wherein said heterologous enzyme system catalyzes the formation of 1α,25-dihydroxyvitamin $D_3$, and wherein the 1α,25-dihydroxyvitamin $D_3$ binds to the recombinant nuclear receptor polypeptide comprising the ligand-binding domain of a vitamin D receptor, thereby inducing expression of a genetic locus allowing the yeast cell to proliferate on a culture medium not having histidine therein.

Another aspect of the present disclosure provides methods of modulating the transcription of a gene of a yeast cell, the methods comprising (1) providing a yeast cell or population of yeast cells, wherein said yeast cell or population of yeast cells comprises: (i) a yeast transcription modulating system comprising a first heterologous nucleic acid expression system encoding a recombinant nuclear receptor polypeptide comprising a ligand-binding domain operably linked to a DNA-binding domain and optionally to a flexible hinge domain, where the recombinant nuclear receptor polypeptide, when expressed in the yeast cell in the presence of a nuclear receptor ligand specifically binding to the recombinant nuclear receptor polypeptide, activates expression of a genetic locus; and a second heterologous nucleic acid expression system encoding an adapter polypeptide, comprising a coactivator domain operably linked to a yeast transcriptional activator, and wherein the first heterologous nucleic acid expression system and the second heterologous nucleic acid expression system are each independently encoded by individual heterologous polynucleotides or are encoded by the same heterologous polynucleotide; (ii) a nuclear receptor ligand generating system comprising a third heterologous nucleic acid expression system encoding a heterologous enzyme system for the generation of a nuclear receptor ligand from a substrate, wherein the nuclear receptor ligand is characterized as specifically binding to the recombinant nuclear receptor polypeptide; and (iii) a selective yeast genetic locus expressed in the presence of the recombinant nuclear receptor polypeptide and a nuclear receptor ligand specifically bound to the recombinant nuclear receptor polypeptide; and (2) culturing the yeast cell under conditions allowing the yeast cell to synthesize a nuclear receptor ligand from a substrate, whereupon the nuclear receptor ligand specifically binds to the recombinant nuclear receptor polypeptide, thereby inducing transcription of the selective yeast genetic locus.

In some embodiments of this aspect of the disclosure, the step of providing a yeast cell or population of yeast cells may comprise delivering to a yeast cell or population of yeast cells a plurality of third heterologous nucleic acid expression systems encoding a plurality of enzyme systems suspected of generating from a substrate a nuclear receptor ligand specifically binding the recombinant nuclear receptor polypeptide, and where the step of culturing the yeast cell under conditions allowing the yeast cell to synthesize a nuclear receptor ligand from a substrate identifies a third heterologous nucleic acid expression system encoding an enzyme system generating the nuclear receptor ligand.

In embodiments of this aspect of the disclosure, the substrate can be endogenous to the yeast cell.

In other embodiments of this aspect of the disclosure, the substrate can be exogenous to the yeast cell.

In embodiments of this aspect of the disclosure, the method may further comprise the step of modifying the first heterologous nucleic acid expression system encoding the recombinant nuclear receptor polypeptide, thereby providing a variant recombinant nuclear receptor polypeptide specifically binding to the nuclear receptor ligand.

In embodiments of this aspect of the disclosure, the method may further comprise the step of modifying the third heterologous nucleic acid expression system encoding the heterologous enzyme system, thereby allowing the heterologous enzyme system to generate the nuclear receptor ligand from the substrate.

In other embodiments of this aspect of the disclosure, the third heterologous nucleic acid expression system may comprise a heterologous polynucleotide encoding a heterologous polypeptide, the heterologous polypeptide having an enzymic activity characterized as generating a candidate nuclear receptor ligand from a substrate.

In embodiments of this aspect of the disclosure, the third heterologous nucleic acid expression system may comprise a heterologous polynucleotide encoding a plurality of heterologous polypeptides, where said heterologous polypeptides cooperate to generate a candidate nuclear receptor ligand from a substrate.

In embodiments of this aspect of the disclosure, the third heterologous nucleic acid expression system may comprise a plurality of heterologous polynucleotides encoding a plurality of heterologous polypeptides, where said heterologous polypeptides cooperate to generate a candidate nuclear receptor ligand from a substrate.

In embodiments of this aspect of the disclosure, the ligand-binding domain of the recombinant nuclear receptor polypeptide can be derived from a ligand-binding domain of a human nuclear receptor polypeptide, or a variant thereof.

In embodiments of this aspect of the disclosure, the coactivator domain of the adapter polypeptide may be derived from a coactivator domain of a human coactivator, or a variant thereof, and the coactivator binds to the ligand-binding domain of the recombinant nuclear receptor polypeptide in the presence of a ligand to activate expression of a genetic locus.

In embodiments of this aspect of the disclosure, transcription of the yeast gene allows the yeast cell to proliferate on a selective culture medium.

In other embodiments of this aspect of the disclosure, transcription of the yeast gene inhibits yeast cell proliferation on a selective culture medium.

In embodiments of this aspect of the disclosure, the method may further comprise contacting the yeast cell with at least one compound suspected of modulating the activity of at least one enzyme of the heterologous enzyme system, thereby allowing the identification of the at least one compound as an activator or inhibitor of the at least one enzyme.

In some embodiments of this aspect of the disclosure, the at least one compound can be suspected of enhancing the activity of at least one enzyme of the heterologous enzyme system.

In embodiments of this aspect of the disclosure, the at least one compound can be suspected of inhibiting the activity of at least one enzyme of the heterologous enzyme system.

In other embodiments of this aspect of the disclosure, the method may further comprise contacting the yeast cell with at least one compound suspected of modulating the transcriptional activity of the third heterologous nucleic acid expression system encoding a heterologous enzyme system, thereby allowing the identification of the at least one compound as an activator or inhibitor of the transcriptional activity of the third heterologous nucleic acid expression system.

The specific examples below are to be construed as merely illustrative, and not limiting of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

EXAMPLES

Example 1

Ligands 9-cis retinoic acid (MW=304.44 g/mol) was purchased from ICN Biomedicals.

LG335 Synthesis:

3-(1-Carbonyl)propyl-5,5,8,8-tetramethyl-5,6,7,8-tetrahydronapthylene:

2,5-dimethyl-2,5,hexanediol (5.0 g, 34 mmol) was dissolved in anhydrous benzene (150 mL). $AlCl_3$ (5.0 g, 38 mmol) was added slowly while the mixture was stirred in an ice bath, followed by stirring at room temperature for 1 hour. Another portion of $AlCl_3$ (5.0 g, 38 mmol) was then added and the reaction was heated to 50° C. and stirred overnight. The brown solution was poured over iced 0.4 M HCl (50 mL) and extracted with ether (3×50 mL). The organic layer was then sequentially washed with water, saturated aqueous $NaHCO_3$, and brine (80 mL each) and dried ($MgSO_4$). The solvent was removed in vacuo to yield 6.2 g of a yellow liquid.

The crude product was then mixed with propionyl chloride (3.2 mL, 37 mmol) and the resulting solution added dropwise to a mixture of $AlCl_3$ (5.0 g, 38 mmol) in dichloroethane (20 mL) while maintaining the temperature between 20 and 25° C. The mixture was stirred for 2 hours at room temperature, at which point it was quenched by pouring carefully over ice. The reaction mixture was then extracted methylene chloride (3×10 mL). The organics layers were then combined, washed with water and saturated aqueous $NaHCO_3$ the volatiles removed by rotary evaporation. The product was purified by silica gel column chromatography eluting with hexanes:chloroform (4:1, then 1:1) to yield 6.9 g (28 mmol, 73%) of product as a yellow oil.

3-Propyl-5,5,8,8-tetramethyl-5,6,7,8-tetrahydronapthylene:

The 3-(1-carbonyl)propyl-5,5,8,8-tetramethyl-5,6,7,8-tetrahydronapthylene (1.0 g, 4.1 mmol) in MeOH (10 mL), $H_2O$ (1 mL), and conc. HCl (3 drops) was treated with 10% Pd/C (144 mg) and subjected to catalytic hydrogenation conditions at 60 psi while heating gently overnight. When the reaction was considered complete (Rf=0.76, 5% EtOAc in hexanes) it was filtered through a celite pad and rinsed with MeOH (10 mL) and hexane (50 mL). Water (1 mL) was then added to the filtrate and the organic phase separated and washed with brine (2×20 mL). The aqueous layer was washed with hexanes (2×20 mL). The organic layers were dried ($Na_2SO_4$), filtered and the volatiles removed by rotary evaporation to produce 510 mg (2.2 mmol, 54%) of a colorless oil (5).

4-[(3-Propyl-5,5,8,8-tetramethyl-5,6,7,8-tetrahydro-2-naphtyl)carbonyl]benzoic Acid (LG335)

3-Propyl-5,5,8,8-tetramethyl-5,6,7,8-tetrahydronapthylene (2.2 g, 9.5 mmol) and chloromethyl terephthalate (2.0 g, 10 mmol) were dissolved in dichloroethane (20 mL) and $FeCl_3$ (80 mg, 490 µmol) was added. The reaction mixture was stirred at 75° C. for 24 hours. The reaction was then cooled and MeOH (20 mL) added. The resulting slurry stirred for 7 hours at room temperature, filtered and rinsed with cold MeOH (20 mL) to result in 2.1 g (5.5 mmol, 58%) of white crystals (6).

The crystals (107 mg, 280 μmol) were stirred in MeOH (2 mL), to which 5N KOH (0.5 mL) was added. This mixture was refluxed for 30 minutes, cooled to room temperature and acidified with 20% aqueous HCl (0.5 mL). The MeOH was evaporated and the residue was extracted with EtOAc (2×5 mL). The organic layers were combined and dried (MgSO$_4$) and filtered. The filtrate was treated with hexane (10 mL) and reduced in volume to 2 mL. After standing overnight the resulting crystals were collected to provide 39 mg (103 μmol, 37%) as a white powder (1). mp 250-252° C.; H$^1$ NMR (CDCl$_3$) δ 0.88 (t, 3H, —CH$_2$CH$_2$CH$_3$), 1.20 (s, 6H, CH$_3$), 1.32 (s, 6H, CH$_3$), 1.55 (dt, 2H, —CH$_2$CH$_2$CH$_3$), 1.69 (s, 4H, CH$_2$), 2.65 (t, 2H, —CH$_2$CH$_2$CH$_3$), 7.20 (s, 1H, Ar—CH) 7.23 (s, 1H, Ar—CH), 7.89 (d, 2H, Ar—CH), 8.18 (d, 2H, Ar—CH); MS (EI POS) m/z mass for C$_{25}$H$_{30}$O$_3$: Calc. 378.2189. Found 378.2195. Anal. for C$_{25}$H$_{30}$O$_3$: Calc. C, 79.33; H, 7.99. Found C, 79.10; H, 7.96.

Example 2

Expression Plasmids pGAD10-BA-ACTR (SEQ ID NO.: 19) (Chen et al., (1997) Cell 90: 569-580, incorporated herein by reference in its entirety), pGBT9Gal4, pGBDRXRα. (Azizi et al., (2003) Biochem. Biophys. Res. Comm. 306: 774-780, incorporated herein by reference in its entirety), pCMX-hRXR (Mangelsdorf et al., (1990) Nature 345: 224-229, incorporated herein by reference in its entirety), and pCMX-βGAL (Peet et al., (1998) Chem. Biol. 5: 13-21, incorporated herein by reference in its entirety). pCMX-hRXR mutants were cloned from pGBDRXR vectors using SalI and PstI restriction enzymes and ligated into similarly cut pCMX-hRXR vectors. pLuc_CRBPII_MCS was constructed as below. All plasmids have been confirmed through sequencing.

pGBDRXRα was cut with SmaI and NcoI, filled in, and blunt-end ligated to eliminate 153 amino acids of the RXR DBD. A HindIII site in the tryptophan selectable marker was silently deleted and the sole remaining HindIII site was cut, filled in, and blunt-end ligated to remove the restriction site. Unique HindIII and SacI sites were inserted into the RXR LBD gene and MfeI and EcoRI sites were removed from the plasmid using QuikChange Site-Directed Mutagenesis (Stratagene, La Jolla, Calif.) to create pGBDRXRαL-SH-ME.

pLuc_CRBPII_MCS was made by site-directed mutagenesis from pLucMCS (Stratagene, USA). Site-directed primers were designed to incorporate a CRBPII response element in the multiple cloning site (MCS), controlling transcription of the firefly luciferase gene.

Figure 17A:
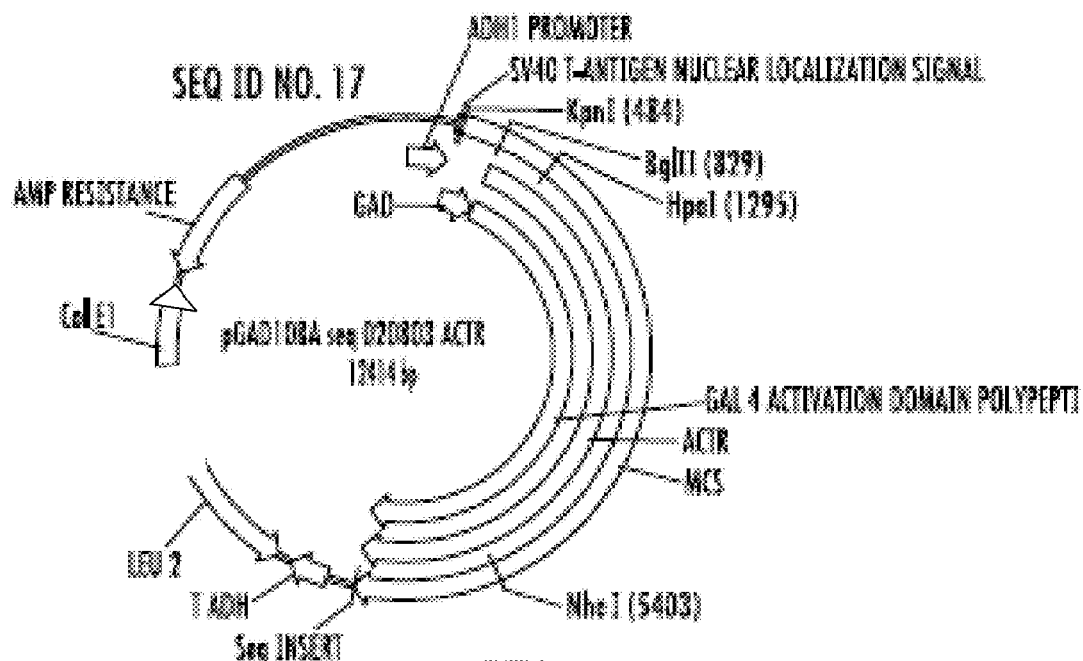
FIGS. 17a-b are diagrams of exemplary constructs according to one embodiment of the present disclosure.
Figure 17B:
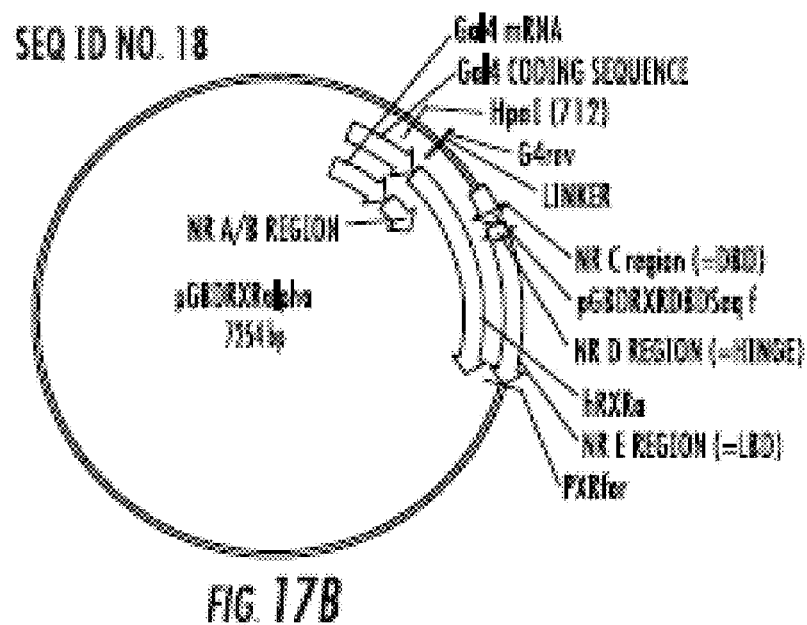
Figure 18:
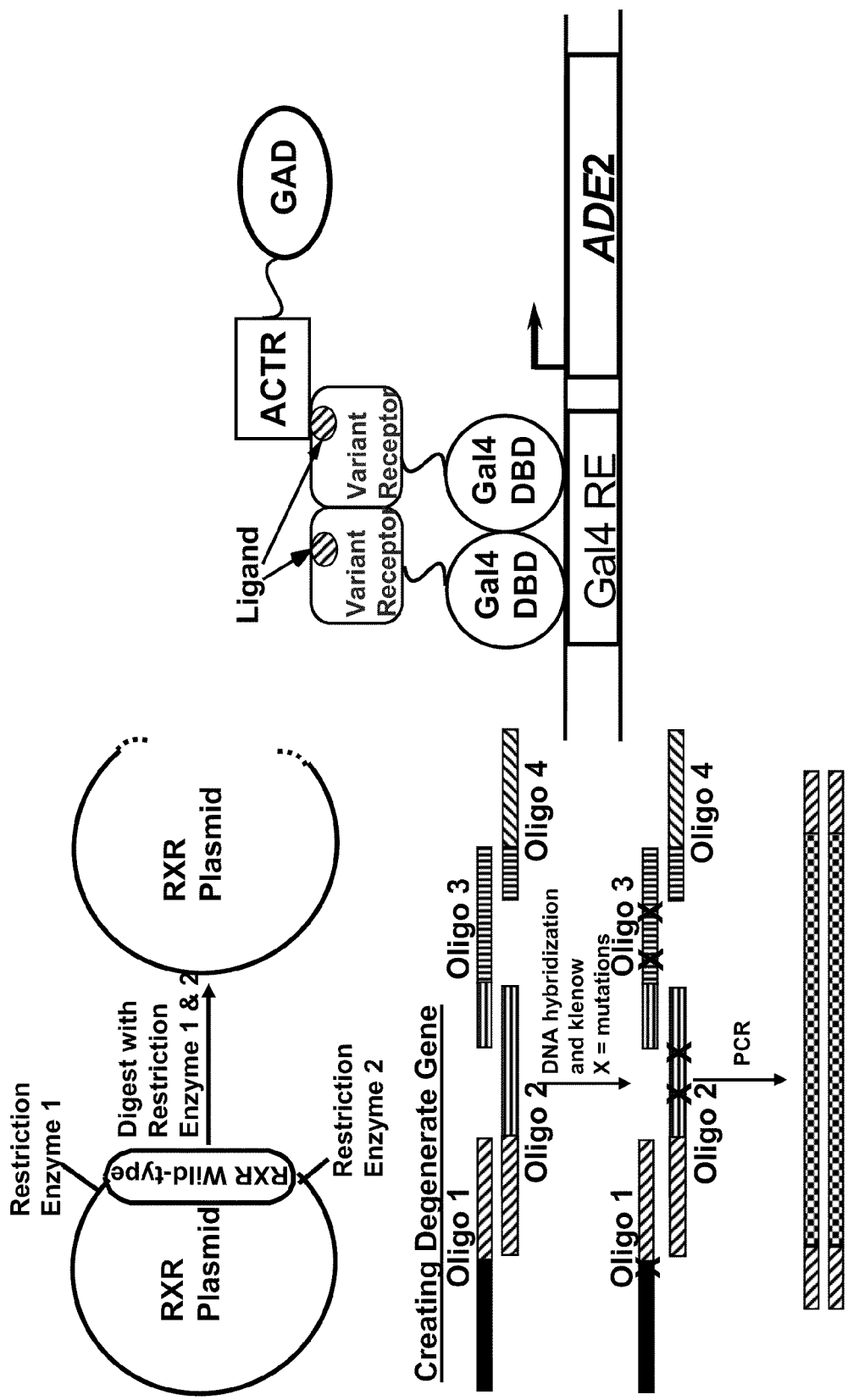
FIG. 18 shows schemes for creating a library of receptors to bind the desired small molecule. On the left is the scheme for creating the vector cassette and the variant receptors. Once these genes are made, they are introduced into yeast and put through chemical complementation shown to the right. If the variant receptor is able to bind and activate in response to the ligand, the yeast will be able to grow on media lacking adenine because the ADE2 will be turned on. Colonies that are able to grow on plates containing the small molecule and no adenine are "hits" and will then be sequenced and used for the next step.
Figure 19:
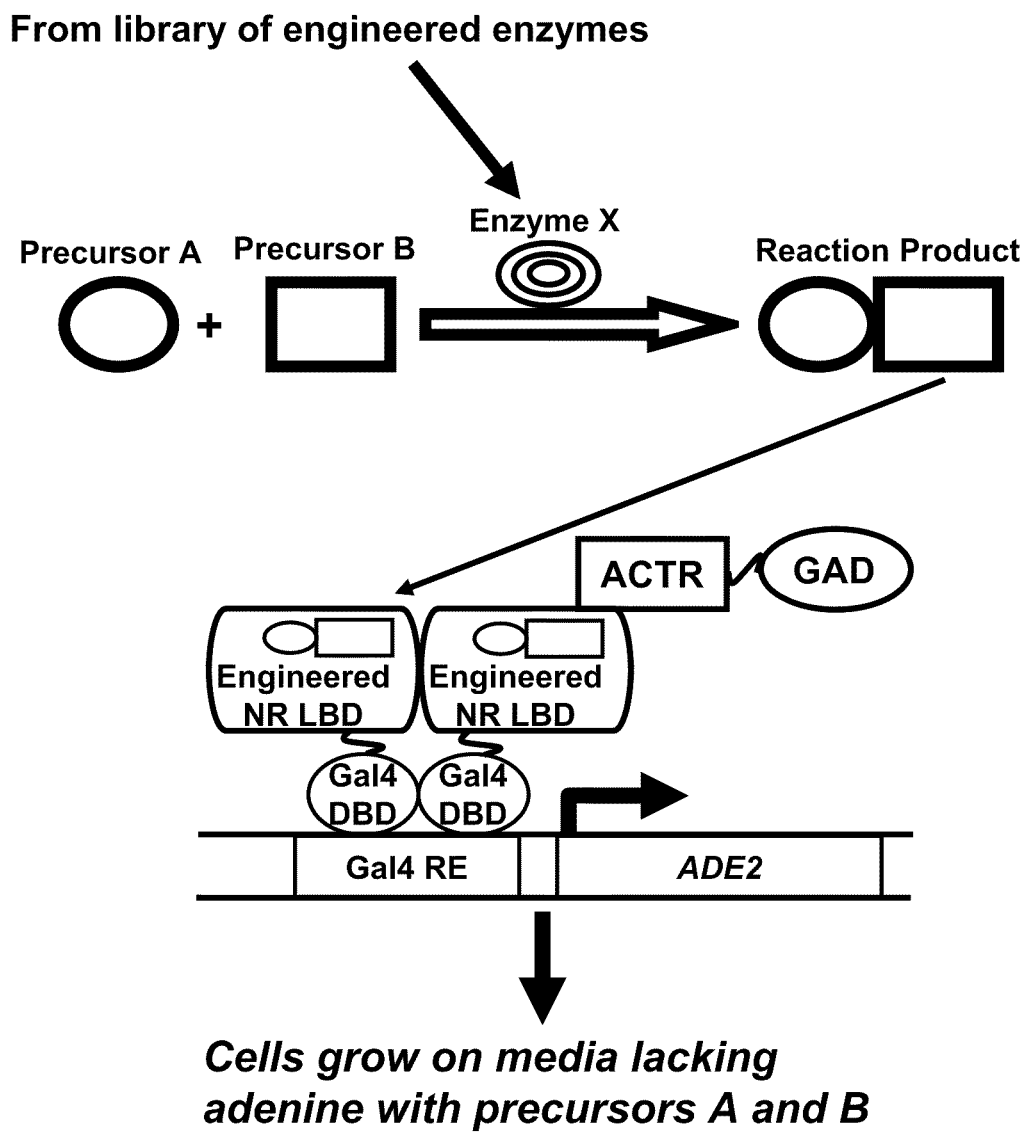
FIG. 19 schematically shows when cells grow on media lacking adenine with precursors A and B.
Figure 20:
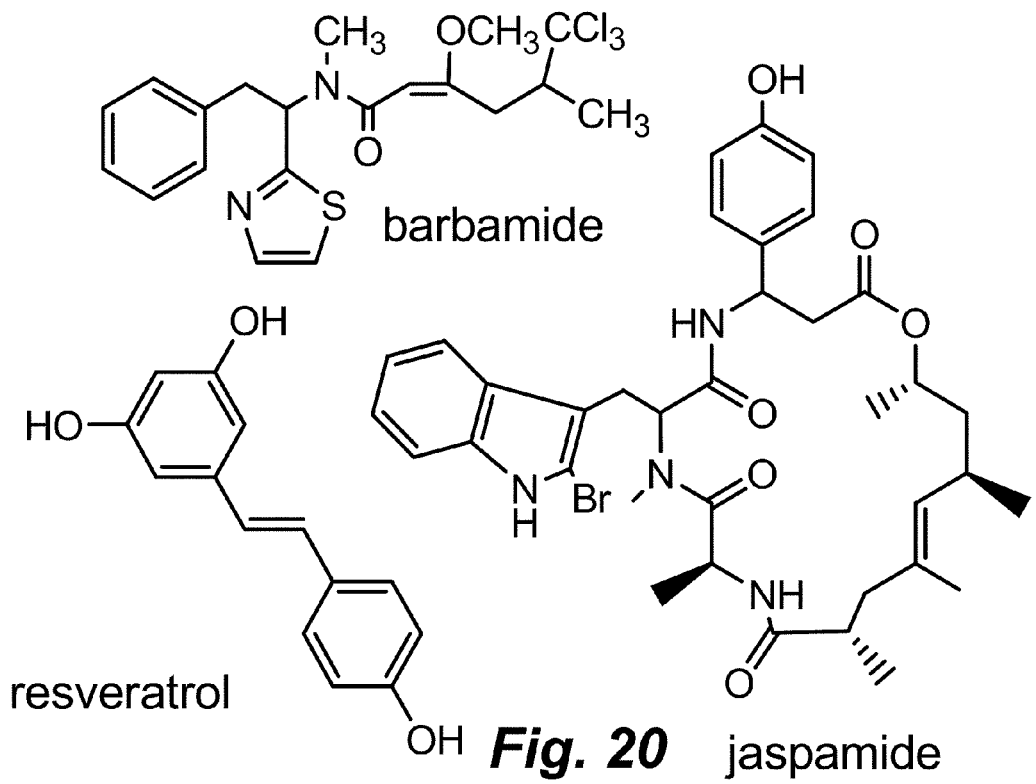
FIG. 20 illustrates compounds targeted as ligands.
Figure 21:
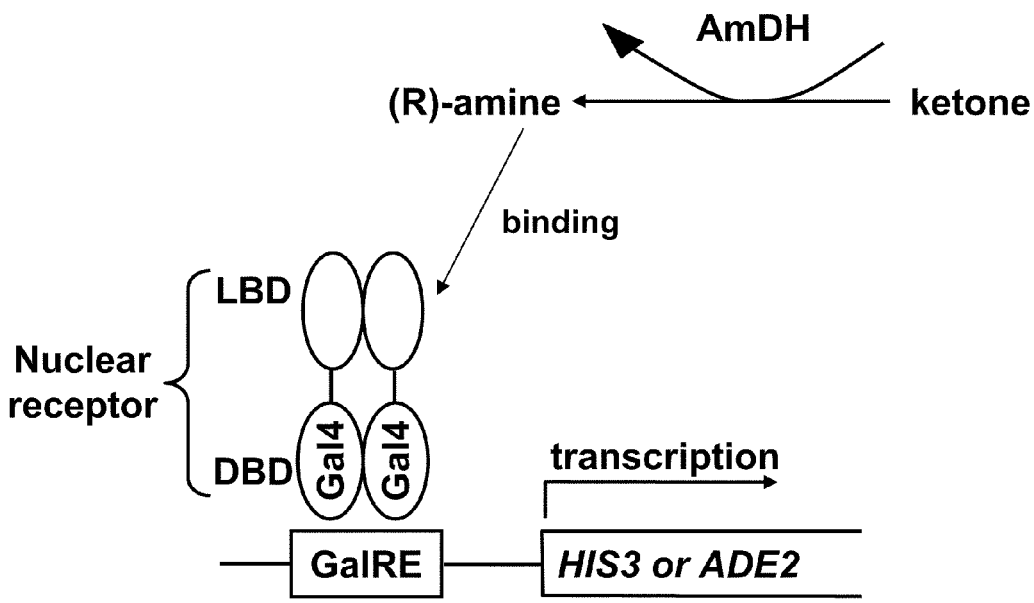
FIG. 21 schematically shows nuclear receptors with genetic selection strategy for the directed evolution of amine dehydrogenases (AmDH). The nuclear receptor is a dimer bound to DNA at the Gal4 response element (GalRE) through the Gal4 DNA binding domain (DBD), regulating transcription of an essential gene (either HIS3 or ADE2). First, a nuclear receptor ligand-binding domain (LBD) is engineered to activate transcription in response to the desired (R)-amine. Second, libraries of AmDH are transformed into the microbe and grown on media supplemented with the appropriate ketone. Only microbes with a functional AmDH that converts the ketone into the (R)-amine survive.

Plasmids expressing the fusion protein of the Gal4 activation domain with the coactivators are based on the commercial plasmid pGAD10 (Clontech, USA). The pGAD10 vector contains the Gal4 activation domain (residues 491-829) fused to a multiple cloning site (MCS) and uses a leucine marker. Additional restriction enzyme sites were added to the MCS of the plasmid via site directed mutagenesis. Primers were designed to add the following restriction enzymes: NdeI, EagI, EcIXI, NotI, XmaIII, XmaI, and SmaI, forming a new plasmid known as pGAD10-BA. (FIG. 17) This plasmid was sequenced and used for specific interaction studies mentioned in the results.

Both ACTR (residues 1-1413) and SRC-1 (residues 54-1442) genes were amplified via PCR with primers that contained BglII and NotI sites. The PCR products were digested with the two restriction enzymes and cleaned using the Zymo "DNA Clean and Concentrator Kit" (Zymo Research, Orange, Calif.) spin columns, pGADIOBA was digested with Bp and NotI and ligated with both the ACTR and SRC-1 products. Ligations were transformed into Z-competent (Zymo Research, Orange, Calif.) XL 1-Blue cells (Stratagene, La Jolla, Calif.). Transformants were rescued and sequenced. The final plasmids are called pGAD10-BA-ACTR (SEQ ID NO.: 19) and pGAD10-BASRC1.

Example 3

Plasmid Construction

The zero background plasmid, pGBDRXR:3Stop, was constructed using QuikChange Site-Directed Mutagenesis with pGBDRXRαL-SH-ME as the template and the 3Stop insert cassette (described below) as primers.

Figure 16:
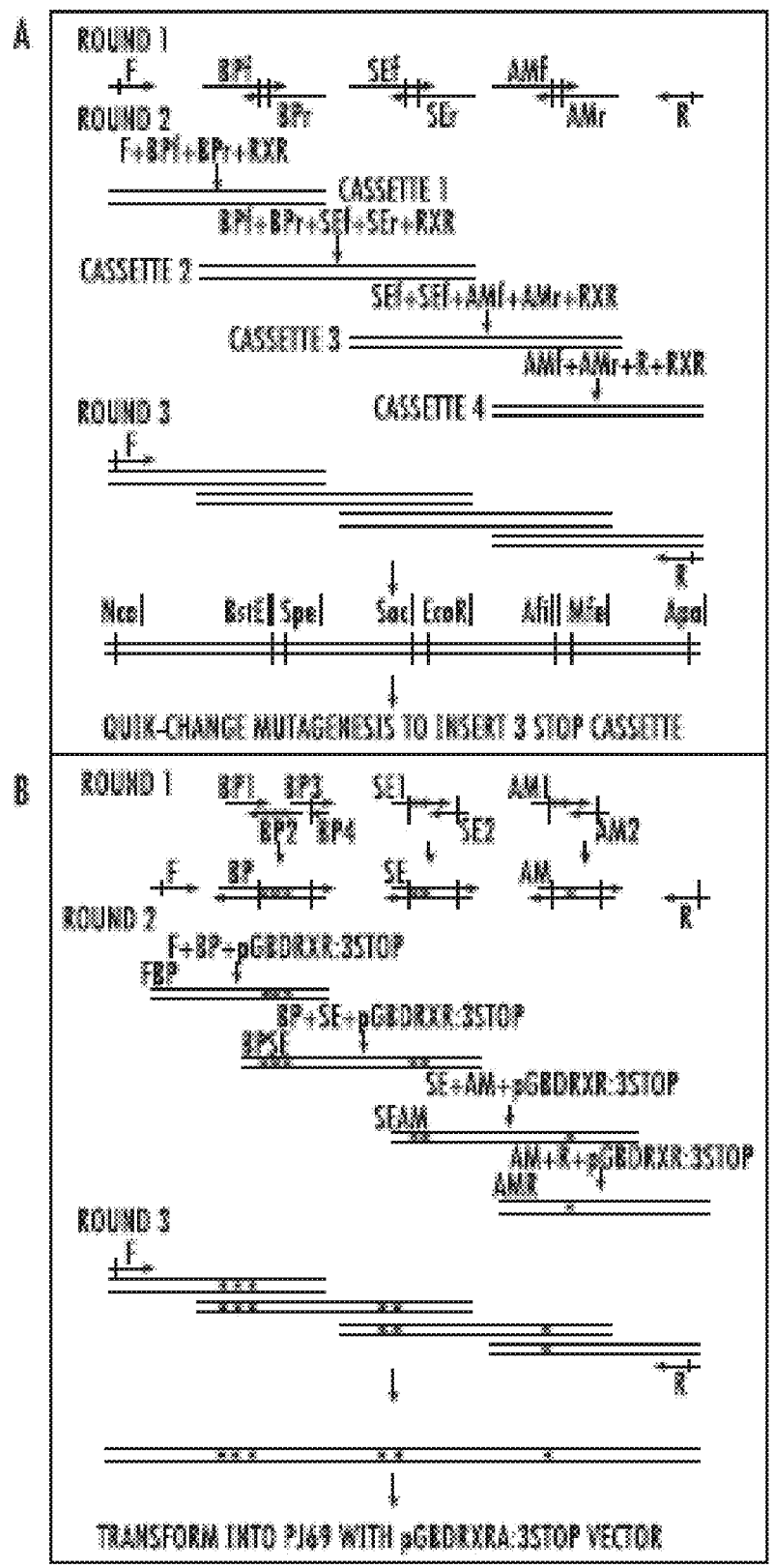
FIGS. 16a-b show schematics of exemplary methods for the construction of pGBDRXR:3stop (a) or an insert cassette library (b).

The 3Stop insert cassette was synthesized using PCR from eight oligonucleotides (FIG. 16). All PCRs were done using 2.5 U Pfu Polymerase (Stratagene, LaJolla, Calif.), 1×Pfu buffer, 0.8 mM dNTPs, 50 ng of pGBDRXRαL-SH-ME as a template, 125 ng of primers and sterile water to make 50 μL. First, four small cassettes were synthesized in reactions containing the following primers: Cassette 1, F (5'-CG-GAATTTCCCATGGGC-3') (SEQ ID NO.: 1), BPf (5'-CTCGCCGAACGACCCGGTCACCGCATGCCACTAGT-GG-3') (SEQ ID NO.: 2), and BPr (5'-CCGCTTGGC-CCACTCCACTA GTGGCATGCGGTGACC-3') (SEQ ID NO.: 3); Cassette 2, BPf, BPr, SEf (5'-CGGGCAGGCTG-GAATGAGCTCCTCGACGGAATTCTCC-3') (SEQ ID NO.: 4), and SEr (5'-CAGCCCGGTGGCCAGGAGAATTC-CGTCGAGGAGCTC-3') (SEQ ID NO.: 5); Cassette 3, SEf, SEr, AMf (5'-CTCTGCGCTCCATCGGGCTTAAGTGC-CCACCAATTGACAC-3') (SEQ ID NO.: 6), and AMr (5'-CTCCAGCATCTCCATAAGGAAGGTGT-CAATTGGTGGGCACTTAAGC-3') (SEQ ID NO.: 7); Cassette 4, AMf, AMr, and R (5'-CAAAGGATGGGCCG-CAG-3') (SEQ ID NO.: 8). The cassettes were cleaned with either the DNA Clean and Concentrator-5 (Zymo Research, Orange, Calif.) or the Zymoclean Gel DNA Recovery Kit (Zymo Research, Orange, Calif.) depending on product purity. The four cassettes were used to make the final 3Stop insert cassette in a PCR that contained each cassette, primers F and R, dNTPs, Pfu Polymerase, and sterile water to a final volume of 50 μL. The 3Stop cassette was cleaned using the Zymoclean Gel DNA Recovery Kit.

Insert Cassette Library Construction: The library of insert cassettes with randomized codons was constructed in a similar manner as above. The four cassettes (FBP, BPSE, SEAM and AMR) were made in the following ways.

For the FBP cassette, oligos BP1 (5'-GGCAAA-CATGGGGCTGAACCCCAGCTCGCCGAACGACCCG GTCACC-3') (SEQ ID NO.: 9), BP2 (5'-GCCCACTCCAC-TAGTGTGAAAAGCTGTTTGTC(A, C, or T)(A or G)(C or G)(A, C, or T)(A or G)(C or G)TTGGCA(A, C, or T)(A or G)(C or G)GTTGGTGACCGGGTCGTTCG-3') (SEQ ID NO.: 10), BP3 (5'-CTTTTCACACTAGTGGAGTGGGC-CAAGCGGATCCCACACTTCTCAGAG-3') (SEQ ID NO.: 11), and BP4 (5'-GGGGCAGCTCTGAGAAGTGTGG-GATCCG-3') (SEQ ID NO.: 12) were mixed with TE containing 100 mM NaCl to bring the total volume to 50 μL. The mixture was heated to 95° C. for 1 minute, then slowly cooled to 10° C. The annealed mixture was combined with EcoPol Buffer, dNTPs, ATP, Klenow (NEB, Beverly, Mass.), T4 DNA ligase (NEB, Beverly, Mass.) and sterile water to 200 and kept at 25° C. for 45 min before heat inactivation at 75° C. for 20 minutes. The product was cleaned with DNA Clean and Concentrator-5 to make the BP cassette. Next, BP cassette was combined with Pfu Buffer, pGBDRXR:3Stop, oligo F, dNTPs, Pfu polymerase, and sterile water to make 50 μL for a PCR. The final FBP product (300 bp) was purified using the Zymoclean Gel DNA Recovery Kit.

BPSE was made in two consecutive PCRs. First, SE1 (5'-GCAGGCTGGAATGAGCTCCTC(A, G, or T)(C or T)(G or C)GCCTCC (A, G, or T)(C or T)(G or C)TCCCACCGCTC-CATC-3') (SEQ ID NO.: 13) and SE2 (5'-CCGGTGGCCAG-GAGAATTCCGTCCTTCACGGCGATG-GAGCGGTGGG-3') (SEQ ID NO.: 14) were combined with Pfu buffer, dNTPs, Pfu polymerase, and sterile water to make 50 µL. After 5 PCR cycles, pGBDRXR:3Stop and BP were added to the reaction and the PCR was continued for 30 cycles. The product (240 bp) was purified using the Zymoclean Gel DNA Recovery Kit.

SEAM was constructed in a similar way to BPSE. SE1 and SE2 were mixed with Pfu Buffer, dNTPs, Pfu polymerase, and sterile water to 25 µL. Simultaneously, AM1 (5'-GGCTCTGCGCTCCATCGGGCTTAAGTGC-CTGGAACAT(A, G, or T)(C or T)(G or C)TTSCTTCT-TCAAGCTCATCGGGG-3') (SEQ ID NO.: 15) and AM2 (5'-GCATCTCAATAAGGAAGGTGTCAATTGT-GTGTCCCCGATGAGCTTGAAGAA-3') (SEQ ID NO.: 16) were combined with Pfu Buffer, dNTPs, Pfu polymerase, and sterile water to 25 µL. After 5 cycles, these two reactions were mixed and pGBDRXR:3Stop was added. The PCR was continued for 30 cycles. The PCR product (460 bp) was purified using the Zymoclean Gel DNA Recovery Kit.

The AMR cassette was made similarly to FBP. AM1 and AM2 were mixed with TE containing 100 mM NaCl to make 50 µL, heated to 95° C. for 1 minute, then slowly cooled to 10° C. The annealed mixture was combined with EcoPol Buffer, dNTPs, Klenow, and sterile water to 200 µL, and kept at 25° C. for 45 min before heat inactivation at 75° C. for 20 minutes. The product (AM) was precipitated with isopropanol. Next, AM and R were combined with Pfu buffer, pGBDRXR:3Stop, dNTPs, Pfu Polymerase, and sterile water to make 50 µL for a PCR. The product (140 bp) was purified using the Zymoclean Gel DNA Recovery Kit.

The four cassettes (FBP, BPSE, SEAM, and AMR) were combined in a PCR to make the library of randomized insert cassettes (6mutIC). The library was cleaned using Bio-Spin 30 columns (Bio-Rad Laboratories, Hercules, Calif.).

Example 4

Yeast Selection Plates and Transformation

Synthetic complete (SC) media and plates were made according to (Azizi et al., (2003) *Biochem. Biophys. Res. Comm.* 306: 774-780, incorporated herein by reference in its entirety). Selective plates were made without tryptophan (-Trp) and leucine (-Leu) or without adenine (-Ade), tryptophan (-Trp) and leucine (-Leu). Ligands were added to the media after cooling to 50° C.

The randomized cassette library was homologously recombined into the pGBDRXR:3Stop plasmid using the following method. pGBDRXR:3Stop was first digested with BssHII and EagI (NEB, Beverly, Mass.), and then treated with calf intestinal phosphatase (NEB, Beverly, Mass.), to make a vector cassette. Vector cassette (1 µg) and 6mutIC (9 µg) were transformed according to Geitz's transformation protocol (Geitz & Woods (2002) *Meths. Enzymol.* 350: 87-96, incorporated herein by reference in its entirety) on a 10× scale into the PJ69-4A yeast strain, which had previously been transformed with a plasmid (pGAD10-BA-ACTR) (manuscript submitted) expressing the nuclear receptor coactivator ACTR fused to the yeast Gal4 activation domain. Homologous regions between the vector cassette and the insert cassette allow the yeast to homologously recombine the insert cassette with the vector cassette forming a circular plasmid with a complete RXR LBD gene. The transformation mixture (1 mL) was spread on each of 10 large plates of SC-Ade-Trp-Leu media containing 10 µM LG335. The transformation mixture (2 and 20 µL) was also spread on SC-Trp-Leu media. These plates were grown for 4 days at 30° C.

Example 5

Molecular Modeling

Docking of LG335 in to modified binding pockets was done using the InsightII module Affinity. The wild type RXR with 9cRA crystal structure (Egea et al., (2000) *EMBO J.* 19: 2592-2601, incorporated herein by reference in its entirety) was modified using the Biopolymer module residue replace tool to make mutations in the binding pocket that corresponded to the mutations in variants I268;I130A;F313A; L436F, I268V;A272V;I310L;F313M, and I268A;I310S; F313A;L436F. The ligand was placed in the binding pocket by superimposing the carboxylate carbon and two carbons in the tetrahydronapthalene ring of LG335 onto corresponding carbons of 9cRA in the crystal structure. A Monte Carlo simulation was performed first, followed by Simulated Annealing of the best docked conformations.

Example 6

Library Evaluation

To evaluate the efficiency of library creation and selection we take a binary approach-either the sequence is or is not a designed sequence. Eq. 1 is the relevant binomial distribution for statistical evaluation of the libraries.

$$P = \frac{(N-1)!}{(k-1)!(N-k)!} p^k (1-p)^{N-k} \qquad (1)$$

In Eq. 1 N is the number of sequenced plasmids; k is the number of background or designed plasmids; p is the frequency of the occurrence of either background or designed plasmid; and P is the measure of certainty. Applying Eq. 1 to the libraries, there was 95% certainty that the unselected library was at least 72% background and the selected library was at least 78% designed sequences.

Example 7

Genotype Determination

Plasmids were rescued using either the Powers method or the Zymoprepo Kit (Zymo Research, Orange, Calif.). The plasmids were then transformed into Z-competent (Zymo Research, Orange, Calif.) XL1-Blue cells (Stratagene, La Jolla, Calif.). The QIAprep Spin Miniprep Kit (Qiagen, Valencia, Calif.) was used to purify the DNA from the transformants. These plasmids were sequenced.

Example 8

Quantitation Assays

Solid Media:
The rescued plasmids were transformed into PJ69-4A containing the pGAD10 BA-ACTR plasmid and plated on (SC)-Trp-Leu media. These plates were grown for 2 days at 30° C.

Colonies were streaked onto the following media: SC, SC-Trp-Leu, SC-Ade-Trp-Leu, SC-Ade-Trp-Leu plus increasing concentration of LG335 or 9cRA from 1 nM to 10 µM.

Liquid Media: The method used for quantitation was modified from a method developed by Miller and known in the art. Mammalian Luciferase Assay: Performed with HEK 293 cells as previously described, and known in the art.
Streaking cells onto adenine selective plates using PJ69-4A: Yeast transformants containing the plasmids were streaked onto the selective plates (SC-Ade) with different ligand concentrations using sterile toothpicks. Plates were divided into sectors for the samples and controls; the control sectors contain pGBDMT and pGBT9Gal4. The same colony was used for streaking on all the plates, ending with a SC plate to confirm efficient transfer of the cells to each plate. Both selective and non-selective plates were incubated at 30° C. for two days. Each set of genetic selection plates was replicated at least once.
Streaking cells onto FOA plates using MaVW3: Yeast transformants containing the plasmids were streaked onto selective plates, SC-Leu-Trp, containing 5-fluororotic acid, FOA, and different ligand concentrations. Plates were also divided into sectors, with pGBT9Gal4 and pGBDMT as controls. The same procedure was used for streaking as for the adenine selection plates. Plates were incubated for two days. Each set of the genetic selection plates was replicated at least once.

Example 9

Library Design

Figure 14:
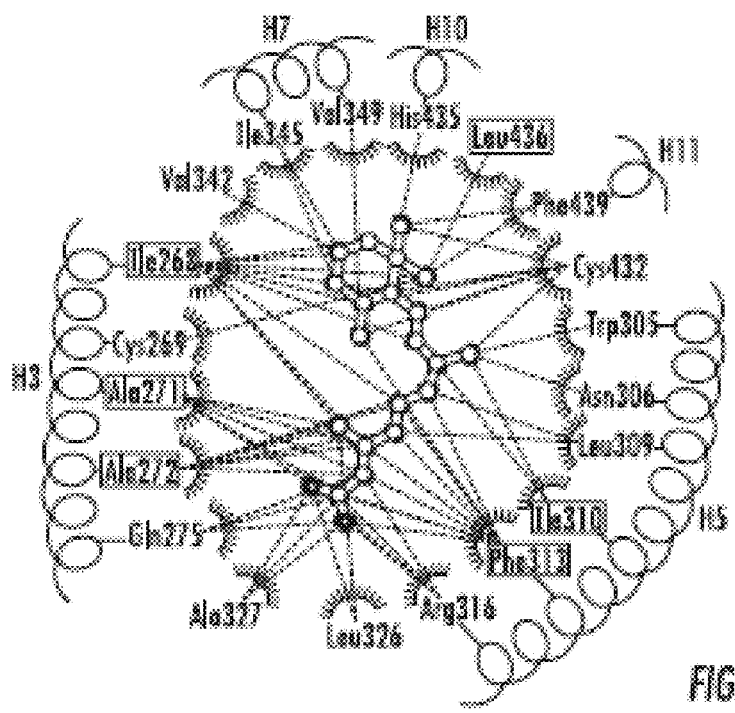
FIG. 14 is a Ligplot depiction of hydrophobic interactions between the RXR LBD and 9cRA.
Figure 15:
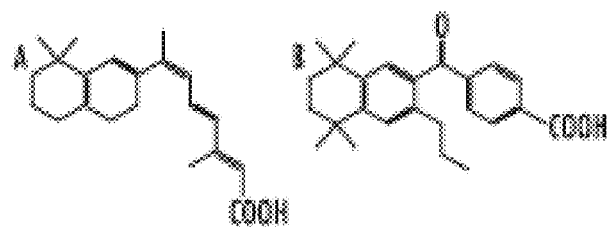
FIGS. 15a-b show the structure of exemplary ligands used in chemical complementation of one embodiment.

The binding pocket of the RXR LBD is composed of primarily hydrophobic side chains plus several positively charged residues that stabilize the negatively charged carboxylate group of 9cRA. The target ligand, LG335, contains an analogous carboxylate group, so the positively charged residues were left unchanged. The binding affinity probably arises from hydrophobic contacts and that specificity arises from binding pocket size, shape, hydrogen bonding, and electrostatics. The randomized amino acids were chosen based on their proximity to the bound 9cRA as observed in the crystal structure and the results of site directed mutagenesis (FIG. 14, (Egea et al., (2000) *EMBO J.* 19: 2592-2601; Doyle et al., (2001) *J. Am. Chem. Soc.* 123: 11367-11371, incorporated herein by reference in their entireties)). The electrostatic interactions were held constant while the size, shape, and potential hydrogen bonding interactions were varied to find optimum contacts for LG335 binding. A library of RXRs with mutations at six positions was created. At three of the positions (I268, A271, and A272) are four possible amino acids (L, V, A, and P) and at the other three positions (I310, F313, and L436) there are eight possible amino acids (L, I, V, F, M, S, A, and T). The combination of six positions and number of encoded amino acids allowed testing of the library construction while keeping the library size (32,768 amino acid combinations and about 3 million codon combinations) within reasonable limits. Proline was included in the library as a negative control. Residues 268, 271, and 272 are in the middle of helix 3, which would be disrupted by the inclusion of proline. Therefore, proline residues should appear at these positions only in unselected variants and not in the variants that activate in response to ligand. The substitutions at positions 268, 271, and 272 were restricted to small amino acids allowing access to the positively charged residues at this end of the pocket.

To eliminate contamination of the library with unmutated, wild-type RXR the gene was modified to create a non-functional gene, RXR:3Stop. Forty base pairs were deleted at three separate sites producing three stop codons in the coding region to create this nonfunctional gene. The deletions correspond to regions in the RXR gene where randomized codons are designed. This plasmid, pGBDRXR:3Stop, was co-transformed into yeast with the library of insert cassettes containing full-length RXR LBD genes with randomized codons at positions 268, 271, 272, 310, 313, and 436. The insert cassettes and the plasmid contain homologous regions enabling the yeast to homologously recombine the cassette into the plasmid. Recombination repairs the deletions in the RXR:3Stop gene to make full-length genes with mutations at the six specific sites.

Example 10

Library Selection

To limit the number of variants to be screened, the library was subjected to chemical complementation (FIG. 1). Chemical complementation exploits the power of genetic selection to make the survival of yeast dependent on the presence of a small molecule. The PJ69-4A strain of *S. cerevisiae* has been engineered for use in yeast two-hybrid genetic selection and screening assays. For selection, PJ69-4A contains the ADE2 gene under the control of a Gal4 response element. Plasmids created through homologous recombination in PJ69-4A express the Gal4 DBD fused with a variant RXR LBD (GBD:RXR). A plasmid expressing ACTR, a nuclear receptor coactivator, fused with the Gal4 activation domain (ACTR:GAD), was also transformed into PJ69-4A. If a ligand causes a variant RXR LBD to associate with ACTR, transcription of the ADE2 gene is activated. Expression of ADE2 permits adenine biosynthesis and therefore, yeast survival on media lacking adenine.

A small amount of the yeast library was plated onto media (SC-Leu-Trp) selecting only for the presence of the plasmids pGAD10-BA-ACTR (expressing ACTR:GAD and containing a leucine selective marker) and mutant pGBDRXR (expressing variant GBD:RXR and containing a tryptophan selective marker). The majority of the yeast cells transformed with the RXR library were plated directly onto SC-Leu-Trp-Ade media containing 10 µM LG335, selecting for adenine production in response to the compound LG335. The transformation efficiency of this library into yeast strain PJ69-4A was $3.8 \times 10^4$ colonies per µg DNA. This number includes both the efficiency of transforming the DNA into the cells and the homologous recombination efficiency. Of the approximately 380,000 transformants, approximately 300 grew on SC-Ade-Trp-Leu+10 µM LG335 selective media.

Example 11

Library Characterization

Twenty-one plasmids were rescued from yeast colonies: nine from non-selective plates (SC-Trp-Leu) and twelve from selective plates (SC-Ade-Trp-Leu+10 µM LG335). The relevant portion of plasmid DNA from these colonies was sequenced to determine the genotype (Table 1). All nine of the plasmid sequences from the non-selective plates contained at least one deletion and are non-functional genes. Of the twelve plasmids that grew on the selective media, all contain full-length RXR LBDs with designed mutations. With 95% certainty, we conclude that the unselected library is at least 72% background and the selected library is at least 78% designed sequences (supporting information).

TABLE 1

Genotypes of mutants from unselected and selected libraries

| Mutant | I268 | A271 | A272 | I310 | F313 | L436 |
|---|---|---|---|---|---|---|
| Unselected library | | | | | | |
| 1 | Deleted | Deleted | Deleted | Deleted | Deleted | Deleted |
| 2 | Deleted | Deleted | Deleted | Deleted | Deleted | Deleted |
| 3 | GTA(V) | CCT(P) | CCT(P) | TCG(S) | TCG(S) | Deleted |
| 4 | Deleted | Deleted | Deleted | Deleted | Deleted | Deleted |
| 5 | Deleted | Deleted | Deleted | Deleted | Deleted | GCG(A) |
| 6 | Deleted | Deleted | Deleted | Deleted | Deleted | Deleted |
| 7 | Deleted | Deleted | Deleted | Deleted | Deleted | Deleted |
| 8 | Deleted | Deleted | Deleted | Deleted | Deleted | Deleted |
| 9 | Deleted | Deleted | Deleted | Deleted | Deleted | TTC(F) |
| Selected library | | | | | | |
| 1 | GTG(V) | wtRXR | GCA | TTG(L) | ATG(M) | TTG |
| 2 | GTG(V) | wtRXR | GCA | GTG(V) | TCC(S) | TTG |
| 3 | CTA(L) | GCT | GCA | ATG(M) | GTG(V) | TTG |
| 4 | GCG(A) | wtRXR | GCA | TCC(S) | GTG(V) | TTC(F) |
| 5 | GCT(A) | GCT | GCA | GCC(A) | GCG(A) | TTC(F) |
| 6 | GCT(A) | GCT | GTT(V) | GCC(A) | GCG(A) | TTC(F) |
| 7 | CTT(L) | GCT | GCT | GTC(V) | ATC(I) | TTG |
| 8 | CTG(L) | GTG(V) | GCG | TTG(L) | TTG(L) | TTG |
| 9 | GTG(V) | GTG(V) | GCG | TTG(L) | GTG(V) | TTG |
| 10 | GTA(V) | wtRXR | GTG(V) | ATG(M) | TCC(S) | ATG(M) |
| 11 | GCG(A) | GCG | GCA | ATG(M) | GCG(A) | ACG(T) |
| 12 | GCG(A) | GCT | GCG | TCG(S) | GTC(A) | TTC(F) |

Sequences codons are followed by the encoded amino acid in parentheses. "wtRXR" indicates that the sequence corresponds to the wild-type RXR codon. "Deleted" indicates the presence of an unmutated stop deletion background cassette.

Example 12

Variant Characterization in Yeast

Figure 2:
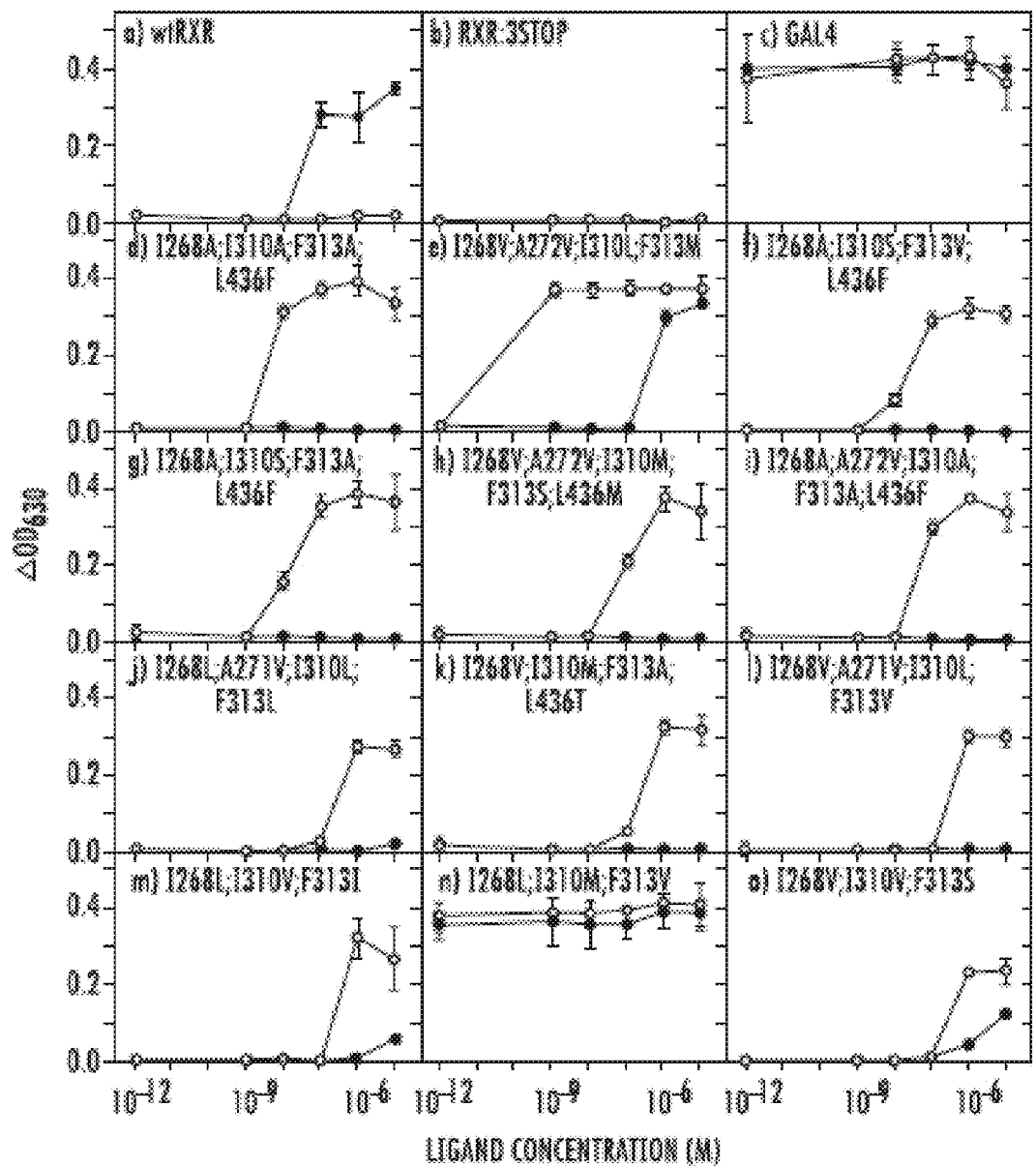
FIGS. 2a-o are line graphs showing selection assay (SC-Ade-Trp-Leu+ligand) data for yeast growth in the presence of 9cRA (closed circles) and LG335 (open circles) for 43 hours.
Figure 3:
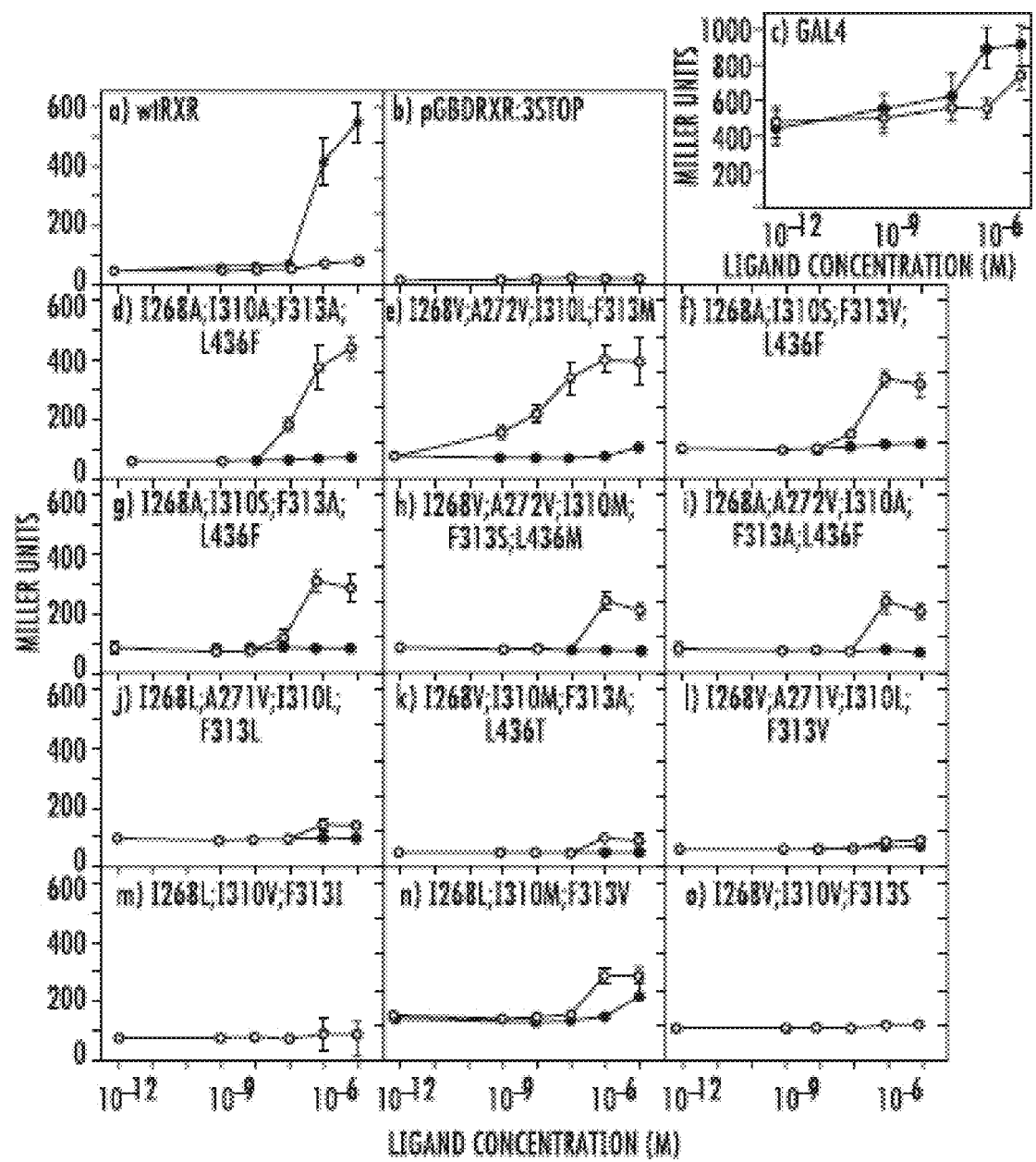
FIGS. 3a-o are line graphs showing screen assay (SC-Trp-Leu+ligand) data for β-galactosidase activity with o-Nitrophenyl β-D-galactopyranoside (ONPG) substrate in the presence of 9cRA (closed circles) and LG335 (open circles). Miller units normalize the change in absorbance at 405 nm for the change optical density at 630 nm, which reflects the number of cells per well.

The twelve plasmids rescued from the selective plates were retransformed into PJ69-4A to confirm that their phenotype is plasmid linked. The strain PJ69-4A was engineered to contain a Gal4 response element controlling expression of the LacZ gene, in addition to the ADE2 gene. Both selection and screening were used to determine the activation level of each variant by 9cRA and LG335. The selection assay quantifies yeast growth occurring through transcriptional activation of the ADE2 gene, while the screen quantifies β-galactosidase activity occurring though transcriptional activation of the LacZ gene. Although the selection assay (FIG. 2) is about 10-fold more sensitive than the screen (FIG. 3), it does not quantify activation level (efficacy) as well as the screen. In the selection assay, there is either growth or no growth, whereas the screen more accurately quantifies different activation levels at various concentration of ligand (FIGS. 2 and 3). The differences will be more fully discussed in a future publication.

Three plasmids were used as controls in the screen and selection assays. The plasmids pGBDRXRα and pGBT9Gal4 were used as positive controls to which the activation level of the variants can be compared. pGBDRXRα expresses the gene for the "wild-type" GBD:RXR, which grows and is activated by 9cRA but not by LG335. pGBT9Gal4 expresses the gene for the ligand-independent yeast transcription factor Gal4 (Johnston et al., (1986) Proc. Nat. Acad. Sci. USA 83: 6553-6557, incorporated herein by reference in its entirety), which is constitutively active in the presence or absence of either ligand. The plasmid pGBDRXR:3Stop serves as a negative control. pGBDRXR:3Stop carries a non-functional RXR LBD gene; therefore, yeast transformed with this plasmid does not grow in the selection assay nor show activity in the screen. This plasmid provides a measure of background noise in both the selection and screen assays.

Both the selection and screen assays show that ten of the twelve variants are selectively activated by LG335. Results of these assays are shown in FIGS. 2 and 3. Table 2 summarizes the transcriptional activation profiles of all twelve variants in response to both 9cRA and LG335 compared to wild-type RXR.

TABLE 2

$EC_{50}$ and efficacy in yeast and HEK 293 cells for RXR variants

| | 9CRA | | | | LG335 | | | |
|---|---|---|---|---|---|---|---|---|
| | Yeast | | HEK 293 | | Yeast | | HEK 293 | |
| Variant | $EC_{50}$ | Eff | $EC_{50}$ | Eff | $EC_{50}$ | Eff | $EC_{50}$ | Eff |
| WT | 500 | 100 | 220 | 100 | >10,000 | 10 | 300 | 10 |
| I268A; I310A; F313A; L436F | >10,000 | 0 | >10,000 | 0 | 220 | 70 | 30 | 50 |
| I268V; A272V; I310L; F313M | >10,000 | 10 | 1,600 | 30 | 40 | 60 | 1 | 30 |
| I268A; I310S; F313V; L436F | >10,000 | 10 | — | — | 470 | 60 | — | — |

TABLE 2-continued

EC$_{50}$ and efficacy in yeast and HEK 293 cells for RXR variants

| | 9CRA | | | | LG335 | | | |
| | Yeast | | HEK 293 | | Yeast | | HEK 293 | |
| Variant | EC$_{50}$ | Eff | EC$_{50}$ | Eff | EC$_{50}$ | Eff | EC$_{50}$ | Eff |
|---|---|---|---|---|---|---|---|---|
| I268A; I310S; F313V; L436F | >10,000 | 0 | >10,000 | 0 | 430 | 50 | 690 | 20 |
| I268V; A272V; I310M; F313S; L436M | >10,000 | 10 | >10,000 | 0 | 680 | 30 | 180 | 30 |
| I268A; A272V; I310A; F313A; L436F | >10,000 | 0 | — | — | 530 | 30 | 1 | — |
| I268L; A271V; I310L; F313L | >10,000 | 0 | — | — | 530 | 20 | 1 | — |
| I268A; I310M; F313A; L436T | >10,000 | 0 | >10,000 | 0 | 610 | 10 | 140 | 20 |
| I268V; A271V; I310L; F313V | >10,000 | 0 | — | — | 650 | 10 | — | — |
| I268L; I310V; F313I | >10,000 | 0 | — | — | >2000 | 10 | — | — |
| I268L; I310M; F313V | >10,000 | 20 | — | — | 610 | 20 | — | — |
| I268V; I310V; F313S | >10,000 | 0 | — | — | 440 | 10 | — | — |

EC$_{50}$ values (given in nm) represent the averages of two screen experiments in quadruplicate for yeast and in triplicate for HEK 293. Efficacy (Eff; given as a percent) is the maximum increase in activation relative to the increase in activation of wild type with 10 μM 9cRA. Values represent the averages of two screen experiments in quadruplicate for yeast and in triplicate in HEK 293.

Five variants were chosen for testing in mammalian cell culture for comparison of the activation profiles (I268A; I310A;F313A;L436F,I268V;A272V;I310L;F313M, I268A; I310S;F313A;L436F, I268V;A272V;I310M;F313S;L436M, and I286A;I310M;F313A;L436T). The genes for these variants were removed from yeast expression plasmids and ligated into mammalian expression plasmids.

Although I268L;I310M;F313V is constitutively active in the selection assay (FIG. 2n) and has high basal activity in the screen assay, both 9cRA and LG335 increase activity at micromolar concentrations (FIG. 3n). This variant may be in an intermediate conformation, with weakly activated transcription that can be improved by ligand binding. The high basal activation could also be due to a change in the conformation equilibrium with a shift towards the active conformation when ligand is not present.

I268V;I310V;F313S is constitutively active on solid media (data not shown), but shows no activation in the screen (0% Eff., Table 2, FIG. 3o) and only grows in the liquid media selection after two days (FIG. 2o). The basal activation level may be below the threshold of detection for the liquid media assays. However, it is also possible that agar, which is not present in the liquid assays, contains some small molecule that activates the receptor.

Figure 4:
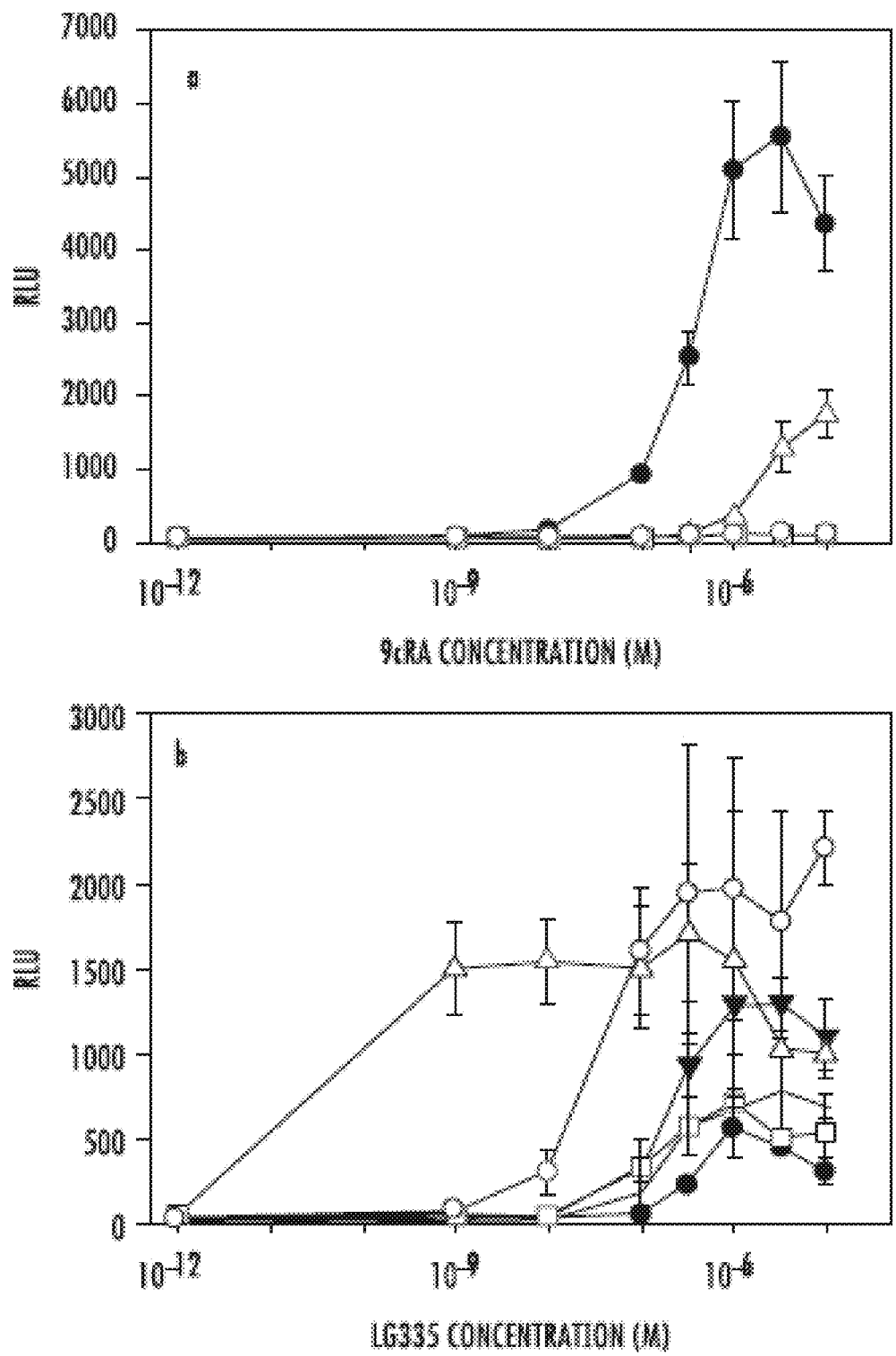
FIGS. 4a and b are line graphs showing data from mammalian cell culture using a luciferase reporter with wtRXR (solid circle), I268A;I310S;F313A;L436F (solid dot), I268V;A272V;I310M;F313S;L436M (inverted triangle), I268A;I310M;F313A;L436T (gray square), I268V;A272V;I310L; F313M (upright triangle), or I268A;I310A;F313A;L436F (grey circle) in response to (a) 9cRA and (b) LG335. RLU=relative light units.

Activation levels and EC$_{50}$s correlate in yeast and HEK 293 cells (FIG. 4 and Table 2). For the majority of the variants 9cRA shows little or no activation in yeast or mammalian cells. Variant I268V;A272V;I310L;F313M is activated slightly by 9cRA in yeast, but in mammalian cells is activated to the same level as with both 9cRA and LG335 (FIGS. 2, 3 and 4). With one exception, all variants tested have EC$_{50}$s within 10-fold in yeast and mammalian cells. However, the EC$_{50}$s in mammalian cells are generally lower than in yeast. We speculate that this shift is due to increased penetration of LG335 into mammalian cells versus yeast.

Subtle differences in binding pocket shape can have a drastic effect on specificity. For example, the I268V;A272V; I310L;F313M variant is activated to high levels by LG335 (60% Eff. Table 2), and is only slightly activated by 10 μM 9cRA in yeast (FIG. 3e), yet the amino acid changes are extremely conservative. The volume difference between phenylalanine and methionine side chains is only about 4 Å$^3$ and their polarity difference is minimal (hydration potentials of the methionine and phenylalanine side chains are −0.76 kcal mol$^{-1}$ and −1.48 kcal mol$^{-1}$, respectively). The other mutations redistribute methyl groups within the binding pocket, with a net difference of one methyl group (about 18 Å$^3$).

The LG335-I268V;A272V;I310L;F313M ligand receptor pair also represents a 25-fold improvement in EC$_{50}$ over the previous best LG335 receptor, Q275C;I310M;F313I (40 nM vs. 1 μM in yeast). The Q275C;I310M;F313I variant was created using site directed mutagenesis. Subtle changes in the I268V;A272V;I310L;F313M variant produced a better ligand receptor pair than the Q275C;I310M;F313I variant. This conclusion is consistent with the observation that nuclear receptors bind ligands through an induced-fit mechanism. With current knowledge about protein-ligand interactions it is not possible to rationally design ligand-receptor pairs with specific activation profiles. Libraries and chemical complementation are a new way to circumvent this problem and obtain functional variants with a variety of activation profiles.

Molecular modeling was used to generate hypotheses about the structural basis of ligand specificity for the variants discovered in the library. First, mutations to smaller or more flexible side chains at positions 310, and 313 are essential to provide space for the propyl group of LG335. All variants activated by LG335 have mutations at these two positions. Second, mutations to amino acids with larger side chains at position 436 sterically clash with the methyl group at the 9 position of 9cRA. This interaction may prevent helix 12 from closing properly and therefore prevent activation by 9cRA. The only variant significantly activated by 9cRA (I268V; A272V;I310L;F313M) does not contain a mutation at position 436. Third we hypothesize that tight packing in the binding pocket may lead to lower EC$_{50}$s. The docking results for I268V;A272V;I310L;F313M with LG335 show that the methionine and leucine side chains pack tightly against the propyl group of LG335, which may result in tighter binding and consequently a lower EC$_{50}$s.

In the absence of functional data, chemical complementation may be used to test more hypotheses about the function of particular residues than would be possible through site directed mutagenesis. By making a library of changes at a single site, additional information could be obtained about the importance of side chain size, polarity, and charge over just the traditional mutation to alanine that is often used to explore single residue importance. In the absence of structural information, it is possible to make large libraries using error prone PCR or gene shuffling. Chemical complementation could also be used to select active variants from these types of libraries.

Example 13

Increasing the Sensitivity of Chemical Complementation with ACTR

To increase the sensitivity of chemical complementation, an adapter protein was introduced to link the mammalian nuclear receptor function to the yeast transcription apparatus, thereby overcoming the evolutionary divergence between mammalian cells and yeast. The human nuclear receptor coactivator ACTR was fused to the yeast Gal4 activation domain This plasmid, pGAD10-BA-ACTR, expresses the ACTR:GAD fusion protein and contains a leucine marker. This plasmid was co-transformed into yeast with the plasmid pGBDRXR, which expresses the Gal4 DNA binding domain (DBD) fused to the RXR ligand binding domain (GBD:RXR) and contains a tryptophan marker. Transformants were selected on SC-Leu-Trp plates, and were streaked onto adenine selective plates (SC-Ade) containing $10^{-5}$M 9cRA, a known ligand for RXR (FIG. 5G). Yeast containing just the pGBDRXR plasmid, the pGAD10-BA-ACTR plasmid, a plasmid with just the Gal4 DBD (pGBDMT), and a plasmid containing the Gal4 holo protein (pGBT9Gal4) were also streaked onto these plates as controls.

After two days of incubation, growth occurs on the sector of the plate containing ACTR:GAD with GBD:RXR and on the sector of the plate with Gal4; whereas no growth occurs on the sector of the plate with GBD:RXR alone (FIG. 5G). The growth density produced by GBD:RXR and ACTR:GAD is the same as the growth produced by the holo Gal4. Importantly, GBD:RXR and ACTR:GAD produced no growth on plates without 9cRA.

Figure 5:
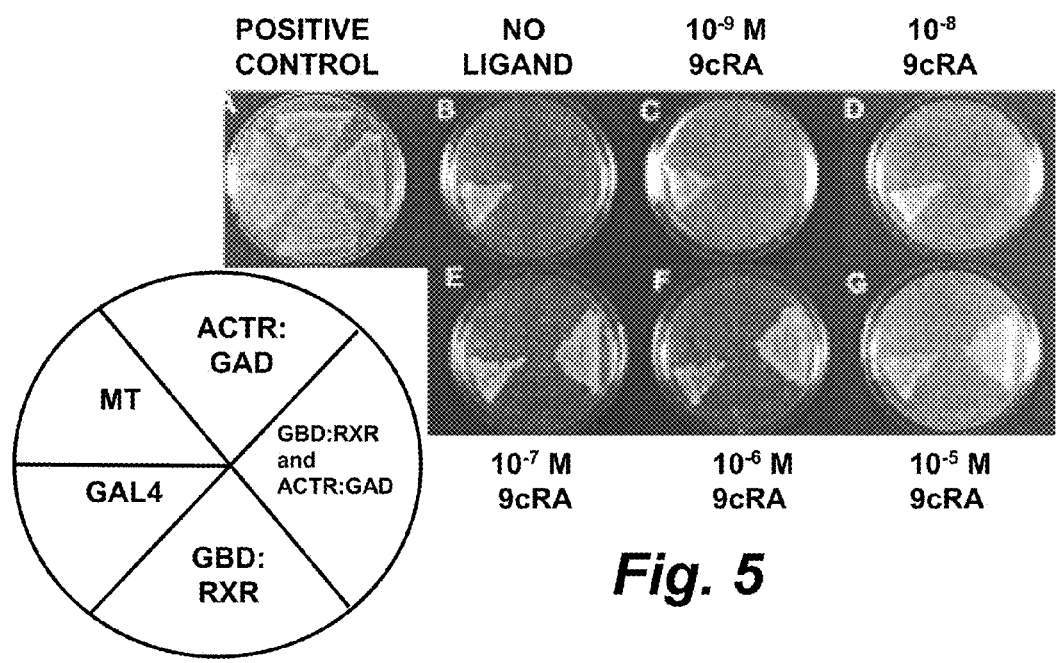
FIGS. 5a-g are photographs of culture plates showing yeast transformed with both ACTR:GAD and GBD:RXR growing in the presence of various concentrations of 9cRA.

Previous findings showed no growth was observed with RXR at 9cRA concentrations lower than $10^{-5}$ M. To determine if the sensitivity of our system had increased with the introduction of the adapter fusion protein, a dose response was performed on adenine selective plates (SC-Ade) containing ligand concentrations ranging from $10^{-5}$M to $10^{-9}$M. After two days of incubation, a clear dose response occurs on the plates (FIG. 5). Without ligand, growth occurs only on the Gal4 sector of the plate, as expected At concentrations as low as $10^{-8}$ M 9cRA, ligand-activated growth occurs only on the sector of the plate containing both GBD:RXR with ACTR: GAD (FIG. 5D). At concentrations of ligand above $10^{-8}$ M, higher density growth is observed on the sector of the plate containing GBD:RXR with ACTR:GAD. No growth occurs with GBD:RXR alone as expected. In summary, the introduction of the fusion protein ACTR:GAD increases the sensitivity of chemical complementation. Growth occurs on adenine selective plates with 9cRA after two days of incubation (FIG. 5). Ligand-activated growth is observed at 9cRA concentrations as low as $10^{-8}$ M 9cRA. With chemical complementation, an approximate $EC_{50}$ value between $10^{-8}$ M and $10^{-7}$ M for wild-type RXR and 9cRA, which is comparable to the $EC_{50}$ value measured for wild-type RXR in mammalian cell assays (about $10^{-7}$ M) (FIG. 5). The growth density and rate with the ACTR:GAD fusion protein is comparable to Gal4 activated growth. The same results were obtained on adenine selective plates (SC-Ade-Trp and SC-Ade-Leu-Trp) and on histidine selective plates (data not shown). In summary, introducing an adapter fusion protein of the human coactivator with the Gal4 activation domain increases the sensitivity of chemical complementation 1000-fold, making this system more efficient for analysis of protein/ligand interactions.

Example 14

Increasing Sensitivity of Chemical Complementation Using SRC-1

Figure 6:
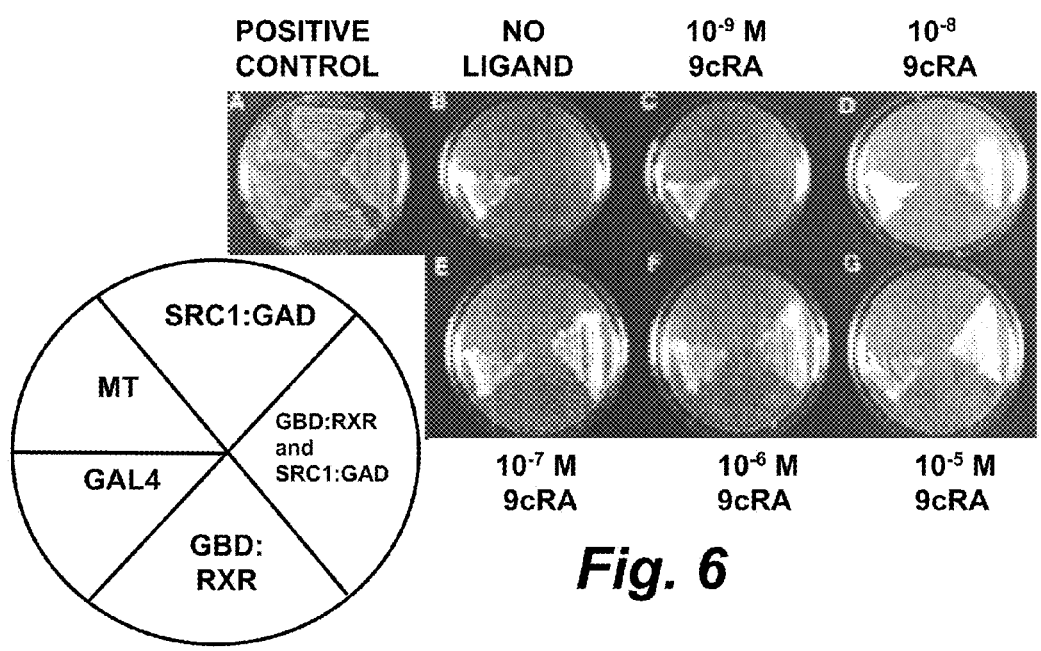
FIGS. 6a-g are photographs of culture plates showing yeast transformed with both SRC-1:GAD and GBD:RXR grow in the presence of various concentrations of 9cRA.

Another RXR coactivator was tested to increase the sensitivity of chemical complementation. Residues 54 to 1442 of the human nuclear receptor coactivator, SRC-1, were fused to the Gal4 activation domain to construct the plasmid pGAD10-BASRC1. This plasmid, which expresses SRC1: GAD in yeast and contains a leucine marker was transformed with GBD:RXR; transformants selected from SC-Leu-Trp were streaked onto adenine selective plates (SC-Ade) with various concentrations of 9cRA (FIG. 6). Ligand-activated growth is observed only in the sector of the plate containing both GBD:RXR with SRC1:GAD, and the same trend is observed with SRC-I as the ACTR coactivator (FIG. 6).

To verify that the increased sensitivity is from specific interactions between the coactivator and the active conformation of the receptor, a series of further controls was devised. pGAD10, a plasmid containing the Gal4 activation domain (GAD) without a coactivator domain was co-transformed with pGBDRXR. The plasmid was also transformed alone. pGAD10-BA-ACTR (SEQ ID NO.: 1), pGAD10-BASRC1, pGBT9Gal4, and pGBDMT were all transformed individually. These controls were streaked onto adenine selective plates (SC-Ade) with and without 9cRA. In the absence of ligand, only the entire Gal4 gene (pGBT9Gal4) grows as expected (data not shown). In the presence of $10^{-5}$ M 9cRA, growth occurs with the GBD:RXR with ACTR:GAD and GBD:RXR with SRC1:GAD. The Gal4 AD only (without the coactivator domain) with GBD:RXR displays no growth. These results verify that the increase in chemical complementation is specifically due to the interaction of the coactivator fusion protein with the ligand-bound nuclear receptor.

Example 15

Chemical Complementation and Negative Selection

Negative selection is the opposite of classical genetic complementation. Instead of allowing the microbe to survive, a functional gene kills the microbe; only cells containing non-functional genes survive and form colonies on selective plates. Negative selection is useful for finding mutations that disrupt the function of a protein.

For negative selection in yeast, others have generated yeast strains that contain Gal4 response elements (REs) fused to the URA3 gene. The URA3 gene codes for or orotidine-5'-phosphate decarboxylase, an enzyme in the uracil biosynthetic pathway. This gene can be used for both positive and negative selection. For positive selection, yeast expressing this gene will survive in the absence of uracil in the media. For negative selection, uracil and 5-fluoroorotic acid (FOA) is added to the media. Expression of orotidine-5'-phosphate decarboxylase coverts FOA to the toxin 5-fluorouracil, which kills the yeast. As used herein, the term "negative chemical complementation" refers to negative selection that occurs due to the presence of a small molecule.

Figure 7:
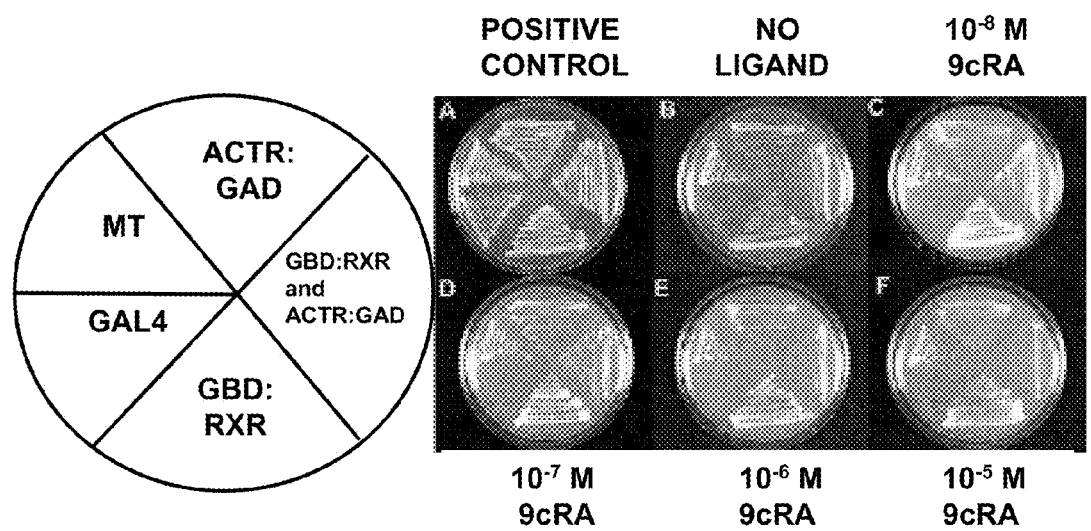
FIGS. 7a-f are photographs of culture plates showing negative selection of yeast transformed with both ACTR:GAD and GBD:RXR in the presence of various concentrations of 9cRA.

Plasmids pGBDRXR and pGAD10-BA-ACTR were individually transformed and co-transformed into MaV103. Transformants were streaked onto uracil selective plates (SC-Ura-Trp) with 9cRA for positive selection. The same trend was seen with the ACTR:GAD with GBD:RXR in the MaV103 strain as seen previously with the PJ69-4A strain. The same transformants were streaked onto selective plates (SC-Leu-Trp) with FOA for negative chemical complementation. Varying concentrations of 9cRA were also added to the plates, ranging from $10^{-5}$ M to $10^{-8}$ M. In the absence of ligand (FIG. 7B), yeast grow on the sector of the plate containing ACTR:GAD with GBD:RXR as expected. This is expected because uracil is provided, and in the absence of ligand RXR maintains its inactive conformation, preventing ACTR:GAD from binding and transcription does not occur. Without expression of the URA3 gene, 5-fluorouracil is not produced and the yeast survive. However, as the concentration of ligand increases (FIG. 7B-7F), less growth occurs and at the highest concentration of ligand, $10^{-5}$ M, very little growth occurs. The small amount of growth that is observed is due to background growth associated with negative selection in this strain.

Negative chemical complementation is advantageous for engineering receptors for new small molecules for several reasons. First, mutant receptor libraries may contain constitutively active receptors or receptors that activate transcription in response to endogenous small molecules. These undesirable receptors can be removed from the library with negative selection. Second, in some cases it will be desirable to remove members of the library that activate in response to certain small molecules, e.g. the natural ligands. Negative chemical complementation will remove these members of the library. The remaining library can then be put through chemical complementation with the small molecule of interest. Third, for enzyme engineering negative chemical complementation can remove library members that produce a particular small molecule, e.g. an enantiomer of the compound of interest. The remaining mutant enzyme library can then be put through chemical complementation to find those capable of producing the small molecule of interest. Fourth, for drug discovery, chemical libraries can be efficiently evaluated for antagonists of nuclear receptors by their ability to allow the yeast to survive negative chemical complementation.

Example 16

Chemical Complementation with RXR Mutants

Several RXR mutants previously tested in both mammalian cell assays and with chemical complementation in yeast (without the coactivator fusion protein) showed a general, but less than complete correlation. Without the coactivator fusion protein, ligand-activated growth was observed only with wild-type RXR and the F439L mutant after five days of incubation; none of the other mutants showed ligand-activated growth. The variation in the transcription machinery could lead to the different patterns in activation. To test whether the adapter fusion protein could overcome the differences and show a more direct correlation, all the mutants in Table 3 were cloned into pGBD vectors and co-transformed into yeast with pGAD10-BA-ACTR. Again, transformants were selected from SC-Leu-Trp plates and then streaked onto adenine selective plates (SC-Ade-Trp). These mutants were tested with 9cRA and LG335 (a near-drug, a synthetic compound structurally similar to an RXR agonist but that does not activate wild-type RXR) (Table 3).

Figure 8:
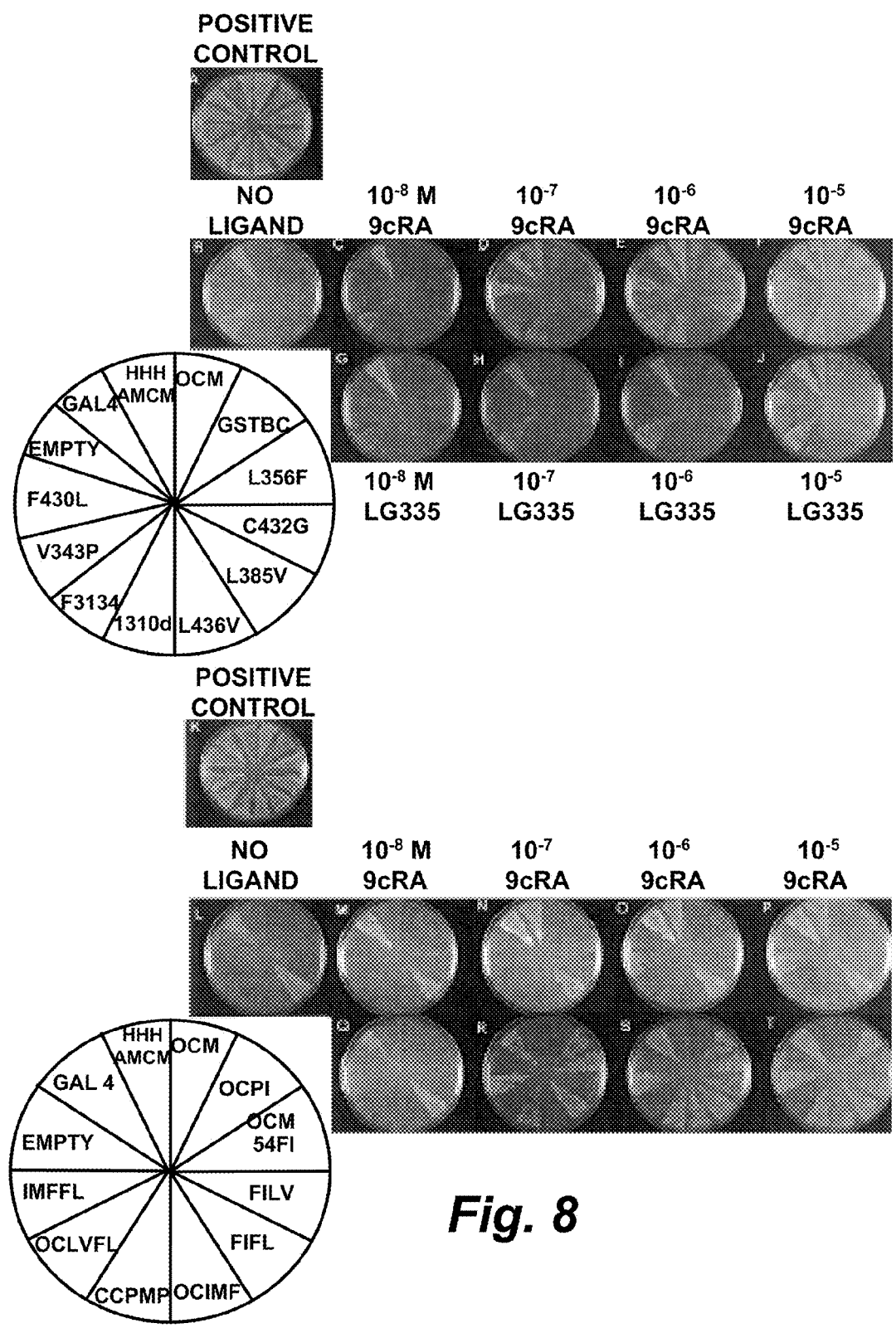
FIGS. 8a-t are photographs of culture plates showing growth due to the indicated transformants of variant GBD:RXRs due to various concentrations of 9cRA.
Figure 9:
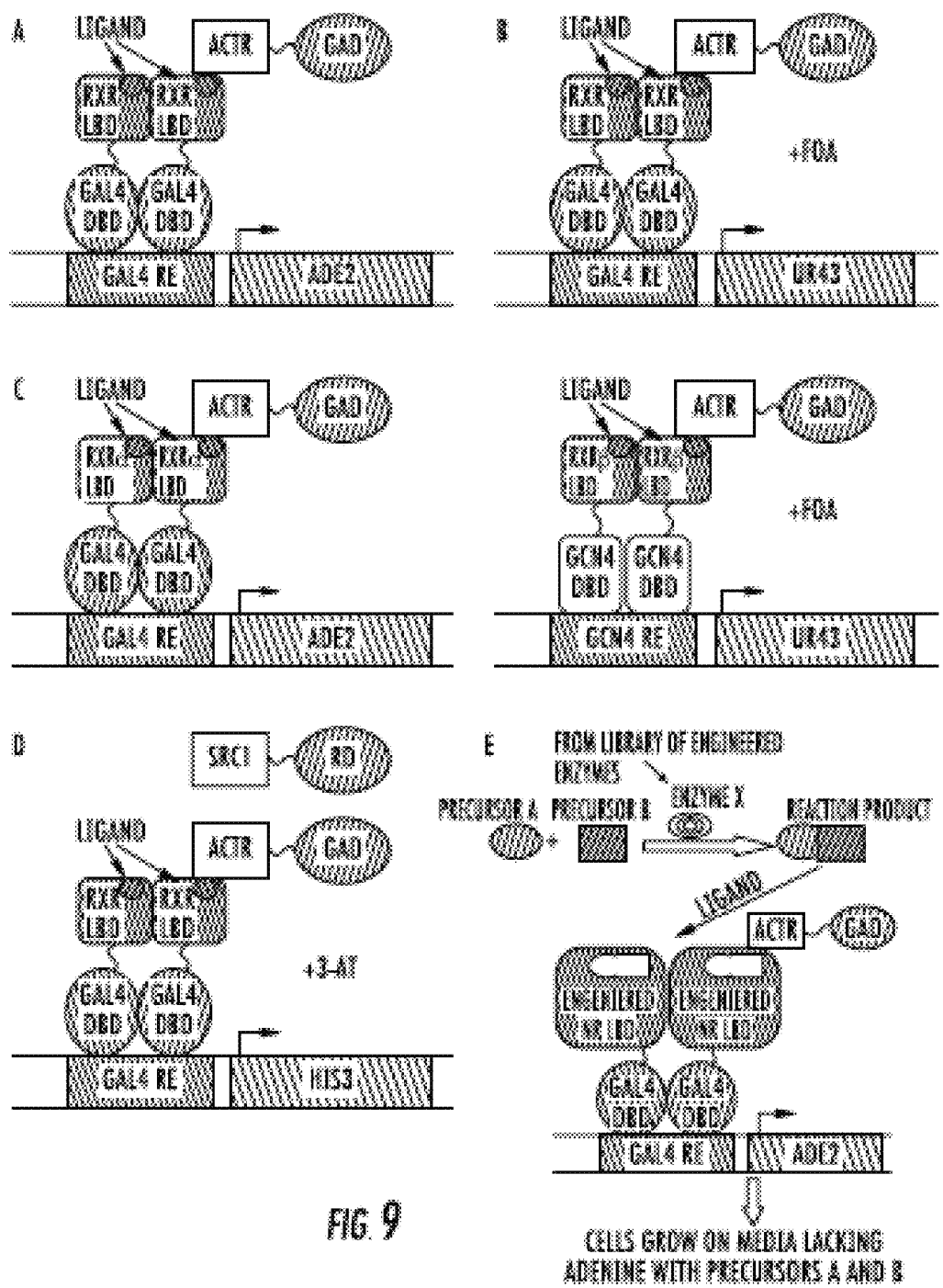
FIGS. 9a-e are schematics of exemplary embodiments for the selection of desired transformants.

The transcriptional activation patterns of these mutants in chemical complementation with the addition of ACTR:GAD was observed on dose response plates containing both 9cRA and the synthetic ligand, LG335 (FIG. 8). On the plate without ligand, growth occurs on the sector of the plate containing Gal4, but growth also occurs on the sector of the plate with the two mutants F313I and F313I;F439L, This could be a result of the mutations causing a structural modification to the binding pocket that is favorable for the binding of an endogenous small molecule in yeast. At $10^{-5}$ M 9cRA, growth occurs on the sectors of the plate with the single mutants, C432G, Q275C, I268F, I310M, V342F, and F439L, as well as some of the triple mutants I310M;F313I;F439L and Q275C;F313I; V342F. As the concentration of ligand decreases, some mutants no longer show ligand-activated growth. At $10^{-7}$ M 9cRA, growth is observed with the F439L mutant as well as wild-type RXR (FIG. 8). At the lowest concentration of ligand, $10^{-8}$M 9cRA, growth is observed in the Gal4 and F313I sectors of the plates. For the synthetic ligand LG335, growth is observed with several of the single, double and triple mutants at $10^{-5}$ M (FIG. 8). At lower concentrations of ligand, the single mutants do not show much growth. However, several of the double and triple mutants I310M;F313I; F439L, Q275C;F313I, and I310M;F313I display ligand-activated growth at $10^{-7}$M LG335. At $10^{-8}$ M LG335, some growth is still observed in the I310M;F313I;F439L sector of the plate.

A correlation is apparent between yeast growth and transcriptional activation in mammalian cells when quantitating these results and comparing them with results from cell culture assays (Table 3). The I268F, Q275C, C432G, I310M, and I310M; F313I; F439L mutations which had previously not shown any growth with chemical complementation, grow with the ACTR:GAD fusion protein (FIG. 8). The more direct correlation between chemical complementation and mammalian cell assays shows that the coactivator fusion protein (ACTR:GAD) serves to bridge millions of years of evolution by adapting mammalian nuclear receptor function to the yeast transcription machinery.

Example 17

Experimental Procedure for Enzyme-Linked Yeast Growth

An endogenous yeast compound was converted by two enzymes to a VDR-specific ligand allowing the yeast strain to survive and grow on a culture medium lacking histidine.

The yeast strain PJ69-4A (James et al., (1996) *Genetics* 144:1425-1436, incorporated herein in its entirety) was transformed using standard yeast transformation protocols according to Gietz et al., (2002) *Methods Enzymol.* 350:87-96, incorporated herein in its entirety, with various combinations of four plasmids: pVDR-wt (SEQ ID NO.: 20), expressing the GDB:VDR fusion protein; pGAD-BA-ACTR (SEQ ID NO.: 19), expressing the ACTR:GAD fusion protein; pY2653 (SEQ ID NO.: 22), expressing the CYP2R1 gene (encoding the P450 2R1 enzyme); and pS0016 (SEQ ID NO.: 21), expressing the CYP27B1 gene (encoding the P450 27B1 enzyme).

The endogenous yeast compound is proposed to be vitamin $D_2$ (ergocalciferol). Vitamin $D_2$ (which is not a VDR ligand) is converted by the enzyme P450 2R1 to 25-hydroxyvitamin $D_2$ (also not a VDR ligand) (Cheng et al., (2003) *J. Biol. Chem.* 278:38084-38093). The 25-hydroxyvitamin $D_2$ is converted by the P450 27B2 enzyme to 1α,25-dihydroxyvitamin $D_2$ (Takeyama et al., (1997) *Science* 277:1827-1830), which is a VDR ligand. 1α,25-dihydroxyvitamin $D_2$ binds and activates VDR, expressing the HIS3 gene, allowing the yeast to survive and grow on media lacking histidine. FIG. 22 illustrates schematically the conversion of the endogenous substrate to the VDR ligand 1α,25-dihydroxyvitamin $D_2$. FIG. 23 illustrates digital images of the growth results of the four types of transformants on His-culture medium.

The invention claimed is:

1. A yeast cell comprising:
   (i) a yeast transcription modulating system comprising a first heterologous nucleic acid expression system encoding a recombinant nuclear receptor polypeptide comprising a ligand-binding domain operably linked to a DNA-binding domain and optionally to a flexible hinge domain, wherein the recombinant nuclear receptor polypeptide, when expressed in the yeast cell in the presence of a nuclear receptor ligand specifically binding to the recombinant nuclear receptor polypeptide, activates expression of a selective genetic locus; and a second heterologous nucleic acid expression system encoding an adapter polypeptide comprising a coactivator domain operably linked to a yeast transcriptional activator, and wherein the first heterologous nucleic acid expression system and the second heterologous nucleic acid expression system are each independently encoded by individual heterologous polynucleotides or are encoded by the same heterologous polynucleotide;
   (ii) a nuclear receptor ligand generating system comprising a third heterologous nucleic acid expression system encoding a heterologous enzyme system for the generation of a nuclear receptor ligand from a substrate, wherein the nuclear receptor ligand is characterized as specifically binding to the recombinant nuclear receptor polypeptide; and
   (iii) a selective genetic locus expressed in the presence of the recombinant nuclear receptor polypeptide and a nuclear receptor ligand specifically bound to the recombinant nuclear receptor polypeptide.

2. The yeast cell according to claim 1, wherein the coactivator domain is SRC-1 or ACTR.

3. The yeast cell according to claim 1, wherein the third heterologous nucleic acid expression system comprises a heterologous polynucleotide encoding a heterologous polypeptide, said heterologous polypeptide having an enzymic activity characterized as generating a candidate nuclear receptor ligand from a substrate.

4. The yeast cell according to claim 1, wherein the third heterologous nucleic acid expression system comprises a heterologous polynucleotide encoding a plurality of heterologous polypeptides, wherein said heterologous polypeptides cooperate to generate a candidate nuclear receptor ligand from a substrate.

5. The yeast cell according to claim 1, wherein the third heterologous nucleic acid expression system comprises a plurality of heterologous polynucleotides encoding a plurality of heterologous polypeptides, wherein said heterologous polypeptides cooperate to generate a candidate nuclear receptor ligand from a substrate.

6. The yeast cell according to claim 1, wherein the ligand-binding domain of the recombinant nuclear receptor polypeptide is a ligand-binding domain of a human nuclear receptor polypeptide.

7. The yeast cell according to claim 1, wherein the coactivator domain of the adapter polypeptide is a coactivator domain of a human coactivator, and wherein the coactivator domain is characterized as binding to the ligand-binding domain of the recombinant nuclear receptor polypeptide in the presence of a ligand.

8. The yeast cell according to claim 1, wherein expression of the genetic locus allows proliferation of the yeast cell on a selective medium.

9. The yeast cell according to claim 1, wherein expression of the genetic locus inhibits proliferation of the yeast cell on a selective medium.

10. The yeast cell according to claim 1, wherein the heterologous enzyme system for the generation of a nuclear receptor ligand from a substrate comprises a modified enzyme, wherein said modified enzyme catalyzes the formation of a receptor ligand characterized as binding to the recombinant receptor polypeptide.

11. The yeast cell according to claim 1, wherein the heterologous enzyme system for the generation of a nuclear receptor ligand from a substrate comprises vitamin $D_3$ 25-hydroxylase and 25-hydroxyvitamin $D_3$ 1α-hydroxylase, wherein said heterologous enzyme system catalyzes the formation of 1α,25-dihydroxyvitamin $D_3$, and wherein the 1α,25-dihydroxyvitamin $D_3$ binds to the recombinant nuclear receptor polypeptide comprising the ligand-binding domain of a vitamin D receptor, thereby inducing expression of a genetic locus allowing the yeast cell to proliferate on a culture medium not having histidine therein, wherein the genetic locus is HIS3.

12. A method of modulating the transcription of a gene of a yeast cell, comprising
   (1) providing a yeast cell or population of yeast cells, wherein said yeast cell or population of yeast cells comprises:
      (i) a yeast transcription modulating system comprising a first heterologous nucleic acid expression system encoding a recombinant nuclear receptor polypeptide comprising a ligand-binding domain operably linked to a DNA-binding domain and optionally to a flexible hinge domain, wherein the recombinant nuclear receptor polypeptide, when expressed in the yeast cell in the presence of a nuclear receptor ligand specifically binding to the recombinant nuclear receptor polypeptide, activates expression of a genetic locus; and a second heterologous nucleic acid expression system encoding an adapter polypeptide, comprising a coactivator domain operably linked to a yeast transcriptional activator, and wherein the first heterologous nucleic acid expression system and the second heterologous nucleic acid expression system are each independently encoded by individual heterologous polynucleotides or are encoded by the same heterologous polynucleotide; and (ii) a nuclear receptor ligand generating system comprising a third heterologous nucleic acid expression system encoding a heterologous enzyme system for the generation of a nuclear receptor ligand from a substrate, wherein the nuclear receptor ligand is characterized as specifically binding to the recombinant nuclear receptor polypeptide;

(iii) a selective yeast genetic locus expressed in the presence of the recombinant nuclear receptor polypeptide and a nuclear receptor ligand specifically bound to the recombinant nuclear receptor polypeptide; and (2) culturing the yeast cell under conditions allowing the yeast cell to synthesize a nuclear receptor ligand from a substrate, whereupon the nuclear receptor ligand specifically binds to the recombinant nuclear receptor polypeptide, thereby inducing transcription of the selective yeast genetic locus.

13. The method of claim 12, wherein the step of providing a yeast cell or population of yeast cells further comprises delivering to the population of yeast cells a plurality of third heterologous nucleic acid expression systems encoding a plurality of enzyme systems suspected of generating from a substrate a nuclear receptor ligand specifically binding the recombinant nuclear receptor polypeptide, and wherein the step of culturing the yeast cell under conditions allowing the yeast cell to synthesize a nuclear receptor ligand from a substrate identifies a third heterologous nucleic acid expression system encoding an enzyme system generating the nuclear receptor ligand.

14. The method according to claim 12, wherein the substrate is endogenous to the yeast cell.

15. The method according to claim 12, wherein the substrate is exogenous to the yeast cell.

16. The method according to claim 12, further comprising the step of modifying the first heterologous nucleic acid expression system encoding the recombinant nuclear receptor polypeptide, thereby providing a variant recombinant nuclear receptor polypeptide specifically binding to the nuclear receptor ligand.

17. The method according to claim 12, further comprising the step of modifying the third heterologous nucleic acid expression system encoding the heterologous enzyme system, thereby allowing the heterologous enzyme system to generate the nuclear receptor ligand from the substrate.

18. The method according to claim 12, wherein the third heterologous nucleic acid expression system comprises a heterologous polynucleotide encoding a heterologous polypeptide, the heterologous polypeptide having an enzymic activity characterized as generating a candidate nuclear receptor ligand from a substrate.

19. The method according to claim 12, wherein the third heterologous nucleic acid expression system comprises a heterologous polynucleotide encoding a plurality of heterologous polypeptides, wherein said heterologous polypeptides cooperate to generate a candidate nuclear receptor ligand from a substrate.

20. The method according to claim 12, wherein the third heterologous nucleic acid expression system comprises a plurality of heterologous polynucleotides encoding a plurality of heterologous polypeptides, wherein said heterologous polypeptides cooperate to generate a candidate nuclear receptor ligand from a substrate.

21. The method according to claim 12, wherein the ligand-binding domain of the recombinant nuclear receptor polypeptide is derived from a ligand-binding domain of a human nuclear receptor polypeptide, or a variant thereof.

22. The method according to claim 12, wherein the coactivator domain of the adapter polypeptide is derived from a coactivator domain of a human coactivator, or a variant thereof, and wherein the coactivator binds to the ligand-binding domain of the recombinant nuclear receptor polypeptide in the presence of a ligand to activate expression of a genetic locus.

23. The method according to claim 12, wherein transcription of the yeast gene allows the yeast cell to proliferate on a selective culture medium.

24. The method according to claim 12, wherein transcription of the yeast gene inhibits yeast cell proliferation on a selective culture medium.

25. The method according to claim 12, wherein the method further comprises contacting the yeast cell with at least one compound suspected of modulating the activity of at least one enzyme of the heterologous enzyme system, thereby allowing the identification of the at least one compound as an activator or inhibitor of the at least one enzyme.

26. The method according to claim 25, wherein the at least one compound is suspected of enhancing the activity of at least one enzyme of the heterologous enzyme system.

27. The method according to claim 25, wherein the at least one compound is suspected of inhibiting the activity of at least one enzyme of the heterologous enzyme system.

28. The method of claim 12, wherein the method further comprises contacting the yeast cell with at least one compound suspected of modulating the transcriptional activity of the third heterologous nucleic acid expression system encoding a heterologous enzyme system, thereby allowing the identification of the at least one compound as an activator or inhibitor of the transcriptional activity of the third heterologous nucleic acid expression system.

29. The yeast cell according to claim 6, wherein the ligand-binding domain of the recombinant nuclear receptor polypeptide is a variant of the ligand-binding domain of a human RXR receptor, wherein the variant is selected from the group consisting of: variant 1268A, 1310S, F313V, L436F; variant 1268A, 1310S, F313V, L436F; variant 1268V, A272V, 1310M, F313S, L436M; variant 1268A, A272V, 1310A, F313A, L436F; variant 1268L, A271V, 1310L, F313L; variant 1268A, 1310M, F313A, L436T; variant 1268V, A271V, 1310L, F313V; variant 1268L, 1310V, F313I; variant 1268L, 1310M, F313V; and variant 1268V, 1310V, F313S.

* * * * *